(12) United States Patent
Sereshkeh et al.

(10) Patent No.: US 11,199,904 B2
(45) Date of Patent: Dec. 14, 2021

(54) BRAIN-COMPUTER INTERFACE PLATFORM AND PROCESS FOR CLASSIFICATION OF COVERT SPEECH

(71) Applicant: HOLLAND BLOORVIEW KIDS REHABILITATION HOSPITAL, Toronto (CA)

(72) Inventors: Alborz Rezazadeh Sereshkeh, North York (CA); Thomas Tak Kin Chau, Toronto (CA)

(73) Assignee: HOLLAND BLOORVIEW KIDS REHABILITATION HOSPITAL, Toronto (CA)

(*) Notice: Subject to any disclaimer, the term of this patent is extended or adjusted under 35 U.S.C. 154(b) by 149 days.

(21) Appl. No.: 16/153,085

(22) Filed: Oct. 5, 2018

(65) Prior Publication Data
US 2019/0107888 A1 Apr. 11, 2019

Related U.S. Application Data

(60) Provisional application No. 62/642,180, filed on Mar. 13, 2018, provisional application No. 62/569,184, filed on Oct. 6, 2017.

(51) Int. Cl.
*G06F 3/01* (2006.01)
*A61B 5/00* (2006.01)
(Continued)

(52) U.S. Cl.
CPC ............ *G06F 3/015* (2013.01); *A61B 5/0042* (2013.01); *A61B 5/1103* (2013.01);
(Continued)

(58) Field of Classification Search
CPC .... G06F 3/015; A61B 5/0042; A61B 5/04012
See application file for complete search history.

(56) References Cited

U.S. PATENT DOCUMENTS

| 7,904,507 B2* | 3/2011 | Jung | A61B 5/16 709/203 |
| 9,946,344 B2* | 4/2018 | Ayaz | G06F 3/015 |

(Continued)

FOREIGN PATENT DOCUMENTS

WO 2017068414 A2 4/2017

OTHER PUBLICATIONS

Yoshimura, N., Nishimoto, A., Belkacem, A. N., Shin, D., Kambara, H., Hanakawa, T., & Koike, Y. (2016). Decoding of covert vowel articulation using electroencephalography cortical currents. Frontiers in neuroscience, 10, 175.*
(Continued)

*Primary Examiner* — Bryan S Blankenagel

(57) ABSTRACT

A device and method are provided for real-time classification of covert speech. The device comprises a plurality of sensors for capturing real-time bio-signal data for brain monitoring in response to mental tasks delivered to a user, and a brain computer interface with memory storing instructions to configure a processor to perform a method of real-time classification of covert speech. The method comprises capturing real-time bio-signal data for brain monitoring in response to mental tasks delivered to a user, pre-processing the raw bio-signal data, extracting a vector of features from the raw bio-signal data, selecting features from the vector of features, building classification model to generate classified covert speech data using the selected features, and controlling a display device with visual elements based on the classified covert speech data.

19 Claims, 27 Drawing Sheets

(51) Int. Cl.
- A61B 5/316 (2021.01)
- A61B 5/374 (2021.01)
- A61B 5/378 (2021.01)
- A61B 5/398 (2021.01)
- A61B 5/11 (2006.01)
- A61B 5/1455 (2006.01)
- G06F 3/16 (2006.01)
- G06K 9/00 (2006.01)

(52) U.S. Cl.
CPC .......... A61B 5/14553 (2013.01); A61B 5/316 (2021.01); A61B 5/374 (2021.01); A61B 5/378 (2021.01); A61B 5/398 (2021.01); A61B 5/725 (2013.01); A61B 5/726 (2013.01); A61B 5/7207 (2013.01); A61B 5/7264 (2013.01); G06F 3/167 (2013.01); G06K 9/00523 (2013.01); A61B 5/4803 (2013.01); A61B 5/7203 (2013.01); A61B 2505/09 (2013.01)

(56) References Cited

U.S. PATENT DOCUMENTS

| | | | |
|---|---|---|---|
| 2004/0249302 A1* | 12/2004 | Donoghue | A61B 5/04001 600/544 |
| 2009/0157482 A1* | 6/2009 | Jung | A61B 5/16 705/7.33 |
| 2013/0184558 A1 | 7/2013 | Gallant et al. | |
| 2014/0223462 A1* | 8/2014 | Aimone | H04N 21/4788 725/10 |
| 2017/0296080 A1* | 10/2017 | Yoon | A61B 5/7203 |
| 2019/0380657 A1* | 12/2019 | Pereira | A61B 34/10 |

OTHER PUBLICATIONS

Naseer, N., Hong, K. S., Bhutta, M. R., & Khan, M. J. (Apr. 2014). Improving classification accuracy of covert yes/no response decoding using support vector machines: an fNIRS study. In 2014 International Conference on Robotics and Emerging Allied Technologies in Engineering (iCREATE) (pp. 6-9). IEEE.*

Naseer, N., Hong, M. J., & Hong, K. S. (2014). Online binary decision decoding using functional near-infrared spectroscopy for the development of brain-computer interface. Experimental brain research, 232(2), 555-564.*

Salama, M., ElSherif, L., Lashin, H., & Gamal, T. (2014). Recognition of unspoken words using electrode electroencephalograhic signals. In The Sixth International Conference on Advanced Cognitive Technologies and Applications (pp. 51-55).*

Nguyen, C. H., Karavas, G. K., & Artemiadis, P. (2017). Inferring imagined speech using EEG signals: a new approach using Riemannian manifold features. Journal of neural engineering, 15(1), 016002.*

Brigham, K., & Kumar, B. V. (Sep. 2010). Subject identification from electroencephalogram (EEG) signals during imagined speech. In 2010 Fourth IEEE International Conference on Biometrics: Theory, Applications and Systems (BTAS) (pp. 1-8). IEEE.*

D'Zmura, M., Deng, S., Lappas, T., Thorpe, S., & Srinivasan, R. (Jul. 2009). Toward EEG sensing of imagined speech. In International Conference on Human-Computer Interaction (pp. 40-48). Springer, Berlin, Heidelberg.*

International Search Report and Written Opinion dated Nov. 30, 2018 in Application No. PCT/CA2018/051260.

* cited by examiner

| | No versus rest (first online session) | | | Yes versus no (second online session) | | |
|---|---|---|---|---|---|---|
| Participant number | First online block (%) | Second online block (%) after re-training the classifier | Average Classification accuracy — both block (%) | First online block (%) | Second online block (%) after re-training the classifier | Average Classification accuracy — both block (%) |
| 01 | 52.50 | 62.50 | 57.50 | 57.50 | 60.00 | 58.75 |
| 02 | 85.00 | 80.00 | 82.50* | 60.00 | 52.50 | 56.25 |
| 03 | 62.50 | 82.50 | 72.50* | 65.00 | 72.50 | 68.75* |
| 04 | 77.50 | 97.50 | 87.50* | 70.00 | 95.00 | 82.50* |
| 05 | 80.00 | 90.00 | 85.00* | 60.00 | 60.00 | 60.00* |
| 06 | 62.50 | 80.00 | 71.25* | 67.50 | 75.00 | 71.25* |
| 07 | 67.50 | 80.00 | 73.75* | 57.50 | 65.00 | 61.25* |
| 08 | 85.00 | 82.50 | 65.00* | 57.50 | 52.50 | 55.00 |
| 09 | 85.00 | 100 | 92.50* | 97.50 | 92.50 | 95.00* |
| 10 | 52.50 | 65.00 | 58.75 | 52.50 | 55.00 | 53.75 |
| 11 | 77.50 | 90.00 | 83.75* | 82.50 | 92.50 | 87.50* |
| 12 | 75.00 | 87.50 | 81.25* | 75.00 | 87.50 | 81.25* |
| AVG | 70.42 | 81.46 | 75.94 | 66.88 | 71.67 | 69.27 |
| SD | 11.37 | 12.72 | 11.35 | 12.89 | 16.53 | 14.12 |

FIG. 7

| Participant number | No versus rest test session | Yes versus no test session |
|---|---|---|
| 01 | 58.75 (↑ 1.25) | 58.75 (no change) |
| 02 | 78.75* (↓ 3.70) | 53.75 (↓2.50) |
| 03 | 70.00* (↓ 2.50) | 68.75* (no change) |
| 04 | 85.00* (↓ 2.50) | 81.25* (↓ 1.25) |
| 05 | 82.50* (↓ 2.50) | 60.00* (no change) |
| 06 | 70.00* (↓ 1.25) | 70.00* (↓ 1.25) |
| 07 | 71.25* (↓ 2.50) | 61.25* (no change) |
| 08 | 65.00* (no change) | 52.50 ↓ (2.50) |
| 09 | 90.00 (↓ 2.50) | 92.50* (↓ 2.50) |
| 10 | 57.50 (↓ 1.25) | 52.50 (↓1.25) |
| 11 | 83.75* (no change) | 85.00* (↓ 2.50) |
| 12 | 80.00* (↓ 1.25) | 81.25* (no change) |
| AVG | 74.38 (↓ 1.56) | 68.13 (↓ 1.14) |

BRAIN-COMPUTER INTERFACE PLATFORM AND PROCESS FOR CLASSIFICATION OF COVERT SPEECH

CROSS-REFERENCE TO RELATED APPLICATIONS

This application claims all benefit including priority to U.S. Provisional Patent Application 62/569,184, filed Oct. 6, 2017, and entitled: "Brain-Computer Interface Platform and Process for Online EEG Classification of Covert Speech", and to U.S. Provisional Patent Application 62/642,180, filed Mar. 13, 2018, and entitled: "Brain-Computer Interface Platform and Process for Classification of Covert Speech", each of which is hereby incorporated by reference in its entirety.

FIELD

Embodiments herein described relate to classification of covert speech using brain-computer interfaces (BCIs), electroencephalography (EEG) and/or functional near-infrared spectroscopy (fNIRS).

INTRODUCTION

Brain-computer interfaces (BCIs) is a communication pathway between an enhanced or wired brain and an external device. BCIs for communication can be nonintuitive and can require the performance of hand motor imagery or some other conversation-irrelevant task.

An electroencephalogram (EEG) detects electrical activity in brains using electrodes attached to your scalp. Brain cells communicate via electrical impulses and are active all the time. This electrical activity can be detected and measured by an EEG recording.

A functional near-infrared spectroscopy (fNIRS) detects optical signals in brains using NIR emitters having laser diodes that emit NIR light into the scalp and photodetectors to detect the NIR light it exits the scalp. The optical signals between source-detector pairs may be acquired and measured using a NIR spectrometer.

SUMMARY

In accordance with an embodiment, there is provided a device for real-time classification of covert speech. The device comprises a plurality of sensors for capturing real-time bio-signal data for brain monitoring in response to mental tasks delivered to a user, and a brain computer interface with memory storing instructions to configure a processor to perform a method of real-time classification of covert speech. The processor is configured to pre-process the raw bio-signal data, extract a vector of features from the raw bio-signal data using a spectral estimation method/algorithm and a time frequency method/algorithm, select features from the vector of features using a feature selection method/algorithm, build classification model to generate classified covert speech data using the selected features using at least one of a machine learning classifier method/algorithm and a regularization parameter, and control a display device with visual elements based on the classified covert speech data.

In accordance with another embodiment, there is provided a computer-implemented method of real-time classification of covert speech. The method is performed by a processor and comprises capturing real-time bio-signal data for brain monitoring in response to mental tasks delivered to a user, pre-processing the raw bio-signal data, extracting a vector of features from the raw bio-signal data using a spectral estimation method and a time frequency method, selecting features from the vector of features using a feature selection method, building a classification model to generate classified covert speech data using the selected features using at least one of a machine learning classifier method and a regularization parameter, and controlling a display device with visual elements based on the classified covert speech data.

In accordance with another embodiment, there is provided a non-transitory computer-readable storage medium having instructions thereon which when executed by a processor perform a method of real-time classification of covert speech. The method comprises capturing real-time bio-signal data for brain monitoring in response to mental tasks delivered to a user, pre-processing the raw bio-signal data, extracting a vector of features from the raw bio-signal data using a spectral estimation method and a time frequency method, selecting features from the vector of features using a feature selection method, building a classification model to generate classified covert speech data using the selected features using at least one of a machine learning classifier method and a regularization parameter, and controlling a display device with visual elements based on the classified covert speech data.

In various further aspects, the disclosure provides corresponding systems and devices, and logic structures such as machine-executable coded instruction sets for implementing such systems, devices, and methods.

In this respect, before explaining at least one embodiment in detail, it is to be understood that the embodiments are not limited in application to the details of construction and to the arrangements of the components set forth in this description or illustrated in the drawings. Also, it is to be understood that the phraseology and terminology employed herein are for the purpose of description and should not be regarded as limiting.

Many further features and combinations thereof concerning embodiments described herein will appear to those skilled in the art following a reading of the instant disclosure.

DESCRIPTION OF THE FIGURES

In the figures, embodiments are illustrated by way of example. It is to be expressly understood that the description and figures are only for the purpose of illustration and as an aid to understanding.

Embodiments will now be described, by way of example only, with reference to the attached figures, wherein in the figures:

FIG. 7 is a view of example online accuracies of "no" versus "rest" and "yes" versus "no" sessions, in accordance with some embodiments;

FIG. 11 shows example classification accuracies of the online sessions after the removal of EMG artifacts and EEG data pertaining to the primary cortex and premotor regions, in accordance with some embodiments;

DETAILED DESCRIPTION

Figure 1:
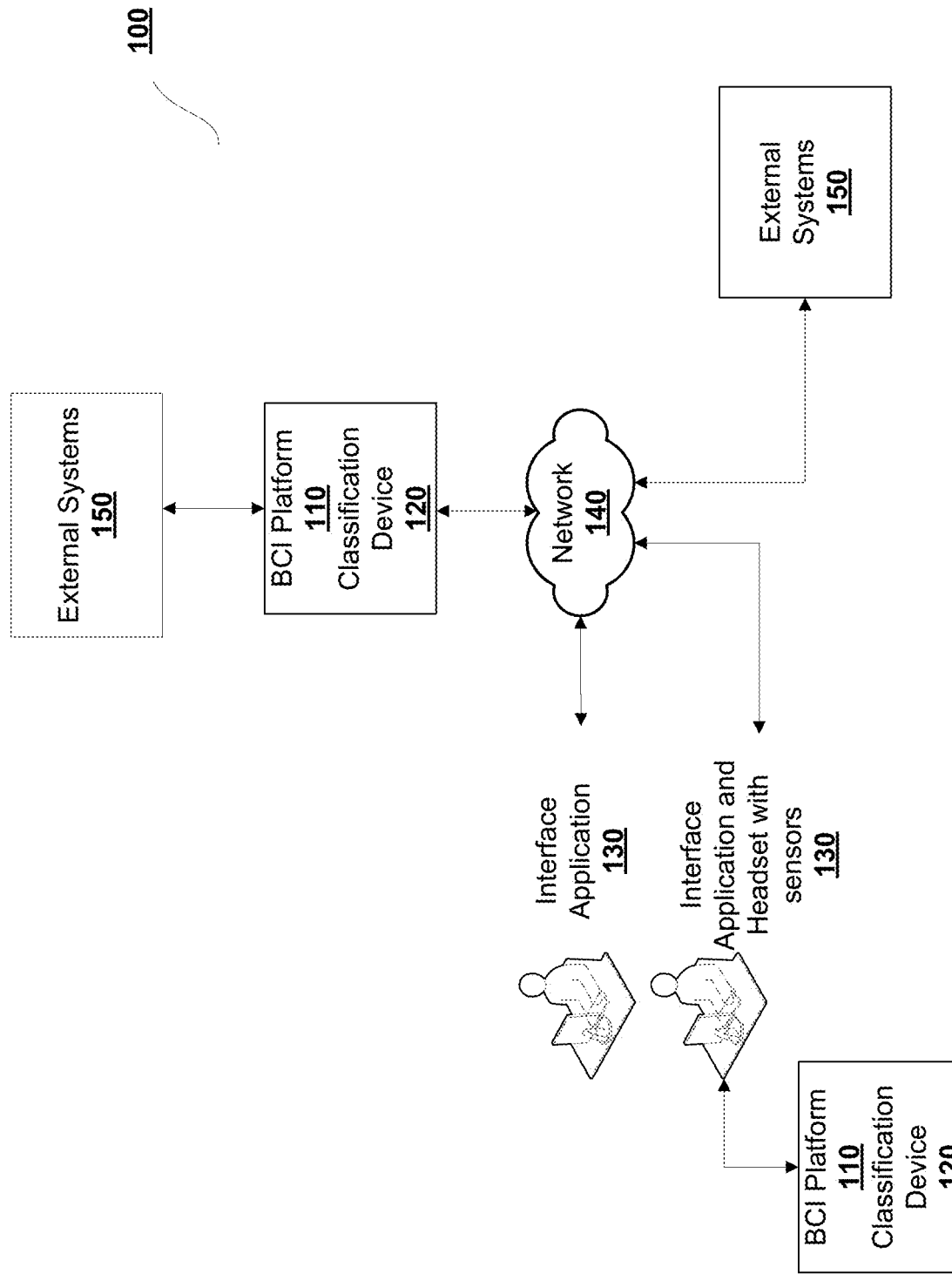
FIG. 1 is a view of an example brain-computer interface platform and interface application, in accordance with some embodiments.

Embodiments of methods, systems, and apparatus are described through reference to the drawings.

A goal of brain-computer interface (BCI) research is to provide a communication pathway for individuals with severe motor impairments who have very limited or no voluntary movement. A BCI can be a suitable means of communication for these individuals, as they perform a mental task or attend to a stimulus, without the need for muscle activity. However, common BCI activation tasks, such as mental arithmetic or word generation, have little or no correlation with typical communication. For example, a user may be required to perform mental arithmetic to answer basic yes or no questions, or to move his/her wheelchair around. This non-intuitiveness makes the assistive device difficult to use, limiting its potential to meaningfully improve quality of life.

Another common BCI activation task is motor imagery, which involves imagined movement of a specific part of the body. This mental task can be considered intuitive for certain applications, such as navigation or robotic control. However, it can be difficult or impossible for individuals with congenital or long-term motor impairments.

A mental task which has gained attention as an intuitive BCI task is "imagined speech". In this task, the BCI user is instructed to covertly say or repeat a phrase without moving the articulators.

BCIs may be developed to differentiate simple and intuitive mental tasks such as imagined speech or "yes" or "no" thoughts. Both electroencephalography (EEG) and functional near-infrared spectroscopy (fNIRS) may be used for this purpose. However, without invasive recording modalities, the classification accuracy and number of commands in such BCIs have been limited. The use of multi-modal BCIs, as a way of addressing these issues, has been proposed for some common BCI tasks, but not for imagined speech.

Brain-computer interfaces (BCIs) can be used to provide a communication channel for individuals with motor impairments who are unable to communicate independently. BCIs can be associated with various activation protocols. A subset of these protocols can be referred to as reactive BCIs, which require the user to attend to external stimuli. Examples include P300 spellers and BCIs based on steady-state visually evoked potentials. BCI protocols without the involvement an external stimulus, also known as active BCIs, require users to perform a mental task. Some examples of these mental tasks are motor imagery, mental arithmetic and word generation. Given an adequate classification accuracy, a BCI user can use each of these mental tasks to convey a different message, e.g., to answer yes or no questions. However, these mental tasks are usually difficult to perform by the target population since the tasks are non-intuitive and are unrelated to the message that he/she would want to convey.

An intuitive mental task for BCIs which has gained attraction during the last decade is covert speech—also known as inner speech or imagined speech. Based on the outcomes of some studies, most of the successful attempts (accuracy higher than 70%, the acceptable threshold for BCI application) to classify electrophysiological brain signals during covert speech used invasive measurement techniques such as electrocorticography (ECoG). On the other hand, most BCIs based on non-invasive measurements of these signals, including electroencephalography (EEG) and magnetoencephalography (MEG), yielded average accuracies of less than 70% when discriminating between two different covert speech tasks. Moreover, only one study used a real-time paradigm which reported an average classification accuracy of approximately 69% (~69%) using EEG signals recorded during covert repetition of "yes" and "no".

Brain-computer interfaces (BCIs) for communication can be non-intuitive, and can require the performance of hand motor imagery or some other conversation-irrelevant task. Embodiments described herein can implement BCIs developed using EEG and/or fNIRS. Embodiments described herein can involve electroencephalography (EEG) and functional near-infrared spectroscopy (fNIRS) to develop intuitive online BCIs based on covert speech.

A first example BCI can differentiate between 10 seconds (10 s) of mental repetitions of the word "no" and an equivalent duration of unconstrained rest. A second example BCI can be to discern between an interval, e.g., 1 s to 10 s, each of covert repetition of the words "yes" and "no". The interval can vary and is not fixed. This is an example interval. By way of an example experiment, twelve participants used these two BCIs to answer yes or no questions. Each participant completed four sessions, comprising two offline training sessions and two online sessions, one for testing each of the BCIs. With a support vector machine and a combination of spectral and time-frequency features, an average accuracy of 75.9%±11.4 was reached across participants in the online classification of no versus rest, with 10 out of 12 participants surpassing the chance level (60.0% for p<0.05). The online classification of yes versus no yielded an average accuracy of 69.3%±14.1, with eight participants exceeding the chance level. Task-specific changes in EEG beta and gamma power in language-related brain areas tended to provide discriminatory information. Embodiments can enable online EEG and/or fNIRS classification of covert speech. These are examples to support covert speech as a BCI activation task.

Embodiments described herein can provide more intuitive BCIs for communication. The BCI can provide communication capabilities for individuals who present as locked-in and hence are unable to communicate conventionally. However, some BCIs use non-intuitive mental tasks such as motor imagery, mental arithmetic, or mental reaction to external stimuli to make a selection. These control schemes can be difficult to perform by the target population and may have little or no correlation with typical communication methods. Further, while motor-based tasks can be intuitive for BCI control of a robotic arm or a wheelchair, motor imagery can be difficult or impossible for individuals with congenital or long-term motor impairments. An intuitive mental task for BCI-based communication is covert speech, also known as imagined speech or speech imagery in brain studies. Embodiments described herein can implement online classification of covert speech based on electroencephalography (EEG) signals and/or fNIRS signals.

Embodiments described herein can help non-verbal users for the following example applications: communication with healthcare providers, home care and daily interactions (e.g., express preferences, make choices); healthcare (e.g., link to devices or wheelchair); Smart Home control (e.g., lights on/off) and other daily functions; Gaming and entertainment (e.g., navigation and control); and so on.

Positron emission tomography (PET) and functional magnetic resonance imaging (fMRI) techniques can decode brain waves arising from covert speech, which can lead to the identification of brain areas involved in covert and overt speech. Other brain signal recording modalities in which simultaneous measurements of EEG and magnetoencephalography (MEG) can be used to detect covert articulation of different words.

Embodiments described herein can classify different covert speech tasks using EEG. EEG measurements can be acquired during speech imagery of languages, such as the English vowels /a/ and /u/, for example, and the data can be analyzed offline. Participants can be instructed to imagine mouth opening and lip rounding for the /a/ and /u/ vowels, respectively. As an example, an offline average accuracy of 62.7±8.3% may be reached across three participants when comparing two vowels.

Other attempts can investigate EEG-based classification of covert speech tasks for larger units of language such as syllables. Participants can be asked to mentally repeat two English syllables, "ba" and "ku", with different rhythms. After offline analysis of the data, an average classification accuracy of 61% ("ba" versus "ku" trials) can be achieved for seven participants.

Embodiments can use EEG to classify complete and meaningful words, including English and non-English words. For instance, there can be a classification of EEG signals during covert speech of two Chinese monosyllabic characters ("one" and "left" in English), reaching an offline accuracy of 66.9% across eight participants who are fluent Chinese speakers.

Classification accuracies in EEG studies on covert speech, even in binary cases, could be less than 70%, an example minimum threshold for practical BCI use. However, it should be noted that other covert speech EEG studies may not deploy an online paradigm. Closing the BCI loop by providing feedback may facilitate the modulation of a user's neuronal network over time and possibly enhance BCI performance. Moreover, while EEG may not be reliable enough to decode covert articulation of complicated sentences, it may be sufficiently reliable to discern between simple and frequently used words such as "yes" and "no". If such was achievable, one could design a highly intuitive BCI that would enable nonverbal individuals with severe motor impairments to direct their own care, express preference, and make choices. Two "yes" versus "no" covert speech offline BCIs can be tested with both non-disabled and locked-in participants using functional near-infrared spectroscopy (fNIRS) and can achieve an offline average classification accuracy of approximately 76% (~76%) across participants in both studies (10 non-disabled and one locked-in participant). This optical brain imaging modality measures the vascular response associated with brain activation and thus generally requires longer recordings than EEG. As such, fNIRS offers a lower communication rate than EEG. For instance, the duration of each mental task in some fNIRS studies can be 25 s. In contrast, the task duration can be less than 10 s in some EEG studies.

Embodiments described herein can implement online EEG-based BCIs. An example can detect covert repetition of "no" and unconstrained rest, and another example can differentiate between the imagined articulation of "yes" and "no". Embodiments enable real-time classification of EEG signals arising from covert speech.

Embodiments described herein can implement online fNIRS-based BCIs. An example shows an fNIRS-BCI for online 3-class classification of the following three tasks: thinking "yes" while mentally rehearse the phrase "yes", thinking "no" while mentally rehearse the phrase "no", and unconditional rest. I.e., a 3-class BCI based on covert speech using a portable and non-invasive neuroimaging technique, e.g. EEG or fNIRS. Embodiments described herein classification of more than two classes or covert speech using brain-computer interfaces (BCIs), such as no, yes, and rest classes, for example.

FIG. 1 is a view of an example brain-computer interface (BCI) system 100, in accordance with some embodiments. BCI system 100 includes BCI platform 110, which includes classification device 120. BCI platform 110 connects to interface application 130, for example, to gather EEG data, fNIRS data or other data from a user engaged with interface application 130. The data gathered or a modification of the data gathered may encode communication or input (such as EEG signals, fNIRS signals or other readings denoting brain activity) from individuals who present as locked-in and are hence unable to communicate conventionally. The interface application 130 can include electrodes to generate EEG signals and/or fNIRS signals. Interface application 130 can include other sensors, for example. Interface application 130 and BCI platform 110 can receive other types of data, including imaging data, for example. Interface application 130 can include one or more clocks to synchronize data collected from different sensors and modalities.

BCI platform 110 can connect to interface application 130 to cause one or more questions to be presented to a user engaged at interface application 130 and to receive one or more responses to questions or other data input from the user. The questions can be presented on a display device using an interface generated by interface application 130. The questions can be presented by way of an audio signal and speaker, as another example. BCI platform 110 can organize the received data or aggregate the data with other data. For example, data from a question and answer exchange with a user can be used by BCI platform 110 to verify collected EEG data and/or fNIRS data encoding the user's covert speech. BCI platform 110 can organize the received data or aggregate the data with other data using time stamps and clock data for synchronization.

Interface application 130 can engage a user, for example, via electrodes and/or NIR emitters and photodetectors strategically placed on the user's scalp corresponding to brain regions providing discriminative information or showing task-based activation, such as data corresponding to covert speech. In some embodiments, the electrodes may form part of a headset that is engaged with a BCI platform 110, or houses a BCI platform 110. The headset can additionally process data. Interface application 130 can also engage a user via a display, interactive display, keyboard, mouse, or other sensory apparatus. Interface application 130 can transmit and receive signals or data from such devices and cause data to be sent to BCI platform 110.

In some embodiments, interface application 130 can process data before sending the data via network 140 and/or to BCI platform 110. A user can be engaged with interface application 130 via electrodes or a headset. In some embodiments, BCI platform 110 and/or classification device 120 can be housed in the headset or other means of engagement with interface application 130. In some embodiments, BCI platform 110 and/or classification device 120 can connect to interface application 130 over a network 140 (or multiple networks).

Classification device 120 associated with BCI platform 110 can receive sensor data, for example, EEG data and/or fNIRS data from a single user via interface application 130. Classification device 120 can receive stored data from one or more external systems 150 or interface applications 130, such as data corresponding to other sessions of data collection, for example. Classification device 120 can build or train a classification model using this data, for example, EEG data and/or fNIRS data from a single user. Classification device 120 can use the classifier to classify covert speech of the user and cause a result to be sent to an entity 150 or interface application 130. The result can cause an entity to actuate a response, which can be an alert to a caregiver, or data for a researcher.

The classifier can be re-trained on additional EEG data and/or additional fNIRS data, for example, data collected from the user at a more contemporaneous time. This may improve the accuracy of the classifier, for example, if same session data are more relevant than data collect from previous days. Further, additional data may improve the accuracy of the classifier so it can be continuously updated and trained as more data and feedback is provided to the BCI platform 110.

BCI platform 110 can connect to interface application 130 via a network 140 (or multiple networks). Network 140 (or multiple networks) is capable of carrying data and can involve wired connections, wireless connections, or a combination thereof. Network 140 may involve different network communication technologies, standards and protocols, for example.

In some embodiments, external systems 150 can connect to BCI platform 110 and/or classification device 120, for example, via network 140 (or multiple networks). External systems 150 can be one or more databases or data sources or one or more entities that aggregate or process data. For example, an external system 150 can be a second BCI platform 110 that collects EEG data and/or fNIRS data (or other data), performs feature extraction on the data, and builds a classification model. The external system 150 can then process the data and/or build one or more classification models based on a selection of features. The one or more classification models can be used by one or more other BCI platforms 110, stored in a database, and/or transmitted to an external system 150, for example, that is accessible by researchers or developers.

External systems 150 can receive data from an interface application 130, BCI platform 110, and/or classification device 120. This data can include raw data collected by interface application 130, such as EEG data from electrodes (and/or fNIRS data from emitters and photodetectors) placed on a user's scalp, data processed by interface application 130, BCI platform 110, and/or classification device 120 (including a classification device 120 housed in a headset associated with electrodes (and/or emitters and photodetectors) placed on a user's scalp), and/or data from one or more other external systems 150. This connectivity can facilitate the viewing, manipulation, and/or analysis of the data by a researcher, developer, and/or healthcare provider engaged with an external system 150.

Figure 2:
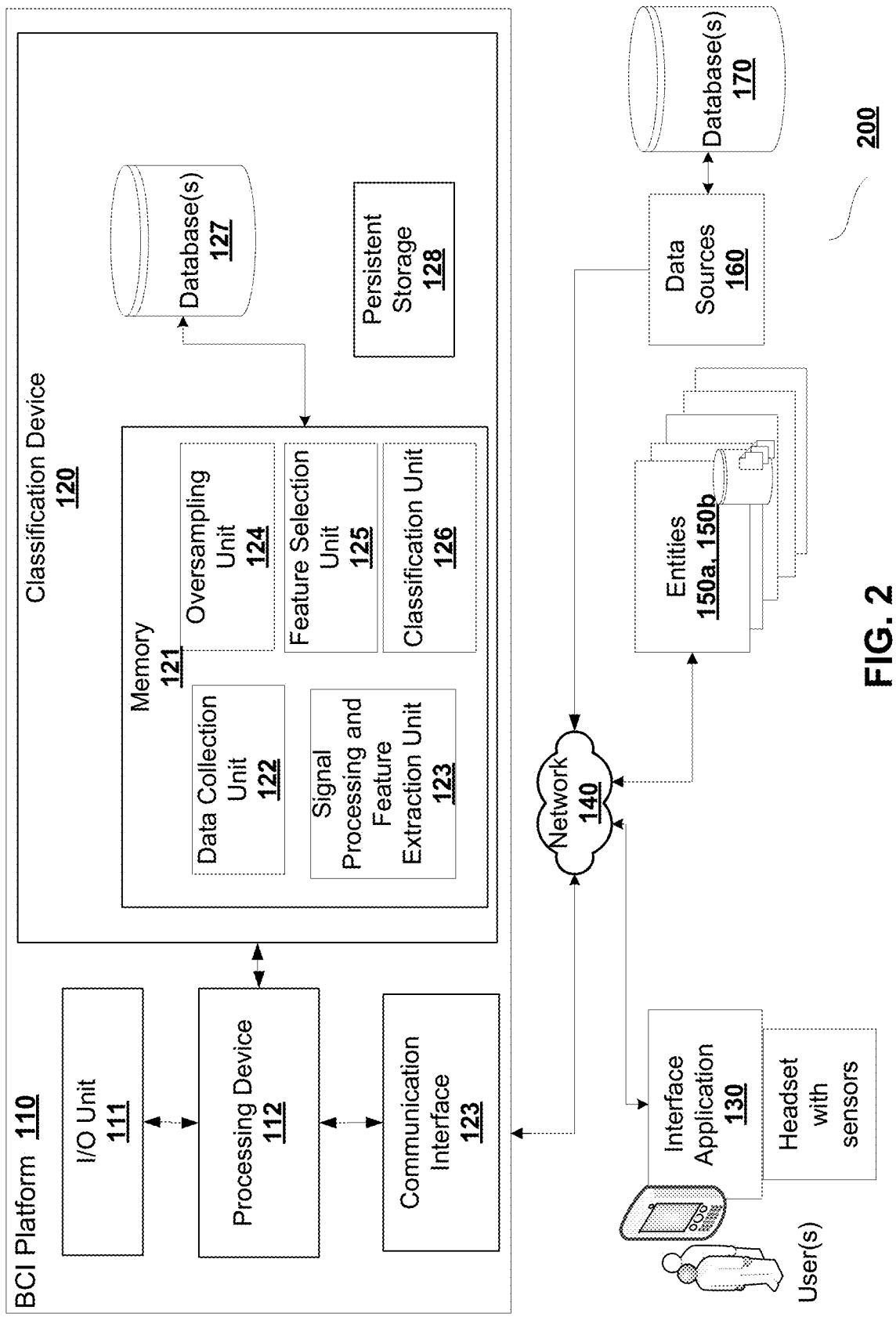
FIG. 2 is a view of an example BCI platform and classification device, in accordance with some embodiments.

FIG. 2 is a view of an example BCI platform 110 and classification device 120 according to some embodiments. A BCI platform 110 can include an I/O Unit 111, processing device 112, communication interface 123, and classification device 120.

A BCI platform 110 can connect with one or more interface applications 130, entities 150, data sources 160, and/or databases 170. This connection may be over a network 140 (or multiple networks). BCI platform 110 receives and transmits data from one or more of these via I/O unit 111. When data is received, I/O unit 111 transmits the data to processing device 112.

Each I/O unit 111 can enable the BCI platform 110 to interconnect with one or more input devices, such as a keyboard, mouse, camera, touch screen and a microphone, and/or with one or more output devices such as a display screen and a speaker.

A processing device 112 can execute instructions in memory 121 to configure classification device 120, and more particularly, data collection unit 122, signal processing and feature extraction unit 123, oversampling unit 124, feature selection unit 125, and classification unit 126. A processing device 112 can be, for example, any type of general-purpose microprocessor or microcontroller, a digital signal processing (DSP) processor, an integrated circuit, a field programmable gate array (FPGA), a reconfigurable processor, or any combination thereof. The oversampling is optional and in some embodiments there may not be an oversampling unit.

Memory 121 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Storage devices 120 can include memory 121, databases 127, and persistent storage 128.

Each communication interface 123 can enable the BCI platform 110 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g., Wi-Fi, WiMAX), SS7 signaling network, fixed line, local area network, wide area network, and others, including any combination of these.

The BCI platform 110 can be operable to register and authenticate users (using a login, unique identifier, and password for example) prior to providing access to applications, a local network, network resources, other networks and network security devices. The platform 110 may serve one user or multiple users.

The storage 127 may be configured to store information associated with or created by the classification device 120. Storage 127 and/or persistent storage 128 may be provided using various types of storage technologies, such as solid state drives, hard disk drives, flash memory, and may be stored in various formats, such as relational databases, non-relational databases, flat files, spreadsheets, extended markup files, etc.

Classification device 120 can be used to build a classification model by training on data received from interface application 130 or other entities 150, for example, EEG data and/or fNIRS data collected during covert speech of a user. Data collection unit 122 associated with a classification device 120 and BCI platform 110 can receive data, for example, EEG data and/or fNIRS data from a single user via interface application 130. Data collection unit 122 can receive stored data from one or more external systems 150 or interface applications 130, for example, corresponding to other sessions of data collection.

Signal processing and feature extraction unit 123 associated with a classification device 120 can process the data or EEG signals and/or fNIRS signals, for example, to remove linear trends, electrical noise, and EOG artifacts, and can reconstruct the EEG signal from the remaining components.

Signal processing and feature extraction unit 123 can extract features from the data or EEG data and/or fNIRS data using one or more feature extraction methods, such as common spatial pattern, matched-filtering, spectral power estimates, or autoRegressive (Yule-Walker) model of order of magnitude, e.g., three, or wavelet transform (db4). This can produce a vector of features. The order of magnitude can vary (i.e., two or more).

Oversampling unit 124 can sample the data or EEG data and/or fNIRS data, for example, to oversample data collected at a more contemporaneous time. In some embodiments, cost-sensitive classification can be used to give the more contemporaneous data larger coefficients in the cost function compared to data collected on, for example, a previous day. Oversampling unit 124 can thus facilitate higher classification accuracies, for example, by oversampling data collected from the same session that the classification model once built will be used to classify EEG data and/or fNIRS data from. The oversampling is optional, and in some embodiments there may not be an oversampling step.

Feature selection unit 125 can select features from the features extracted from the data or EEG data and/or fNIRS data. This may help reduce or avoid overfitting the data, facilitate the generalizability of the data, or facilitate the applicability of a classifier modelled on the data or features extracted from the data. In some embodiments, a classification model is trained on data or features selected from a single user, for example, the ten best features extracted from a set of features extracted from the data collected from the user. The features may be selected based on how they relate to accuracy of the resulting classification model or lowest error.

Classification unit 126 associated with the classification device 120 can use the selected features to train an algorithm, such as a linear support vector machine. The algorithm can be used for machine learning classification of data to facilitate classification of covert speech given EEG data and/or fNIRS data as input. For example, BCI platform 110 can use EEG data and/or fNIRS data to build a support vector machine classification model for a particular user who was or is engaged with interface application 130. The classifier can be re-trained on additional EEG data and/or fNIRS data, for example, data collected from the user at a more contemporaneous time. This may improve the accuracy of the classifier, for example, if same session data are more valuable than data collect from previous days.

At a later time or at a time immediately following re-training of the classifier, interface application 130 can receive EEG data and/or fNIRS data from the user, for example, corresponding to the user's covert speech, that is, imagining a word or words, such as "no". Interface application 130 can transmit the data to BCI platform 110. As described above, data collection unit 122 can collect the EEG data and/or fNIRS data, signal processing and feature extraction unit 123 can process the data and extract features, feature selection unit 125 can select the relevant subset of features, and classification unit 126 can use the personalized classification model for that user to help determine the user's covert speech, that is, the imagined word or words. An example classification model can be a support vector machine classification model. The determination can be processed and/or presented to a user via interface application 130 or transmitted to an external system 150, for example, a device or system accessible by a caregiver or researcher.

Figure 3:
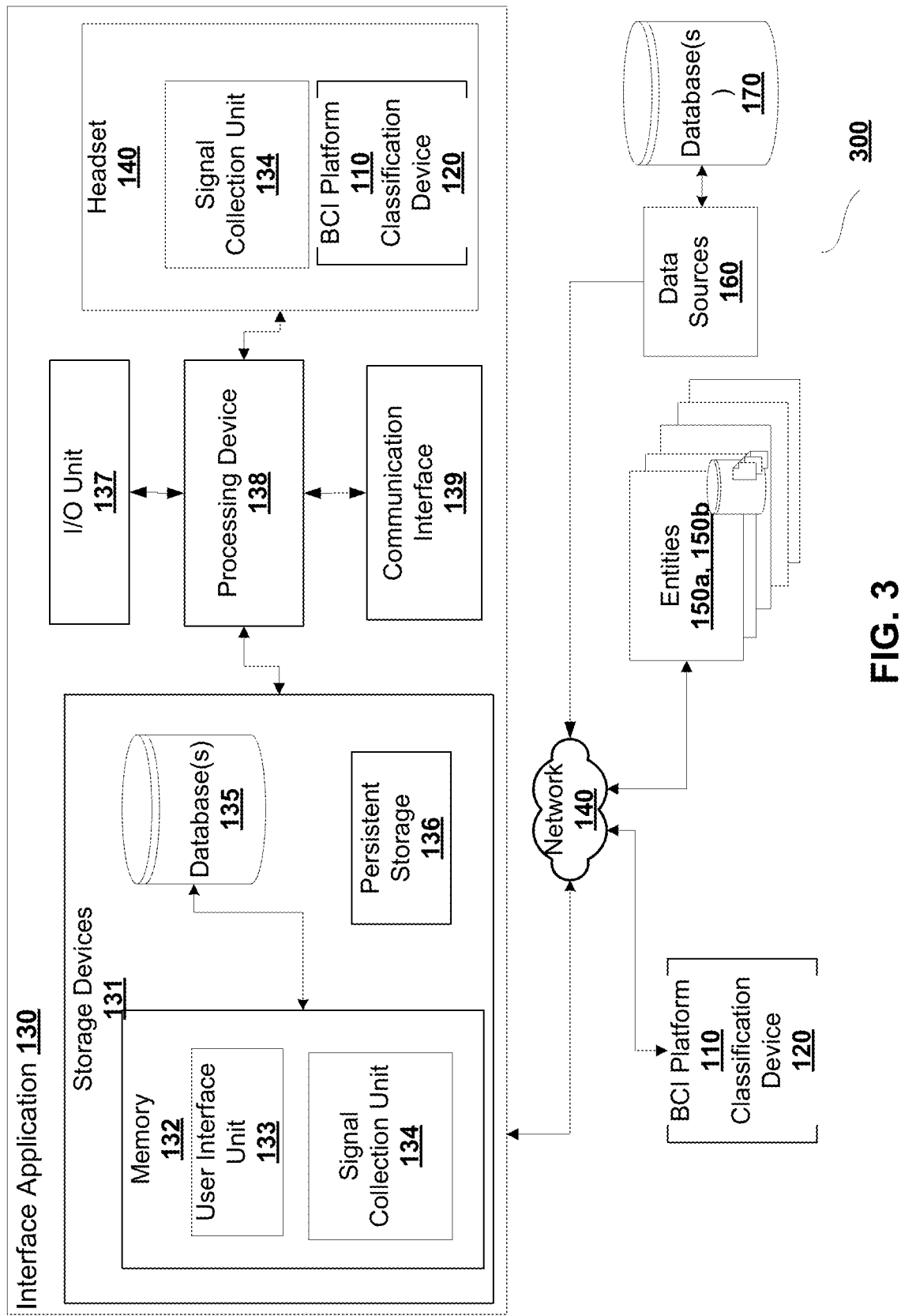
FIG. 3 is a view of an example interface application, in accordance with some embodiments.

FIG. 3 is a view of an example interface application 130. In some embodiments, interface application 130 includes a classification device 120. In some embodiments, interface application 130 is connected to a headset associated with or housing a BCI platform 110 and classification device 120. The headset may include multiple electrodes to collect EEG data (and/or multiple emitters and photodetectors to collect fNIRS data) when connected to a user's scalp. The signals may be collected by signal collection unit 134, which may connect to BCI platform 110 housed within the headset. The BCI platform 110 can create and/or use one or more classifiers as described above. For example, the BCI platform 110 within a headset 140 can train and retrain a classifier using EEG data and/or fNIRS data from one or more sessions from a single user engaged with interface application 130 or headset 140. BCI platform 110 can use the classifier to classify covert speech from the user using further EEG signals. BCI platform 110 may be operable as described above.

In some embodiments, signal collection unit 134 may be associated with an interface application 130 that does not include a headset 140. Signal collection unit 134 can gather data, for example EEG data and/or fNIRS data, from a user engaged with interface application 130. Interface application 130 can then cause transmission of data, the EEG signals and/or fNIRS signals, processed data or processed EEG signals and/or processed fNIRS signals, or other information to a BCI platform 110 and/or classification device 120 over a network 140 (or multiple networks). The BCI platform 110 can train and retrain a classifier using EEG data and/or fNIRS data from one or more sessions from a single user engaged with interface application 130 or headset 140. BCI platform 110 can use the classifier to classify covert speech from the user using further EEG signals and/or fNIRS signals. BCI platform 110 may be operable as described above.

In some embodiments, interface application 130 connects to a BCI platform 110 and classification device 120 over a network 140 (or multiple networks).

Each I/O unit 137 enables the interface application 130 (including headset 140) to interconnect with one or more input devices, such as a keyboard, mouse, camera, touch screen, microphone, electrodes, headset, or other sensory collection devices, for example, that can detect brain activity or covert speech. Each I/O unit 137 also enables the interface application 130 (including headset 140) to interconnect with one or more output devices such as a display screen, speaker, or other devices presenting visuals, haptics, or audio.

A processing device 138 can execute instructions in memory 132 to configure user interface unit 133 and signal collection unit 134. A processing device 138 can be, for example, any type of general-purpose microprocessor or microcontroller, a digital signal processing (DSP) processor, an integrated circuit, a field programmable gate array (FPGA), a reconfigurable processor, or any combination thereof.

Memory 132 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Storage devices 131 can include memory 132, databases 135, and persistent storage 136.

Each communication interface 139 can enable the interface application 130 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g., Wi-Fi, WiMAX), SS7 signaling network, fixed line, local area network, wide area network, and others, including any combination of these.

The interface application 130 can be operable to register and authenticate users (using a login, unique identifier, and password for example) prior to providing access to applications, a local network, network resources, other networks and network security devices. The platform 110 may serve one user or multiple users.

The database 135 may be configured to store information associated with or created by the classification device 120. Database 135 and/or persistent storage 136 may be provided using various types of storage technologies, such as solid state drives, hard disk drives, flash memory, and may be stored in various formats, such as relational databases, non-relational databases, flat files, spreadsheets, extended markup files, and so on.

User interface unit 133 can manage the dynamic presentation, receipt, and manipulation of data, such as for example, input received from interface application 130. For example, user interface unit 133 can cause a question such as "Are you in pain?" to be presented to the user via a display. The question may be selected dynamically in response to data received from the user via interface application 130 or otherwise. User interface unit 133 can associate the response from the user, for example, gathered by a signal collection unit 134 and classified by a BCI platform 110, as a response and cause storage of same in storage devices 131 or transmission of same over network 140 (or multiple networks). As another example, user interface unit 133 can facilitate validation of a user response with the result determined by a BCI platform 110 or classifier. User interface unit 133 can present the user with a prompt, for example, visual, audio, or haptic, to verify covert speech. The interface application 130 can gather the response via I/O unit 137 connected to a keyboard, touchscreen, mouse, microphone, or other sensory device. User interface unit 133 can associate the response with the result determined by a BCI platform 110 or classifier to verify the accuracy of the BCI platform 110 or classifier. In some embodiments, interface application 130 can transmit the response to a BCI platform 110, which can associate the response with the result determined by the BCI platform 110 or classifier to verify the accuracy of the BCI platform 110 or classifier.

Applications of some embodiments may assist or facilitate non-verbal users. Applications may help non-verbal users or others with the following: communication with healthcare providers, home care and daily interactions (express preferences, make choices); healthcare (link to devices or wheelchair); Smart Home control (e.g., lights on/off) and other daily functions; gaming and entertainment (navigation and control).

Applications of some embodiments may enable or facilitate activating a switch by covert word repetition (e.g., Help vs resting), expressing a choice (yes/no), or expanding covert speech task to include other words (e.g. left/right, stop/go).

EEG

Example embodiments were tested using an example experiment using EEG. Participants in an example experiment included twelve able-bodied individuals (six male) between the ages of 24 and 33 (mean age: 27.6±3.2 years). Participants had normal, or corrected-to-normal vision, were fluent in English and had no reported history of neurological disorders. Participants were asked to refrain from drinking caffeinated or alcoholic beverages at least three hours prior to each session.

EEG signals were recorded from 64 active electrodes, placed over the entire scalp using the International 10-10 system, using a BrainAmp DC amplifier (Brain Products GmbH, Germany). The sampling rate was 1 kHz and impedances were kept below 10 kΩ. The ground and reference electrodes were positioned at AFz and FCz, respectively. Fp1 and Fp2 electrodes were only used to remove electrooculography (EOG) artifacts.

The words "yes" and "no" were selected for the covert speech task. These words can afford an intuitive response to questions of care, such as: "Are you in pain?", "Are you hungry?", "Do you need to use the restroom?". These words may also afford a binary switch for choice-making. From a phonetic perspective, the beginning consonants of these two words, /y/ in "yes" and /n/ in "no" have different places and manners of articulation, a difference that other covert speech studies have reliably detected using electrocorticography and EEG. Moreover, the vowels in these two words, /e/ in "yes" and /o/ in "no" are articulated using different locations of the tongue which can elicit different neuronal patterns in motor and premotor regions even in the absence of overt articulation of these words. This may be articulated using the near-front region of the tongue while /o/ is articulated using the back of the tongue.

Participants attended four sessions on four separate days. The first two sessions were training sessions in which no real-time feedback was provided (offline). In each of the training sessions, participants performed 90 trials, including 60 yes versus no questions (henceforth referred to as "covert speech trials") and 30 unconstrained rest trials. The trials were presented in pseudorandom order such that equal numbers of yes and no responses were acquired.

Each trial started with a fixation cross at the center of a blank screen. The fixation cross persisted throughout the trial. In the covert speech trials, participants were asked to answer a perceptual yes versus no question by iteratively repeating the answer ("yes" or "no") mentally without any vocalization or motor movement, especially of the lips, tongue or jaw. A question appeared on the screen for four seconds at the beginning of each trial and was replaced by the instruction, "start answering", which disappeared after one second. Participants were told to commence covert speech as soon as the instruction vanished. The question was always the same, "Is this word in uppercase letters?", with a different word in every trial. Words were printed in lowercase for half of the covert speech trials. Hence, the 60 covert speech trials were distributed equally between "yes" and "no" trials. All words were neutral in valence to minimize elicitation of affective responses.

In the remaining trials, i.e., the "rest" trials, participants allowed normal thought processes to occur without restriction. In these trials, a "rest" message appeared on the screen for four seconds at the beginning of the trial, followed by a one second "start" instruction. Participants were told to commence unconstrained rest immediately following this instruction.

The classification of the question-induced electrical brain activity, prior to the covert speech or unconstrained rest periods, yielded chance-level results, which may confirm that question presentation alone did not elicit differential activation between yes and no trials. The duration of the mental task in each trial was 11 s, regardless of the trial type. However, data from the first one second of each trial was removed from analysis since any reactive brain signal to the visual cue (appearance and disappearance of the start instruction) at the beginning of trial was not of interest.

At the end of each trial, participants were asked to verify their response by clicking on one of the possible answers (no, yes, or rest). They also had the option of choosing "I could not perform the task properly". If the case of choosing this option, or if the verified response did not match the correct response, the trial was discarded. EEG data were not recorded during post-trial response verification.

Figure 5:
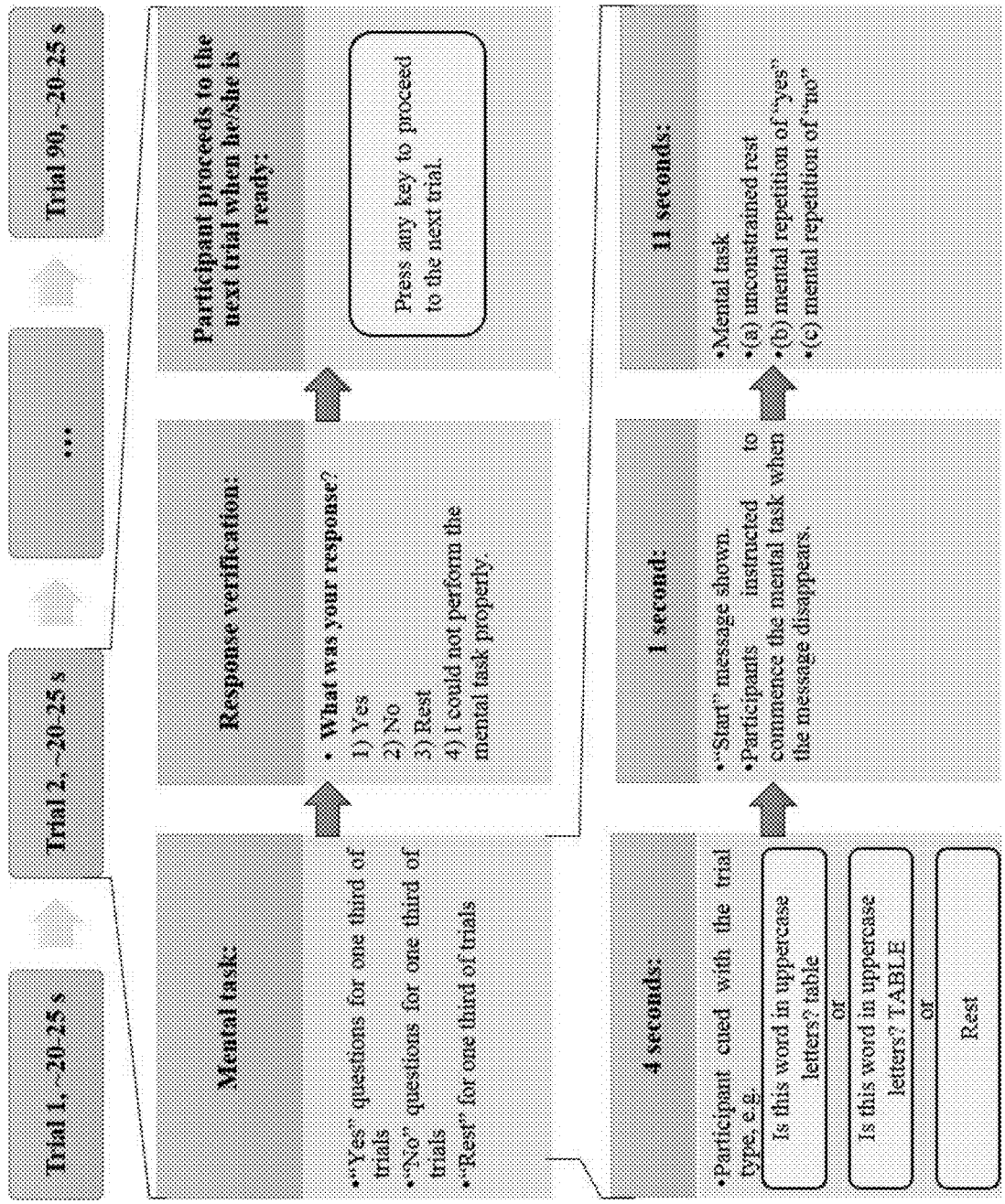
FIG. 5 is a view of an example timing diagram for offline sessions, in accordance with some embodiments.

Over the two training sessions for each participant (first two sessions for each participant), 180 trials (10 s each) were acquired. These trials were distributed equally between yes, no and unconstrained rest. On average, less than three trials across the two training sessions for each participant were discarded due to the inconsistency between the trial type and the verified response of the participant at the end of the trial. The timing diagram for the offline sessions is portrayed in FIG. 5. Diagram 500 illustrates the timing of the offline sessions.

Each of the remaining online sessions (last two sessions for each participant) was designed to test one of the 2-class BCIs: "no" versus "rest" in the first online session and "yes" versus "no" in the second online session.

The first online session ("no" versus "rest") consisted of three blocks, starting with an offline block (40 trials, 20 from each class), followed by two online blocks (40 trials each). During the online blocks, participants were presented with the classifier decision subsequent to each trial. The aim of using an offline block in each test session can be to provide within-session training data.

Figure 6:
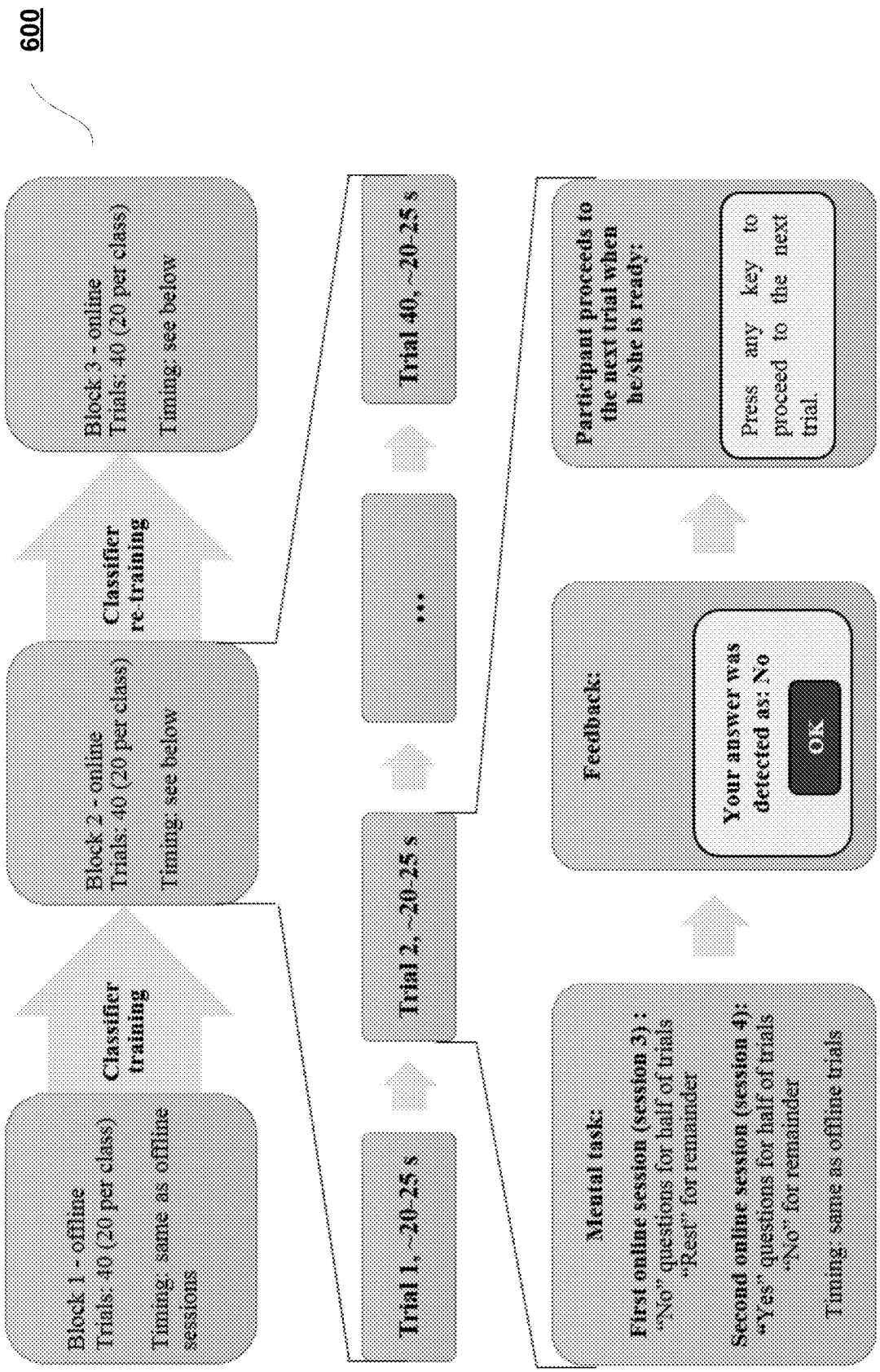
FIG. 6 is a view of an example timing diagram for online sessions, in accordance with some embodiments.

The second online session resembled the first, but the BCI classified between "yes" and "no". The timing diagram for the online sessions is depicted in FIG. 6. Diagram 600 illustrates the timing of the online sessions.

In the first online session, "no" over "yes" can be chosen because, for example, the no versus rest classifiers may reach a higher average accuracy during the offline sessions. Also, the presence of a nasal consonant (/n/ in this case) may be detected in both covert and overt speech using EEG.

Data Analysis

The data collection for the test (online) sessions started after the end of the two training sessions for all 12 participants. Various feature extraction techniques, feature selection algorithms and classification models with different hyper-parameters can be tested on the data from the training sessions with 10-fold cross validation (CV). In some embodiments, the cross validation may be K-fold, where K is determined by the amount of data available (i.e., sample size dependent). For example, K may depend on the number of features (e.g., a K-fold CV folds into K subsets, where within each subset, the number of data points is preferably approximately ten times the number of features). The models and hyper-parameters which yielded the lowest mean CV error for the binary classification problems of "no" versus "rest" and "yes" versus "no" may be chosen for use in the test sessions. These models and parameters are introduced later in this section.

During each test session, at the end of the offline block, the accepted trials from the training sessions (~60 trials per class), along with the trials from the offline block of the test session (20 trials per class), can be processed and used to build a 2-class classification model. This classifier can be used for online classification of a subsequent or first online block. Participants received visual feedback after each trial (see FIG. 6).

Figure 4:
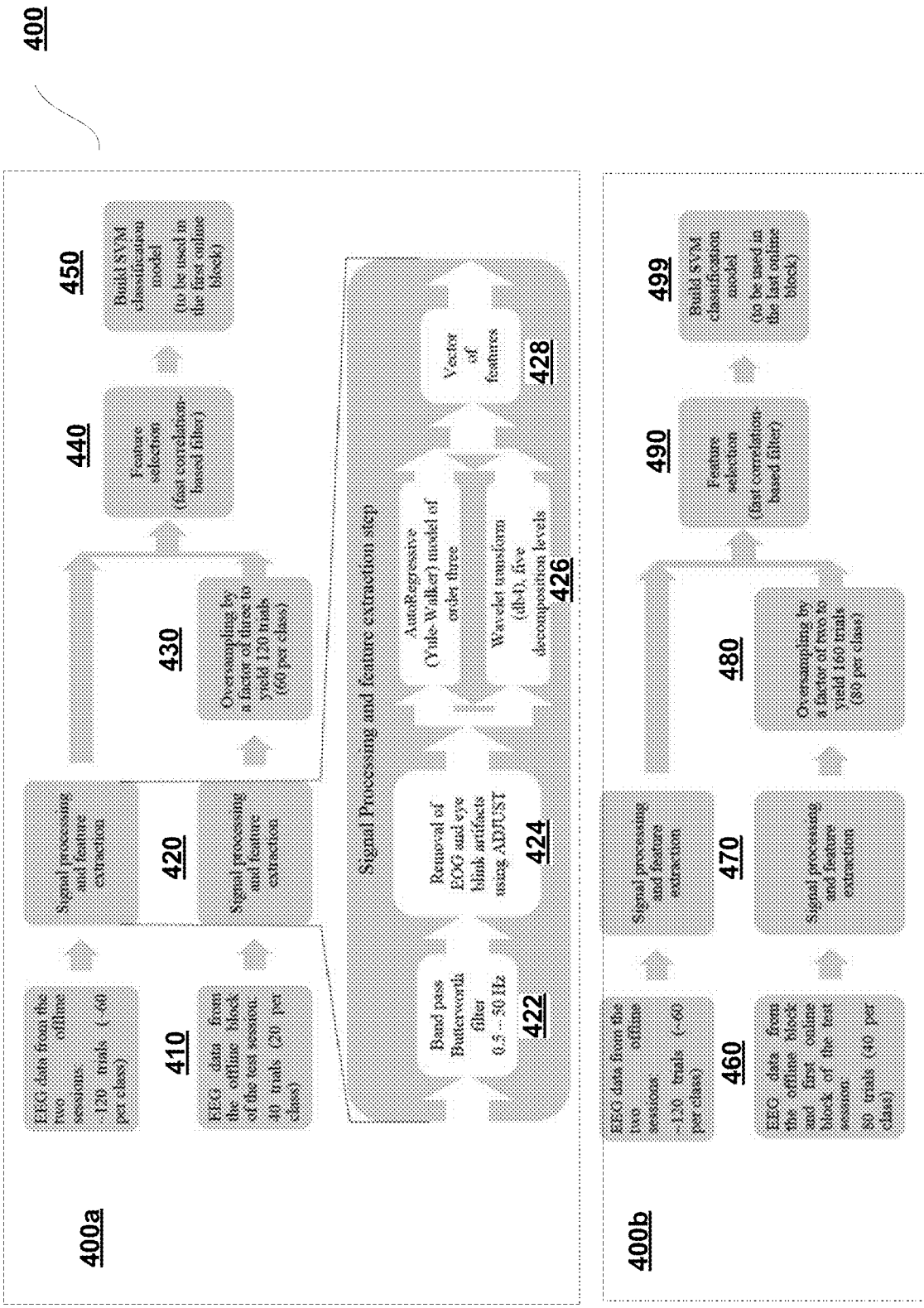
FIG. 4 is a view of an example workflow for building classifiers, in accordance with some embodiments.

At the end of the first online block, the trials from this block (40 trials, 20 per class) can be added to the previous dataset and the classifier was again re-trained. The updated classifier can then be deployed in the second online block to provide online feedback. The analytical steps for building the classifiers are elaborated in the following and summarized in FIG. 4. Flowchart 400 illustrates example workflow for building a classification model to be used in the first online block (the steps illustrated in 400*a*) and the second online block (the steps illustrated in 400*b*). The values referred to are examples.

It should be noted that these steps can be followed in both online sessions. A difference may be that the first online session is devoted to the no versus rest classification problem while the second can evaluate the discrimination between yes and no trials. The values described, for example, for the number of decomposition levels at 426, the order of the model at 426, the oversampling factor at 430 and at 480, and the filter's cut off frequencies at 422, are not fixed and can be varied in embodiments. This is an example.

At 410, EEG data from the two offline sessions as well as from the offline block of the test session is gathered.

At 420, signal procession and feature extraction is performed. For example, at 422, a 0.5-50 Hz bandpass Butterworth filter can be applied. In some embodiments, frequencies higher than 50 Hz may be used. At 424, EOG artifacts can be removed, including horizontal and vertical eye movements and eye blinks. The EEG signal can be reconstructed from the remaining independent components. At 426, autoregressive (AR) coefficients and discrete wavelet transform (DWT) coefficients can be extracted as features. At 428, a vector of features can be produced.

At 430, oversampling of EEG data can be performed as described below.

At 440, features can be selected for building a classification model.

At 450, a classification model is built. This can be used in the first online block.

At 460, EEG data from the two offline sessions as well as from the first online block of the test session is gathered.

At 470, signal procession and feature extraction is performed.

At 480, oversampling of EEG data can be performed as described below.

At 490, features can be selected for building a classification model.

At 499, a classification model is built. This can be used in the last online block.

Oversampling

At the end of the offline block of each test session, a 2-class classification model can be trained using an augmented training set, consisting of data from the two offline sessions and the offline block of the current test session. The number of samples from the offline session (previous days' session) was ~120 trials (maximum 60 trials from each class) while the number of trials from the same session was about 40 trials. For training a BCI classifier, same session data may be more valuable than data collected from previous days. In order to compensate for the smaller number of same day samples, those trials were oversampled by a factor of three. This oversampling factor may help balance the sample sizes from the same and previous days and yield the highest online classification accuracies during pilot sessions. Other alternatives to oversampling, such as cost-sensitive classification, in which same day samples would be given larger coefficients in the cost function compared to the samples from the offline sessions, could be used but oversampling may yield higher online accuracies.

At the end of the first online block, the classifier was re-trained. At this point, the augmented training set included 80 trials from the same session (the first two blocks) and again a maximum of 120 trials from the previous day. Thus, the oversampling factor for the same day data was reduced to two. The steps in some embodiments for updating the classifier after the offline phase and again after the first online block are summarized in FIG. 4 in 400*a* and 400*b*, respectively.

Signal Preprocessing

Acquired EEG data were first filtered using a 0.5-50 Hz bandpass Butterworth filter to remove linear trends and electrical noise (e.g., 60 Hz line noise). In some embodiments, higher or lower frequencies may be used. The independent component analysis-based ADJUST algorithm was used to remove EOG artifacts, including horizontal and vertical eye movements and eye blinks. As known in the art, the ADJUST algorithm decomposes a signal into independent components. Some of the components represent useful information, while others represent eye movement. Eye movement components can be identified due to a significant amplitude signature. The ADJUST algorithm discards the eye movement (EOG artifact) components. After the removal of artifact components, the EEG signal was reconstructed from the remaining independent components. The reconstructed, EOG artefact-free signals for each of the 62 electrodes were used for further analysis.

Feature Extraction

Two types of features were extracted from each 10s trial: autoregressive (AR) coefficients and discrete wavelet transform (DWT) coefficients. Other EEG feature extraction methods, including common spatial pattern, matched-filtering and spectral power estimates may also be used on the data from the training sessions. However, the combination of AR and DWT features, which can provide both time and frequency domain information, may yield better classification results and can be selected for the test sessions.

Autoregressive Components (AR)

An AR model can be used for extracting features of EEG time series. In an AR model, the variable of interest can be predicted using a linear combination of past values of the same variable. AR coefficients were estimated using the Yule-Walker equations. A 3rd-order AR model can be fitted to the 10 s time series from each of the 62 electrodes, and the coefficients can be used as features (see above for a justification of a 3rd-order model). Hence, from each trial, 186 coefficients were extracted (62 electrodes×3 AR coefficients).

Discrete Wavelet Transform (DWT)

DWT may be used for analyzing EEG data and in general, non-stationary signals, given that it can extract features relating to frequency-dependent signal characteristics and their evolution over time.

The Daubechies-4 wavelet (db4) can be used with five decomposition levels (see above for justification of the number of decomposition levels). In some embodiments, one or more decomposition levels may be used. The number of levels may be personalized via the hyper-parameter optimization process, where a level is selected that is the most discriminatory for the user/patient. The db4 wavelet can be used to analyze EEG signals. The root mean square (RMS) and standard deviation (SD) of DWT coefficients at each decomposition level were used as features for classification. Hence, a total of 744 DWT features were extracted from each trial: 62 electrodes×6 DWT coefficients (five detail coefficients and one approximation coefficient)×2 (SD and RMS). The five levels of detail coefficients represent, in reverse order, i.e. detail 5 to detail 1, the frequency ranges of [1.88,3.75), [3.75, 7.5), [7.5,15), [15,30), [30,60) Hz, while the approximation level coefficients roughly represent the frequency range of less than 1.88 Hz. Note that prior to the extract of DWT coefficients, the signal has already been bandpass filtered between 0.5 and 50 Hz.

Feature Selection

A total of 930 features (186 AR features+744 DWT features) were extracted from each trial. Using all these features to model a classifier while having ~80 trials from each class (~60 trials from the training sessions and 20 trials from the offline block of the test session) may result in problems such as overfitting. Hence, a feature selection step can be used before building the classification model.

A filter method of feature selection, namely, a fast correlation-based filter (FCBF), can be used given its computational efficiency and frequent deployment. FCBF can choose the best features based on their symmetrical uncertainty (i.e., SU, a normalized variant of the mutual information) with the labels and other features.

For each participant, the 10 best features (out of 930 extracted features) were selected to build the classification model (similar to the selection of the AR model order and DWT decomposition level, see above for a justification of the feature dimensionality or why 10 was chosen). These features were not consistent across participants. In order to visualize the most important features, the topographic maps of symmetrical uncertainty (SU) between class labels and the different types of features at different electrode locations are shown in the results section.

Classification

The selected features from the previous step were used to train a linear support vector machine (SVM). This algorithm can have strong generalization performance and relatively fast training time.

Although SVMs support both linear and nonlinear classification, a linear SVM was used as may provide better accuracy on the training data (see above) compared to radial basis function kernel SVMs, sigmoid kernel SVMs, as well as other classification techniques, including regularized linear discriminant analysis, regularized logistic regression and naïve Bayes. It is also worth emphasizing that the feature selection and classification steps were performed for each participant separately. Hence, for each participant, a personalized classification model was built to calculate offline accuracies and for use in the online blocks. Some of the analytical steps can be summarized in FIG. 4.

Results

Online Accuracies

The online accuracies of the "no" versus "rest" and "yes" versus "no" sessions are shown in FIG. 7 by table 700. The upper limits of the 95% and 99% confidence intervals of the corresponding chance estimates were 60% and 65%, respectively. Average accuracies exceeding the upper limit of the 95% confidence interval of chance (i.e., 60%) are marked with an asterisk (*). Ten out of 12 participants surpassed this limit (60.0% for p<0.05) in the online no versus rest session while 8 out of 12 participants exceeded this limit in the online yes versus no session. Online classification accuracies are represented in "%" for each participant for the "no" versus "rest" and "yes" versus "no" online blocks.

Within a given session, the average accuracies of the second online block were ~11% and ~4.8% higher than those of the first online block for no versus rest and yes versus no classification problems, respectively. This improvement between blocks may be due to the classifier in the latter block having more training data, specifically from the same day.

Brain Regions Providing Discriminative Information

To highlight brain regions which exhibit task-specific patterns of activity, the SU between the extracted features and class labels were used. As stated above, FCBF can rank and choose features based on the same criterion.

Figure 8:
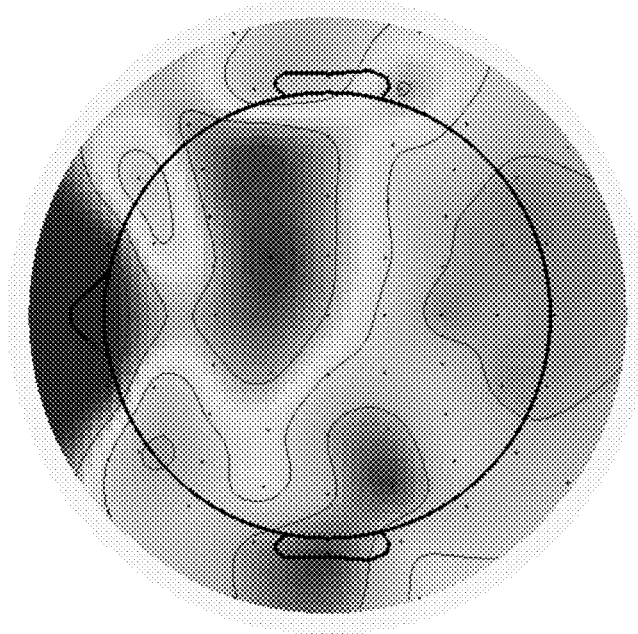
FIG. 8(a) is a view of an example average symmetrical uncertainty (SU) between the autoregressive (AR) features extracted from each channel and the class labels for the "no" versus "rest" BCI, in accordance with some embodiments.
FIG. 8(b) shows an example topographic map for a "yes" versus "no" BCI, in accordance with some embodiments.
Figure 8:
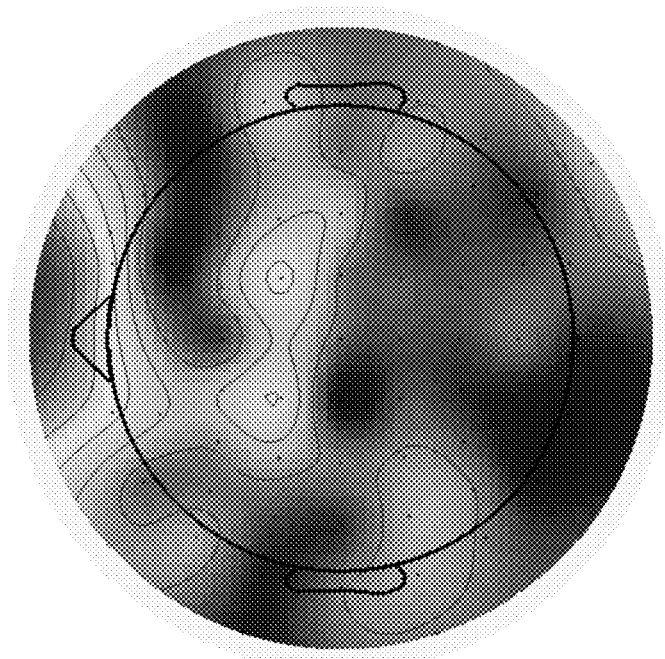

FIG. 8(a) portrays the average SU between the AR features extracted from each channel and the class labels for the "no" versus "rest" BCI. In this graph, the value assigned to each electrode is the grand average of SU across all three AR features extracted from that electrode and also across all participants. FIG. 8(b) shows the same topographic map for the "yes" versus "no" BCI. Only the online trials from the respective online session were considered in the generation of these maps.

As can be seen in these, for the "no" versus "rest" BCI, electrodes from the left temporal cortex (FT9 and FT7), motor regions (C1), prefrontal cortex (AF4, F6 and F8), parietal cortex (P1, PO7, PO3 and PO8) and the occipital region (PO9 and O1), exhibited task-specific temporal patterns of activity in most participants.

On the other hand, for the "yes" vs "no" BCI, a smaller number of electrodes provided relatively high SU with the two covert speech tasks. These channels were located in the left temporal cortex (CP5 which is approximately located over Wernicke's area, CP3, T7, FT9 and FT7) and the prefrontal cortex (AF7). The task of mentally repeating a word includes various brain functions, such as speech production, speech motor imagery and attention. Hence, when compared to unconstrained rest, covert speech revealed more discriminatory patterns across more brain regions. Likewise, the comparison between the two covert speech tasks yielded fewer differential brain patterns.

Figure 9:
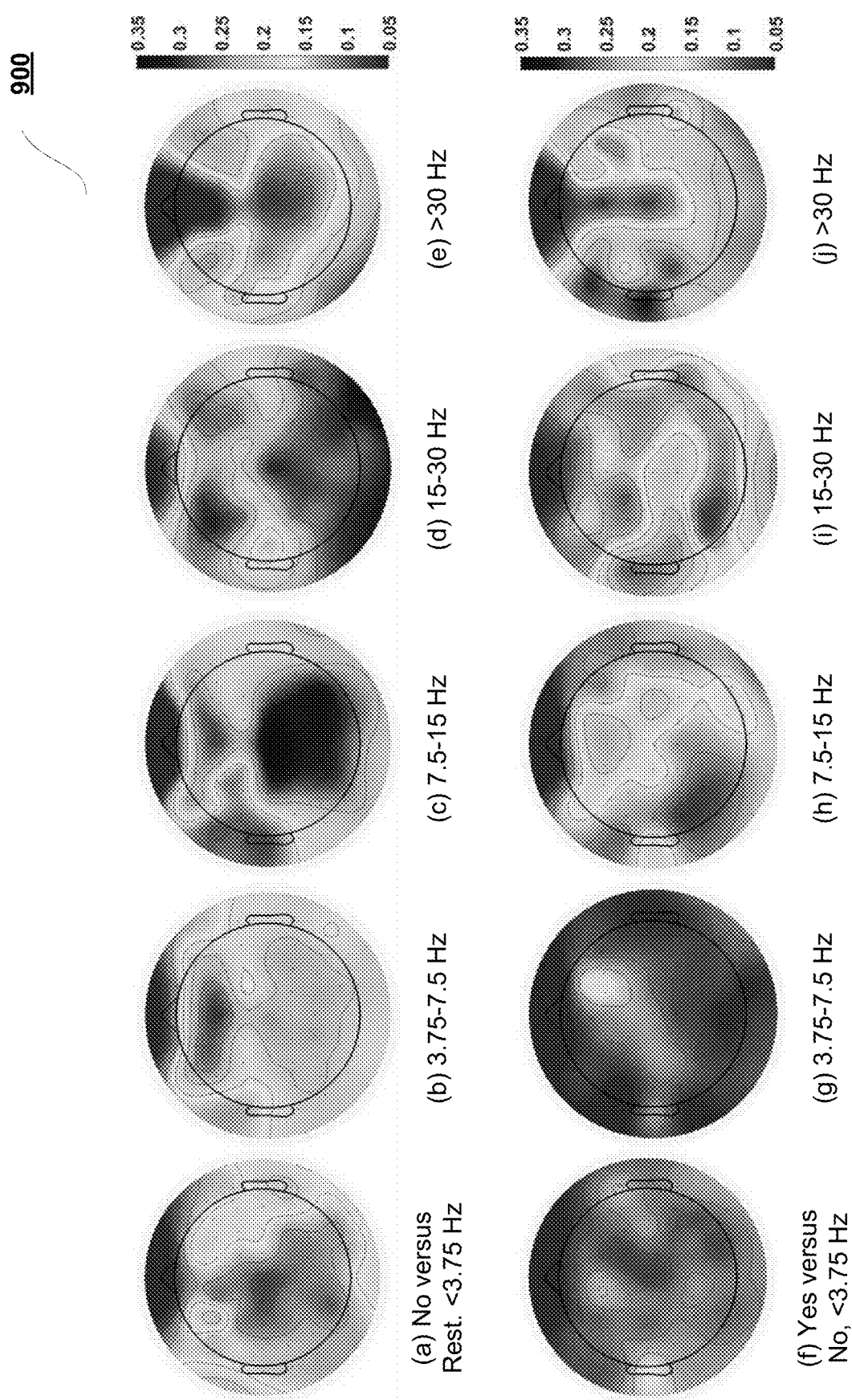
FIG. 9(a)-(e) show an example average SU between the discrete wavelet transform (DWT) features extracted from each channel and the class labels in five frequency ranges for "no" versus "rest" BCI, in accordance with some embodiments.
FIG. 9(f)-(j) show an example topographic maps for the "yes" versus "no" BCI, in accordance with some embodiments.

While the AR algorithm models the signal in the temporal domain, the DWT captures the features of the signal in different frequency ranges. FIG. 9(a)-(e) depicts the average SU between the DWT features extracted from each channel and the class labels in five frequency ranges for the "no" versus "rest" BCI. In the topographic map of each frequency range, the value assigned to each electrode is the grand average of the SU across all DWT features (from the same frequency range) extracted from that electrode and also across all participants. FIG. 9 f)-(j) shows the same topographic maps for the "yes" versus "no" BCI. Only the online trials from the respective online session were considered in these maps or the generation of these maps.

The DWT features used in the first four frequency ranges in FIG. 9 are the RMS and SD of DWT coefficients from the first four detail levels (~30-60 Hz, ~15-30 Hz, ~7.5-15 Hz, ~3.75-7.5 Hz). For the fifth frequency range (less than 3.75 Hz), the RMS and SD of DWT coefficients at the fifth detail level and the approximation level were averaged. The features from these two levels may not provide any substantial task-specific patterns and hence may be combined for the sake of saving space or computational efficiency. These five frequency ranges roughly match the five frequency bands of rhythmic brain activity, including gamma (>30 Hz), beta (14-30 Hz), alpha (7.5-14 Hz), theta (4-7.5 Hz) and delta (<4 Hz).

As shown in FIG. 9(a), no specific brain region exhibited considerable difference across participants in the lowest frequency range (delta band). In the second frequency range (theta band, FIG. 9b)), the average SU increased in some of the electrodes in the frontal lobe (Fz, F1, F2, F3 and AF3). In the third frequency range (~alpha and mu bands, FIG. 9(c)), the motor cortex and premotor areas (Cz, C1, C2, Fz, F2 and AF4) exhibited relatively high average SU. These motor and premotor differences may be due to motor planning and motor imagery exclusively associated with covert speech and not rest. Also, some of the electrodes in the parietal and occipital cortices (CPz, CP1, CP2, Pz, P2, P4 and PO4) provided relatively high SU (>0.3), which may be due to the different levels of attention required in the two mental tasks and also due to the involvement of the angular and supramarginal gyri. In the fourth frequency range (beta band, FIG. 9(d)), activation of channels above Broca's area (approximately F7 based on Ref. 22) were observed and some other channels in the frontal cortex (F3, F4 and F5), which may be attributable to the production of speech during the covert speech task. Also, relatively high SU was observed in the beta range of signals from the parietal cortex (including the supramarginal gyrus and angular gyrus approximately located at CP3, CP4, CP6, P4 and P6), both temporal cortices (TP8 and P7), motor cortex (Cz) and the occipital region (PO10) during "no" versus "rest" trials. The relatively high SU values in the occipital region may be attributable to the performance of differential visual imagery for "no" and "rest" trials. Note that the on-screen visual content was consistent across tasks (a black screen with a fixation cross). Finally, in the gamma range (FIG. 9(e)), the channels around Broca's area (F5, F7 and AF7) and one channel in the occipitotemporal area (PO9) exhibited higher average SU compared to other channels.

Broca's and Wernicke's areas, and the angular and supramarginal gyri may contribute to the production of imagined speech, while premotor areas take part in motor planning for speech articulation, even in the absence of actual movement. Task-related activations in Wernicke's area and the parietal cortex can be consistent with at least equal or greater activation in these regions compared to Broca's area.

For "yes" versus "no" classification (see FIG. 9(f)-(j)), no apparent difference was detected in delta, theta, alpha and mu rhythms. Both tasks required activation of the motor and premotor regions and hence the features in these regions were not discriminatory between classes. However, in the higher frequency ranges (beta and gamma), a discriminative pattern (SU>0.3) can be seen mostly in the left speech association regions (T7, FT7, Wernicke's area at CP5 and Broca's area at F7), which may be indicative of different high level neuronal activities accompanying iterative covert articulation of "yes" and "no".

Sensitivity and Specificity

Figure 10:
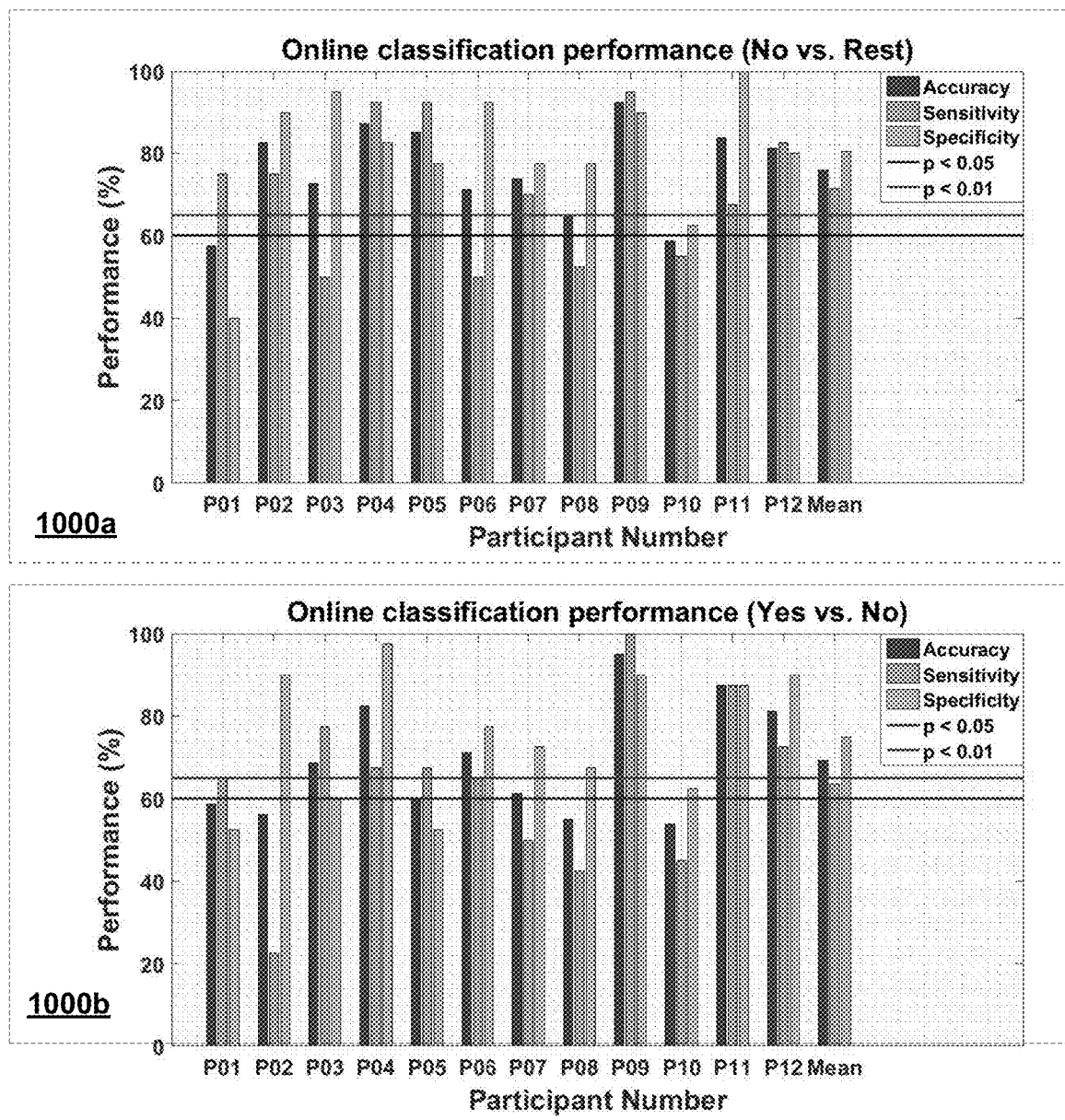
FIG. 10 shows an example online classification accuracy, sensitivity and specificity for each participant in the no versus rest and yes versus no online sessions, in accordance with some embodiments.

FIG. 10 illustrates the online classification accuracy, sensitivity and specificity (considering trials from both online blocks) for each participant in the no versus rest (1000a) and yes versus no (1000b) online sessions.

FIG. 10 at 1000a illustrates the online accuracy, sensitivity (the proportion of positive cases that are correctly classified) and specificity (the proportion of negative cases that are correctly classified) in detecting "no" trials (positive cases), versus rest trials (negative cases). In some participants, the difference between the sensitivity and specificity was considerable. For example, in three participants, this difference was more than 30%. However, on average, there was less than 9% difference, suggesting that the classifiers were not biased to one class.

The no versus rest BCI could be used as an on/off switch for an assistive device in an asynchronous paradigm. The user would only need to mentally repeat a word ("no" in this case) to turn on his/her assistive device or to call his/her caregiver. The level of sensitivity and specificity of the system could be tuned to suit the application and preferences of each user. For example, for activating a call bell for assistance, one may prefer high sensitivity to err on the side of safety. In contrast, for controlling a music player app, higher specificity might be preferred to minimize accidental (and potentially annoying) activations.

FIG. 10 at 1000b illustrates classification performance for the yes versus no online session (accuracy, sensitivity and specificity). The yes versus no BCI can be used to answer simple questions, such as "Are you in pain?", by the target population. For calculating sensitivity and specificity, in this case, the "yes" trials were considered as positive cases and "no" trials as negative cases. Hence, sensitivity measures the classifier's propensity for detecting "yes" responses while specificity reflects the classifier's ability to detect "no" responses. Again, due to the fact the classification model was a discriminative one, the sensitivity was not biased towards one class. When averaged across participants, the specificity (ability to correctly detect "no" trials) was ~11% higher than the sensitivity (tendency to correctly detect "yes" trials). This difference may be due to the fact that participants completed the no versus rest online session prior to the yes versus no session and hence had more practice with imagined repetition of "no". As noted, this is an example and some embodiments described herein classification of more than two classes or covert speech using brain-computer interfaces (BCIs), such as no, yes, and rest classes, for example.

In general, if one needs to tune the sensitivity and specificity of the two proposed BCIs (i.e., adjust the probability threshold for detection of a specific task), a generative classifier with a probabilistic model rather than a discriminative classifier is recommended. An SVM model may be used to help maximize classification accuracy.

The Impact of the Motor Cortex Signals

Electrodes from all brain regions can be used, including the primary motor cortex, to collect data and develop the two BCIs. The reason for including the primary motor cortex in the analysis was to exploit the readiness potential, activations associated with motor imagery of the covert speech task, and other motor-related signals occurring in the absence of motor execution. However, for individuals with congenital motor impairments, electrical activation in the motor regions during covert speech tasks might be attenuated or absent altogether. Also, possible glossal, buccal or pharyngeal activities associated with the subvocalization and covert speech may have contributed to the discrimination between mental tasks. Hence, as a secondary analysis, classification accuracies of the online sessions were estimated without EEG data from the primary motor cortex and premotor regions. Also, electromyography (EMG) artifacts were removed from the EEG data using a canonical correlation analysis. These classification accuracies could be more predictive of the performance of the BCIs with users from the target population.

FIG. 11 presents the classification accuracies of the online sessions after the removal of EMG artifacts and EEG data pertaining to the primary cortex and premotor regions (i.e. channels C3, C1, Cz, C2, C4, FC1 and FC2). Evidently, there is no significant decrease in the average accuracies across (~1.6% decrease in no versus rest session and ~1.1% in the yes versus no session) and within participants. All participants who surpassed the chance level in the online sessions (with the use of primary motor cortex data) remained above chance level. It may then be concluded that data collected from the motor regions (including any signals associated with potential unintentional motor movements and possible motor confounds due to subvocalization) were not critical to either classification problem.

FIG. 11 presents the classification accuracies of the online sessions after the removal of EMG artifacts and EEG data from the motor regions. The classification accuracy for each online session was calculated across all 80 online trials (last two blocks combined). The numbers in the parentheses denote the change in accuracies when motor cortex data were removed. Average accuracies exceeding the upper limit of the 95% confidence interval of chance are marked with an asterisk (*).

Minimum Required Duration of Each Trial

Figure 12:
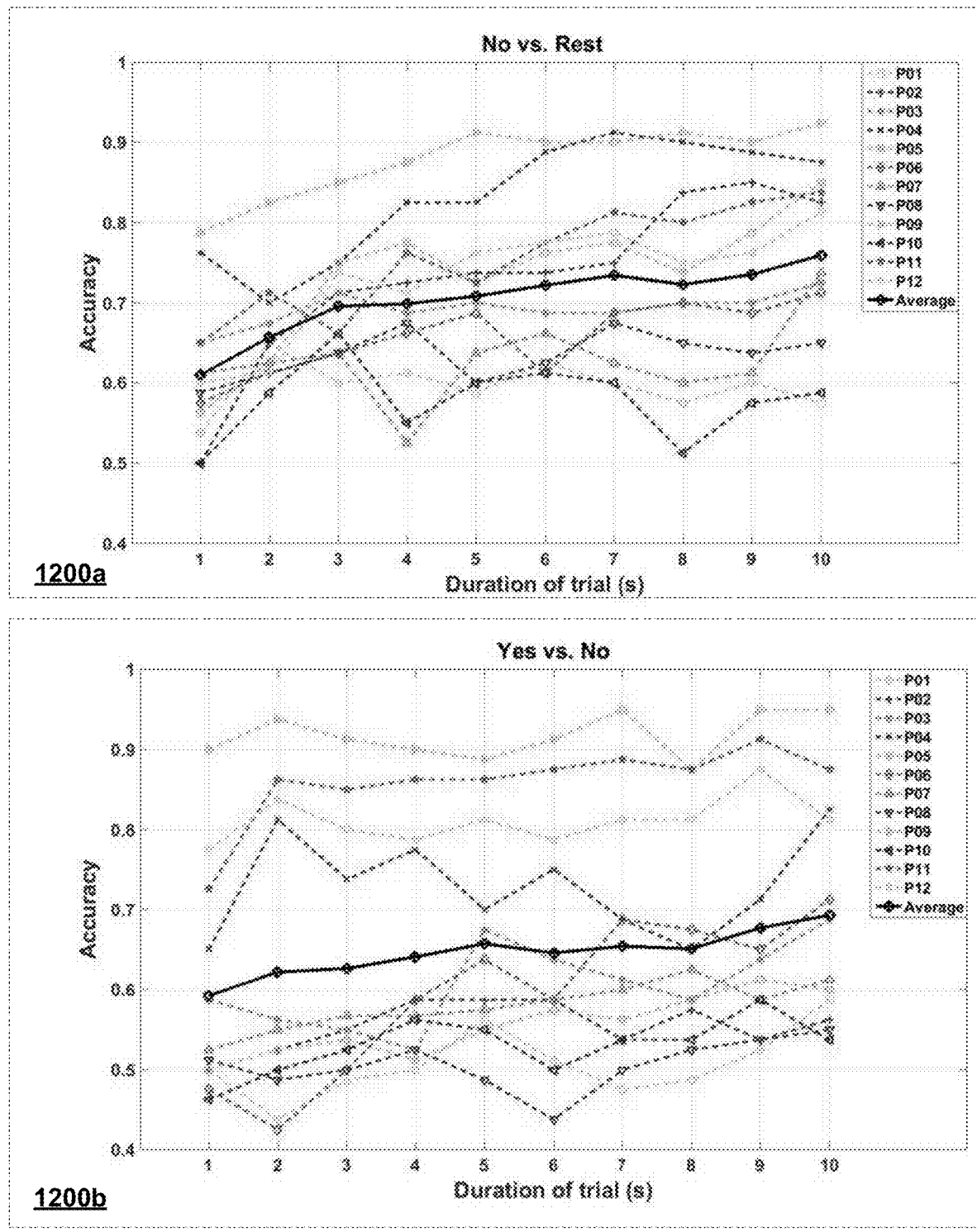
FIG. 12 illustrates example accuracies for no versus rest and yes versus no online sessions, in accordance with some embodiments.

Participants were asked to perform 10 s of speech imagery. To increase the information transfer rate, one could want to determine the minimum trial duration required for decoding speech imagery. FIG. 12 illustrates the accuracies for the no versus rest and yes versus no online sessions, had the duration of each trial been reduced. These hypothetical accuracies were estimated for ten different trial durations (from 1 s to 10 s). Classification accuracies using data from the online sessions for No versus Rest (1200a) and Yes versus No (1200b) BC's as the duration of each trial was reduced.

As expected, the average accuracy (black graph) tended to trend upward with an increase in trial duration. In the case of no versus rest classification, there seemed to be a crossover point at 3 s (see FIG. 12(a)). Incidentally, three seconds was the shortest duration for which the average accuracy still exceeded 70%. For the yes versus no case, FIG. 12(b) suggests that accuracy generally increased with duration. In this case, there was a trade-off between the duration of each trial and the BCI accuracy.

Discussion

Two embodiments of online BC's based on covert speech are described by way of example. For the discrimination between mental rehearsal of the word "no" versus unconstrained rest, an average online accuracy of 75.9±11.4% was reached across all participants with 10 out of 12 participants surpassing chance level accuracies. Task-related differences in the temporal patterns of FT7, C1, AF4, F8, PO7, PO3, PO8, and 01, alpha rhythms in Cz, C1, C2, CPz and P4, and beta rhythms in F7, F5, Cz, CP3, CP4, CP6, P4, TP8, P7 and PO10 tended to be important for classification. For the discrimination between mental repetition of "yes" versus "no", an average online accuracy of 69.3±14.1% was reached across all participants, with 8 out of 12 exceeding chance level accuracies. Task-related differences in the temporal patterns of CP5, CP3, T7, FT9 and FT7 channels, as well as beta and gamma rhythms in T7, FT7, CP5 and F7, were observed across participants.

The classification accuracies of the test sessions can be recalculated after the removal of electrodes from the primary and premotor cortices, as well as EMG artifacts. There were no significant decrease in the accuracies. This may indicate that the discrimination was not afforded by possible motor confounds (glossal, buccal or pharyngeal) due to sub-vocalization. An ultrasound system may also be used to detect and discard trials with any potential motor confounds associated with subvocalization or significant motor activities.

In some embodiments, more than one online session per participant for each BCI may be used as greater data samples may enhance classifier performance. For instance, in an embodiment described herein, within a given session, the average accuracies of the second online block were considerably higher than those of the first online block for both BCIs as the latter block had more training data. Further, participants usually become more engaged during the online sessions compared to the offline sessions due to the presence of feedback after each attempt.

In some embodiments, the covert speech task can be expanded to include other useful functionally intuitive words (such as, "left", "right", "stop" and "go" for navigational control of a wheelchair), to increase the number of participants, and to recruit individuals who present as locked-in. Also, using a combination of EEG and fNIRS may exploit the advantages of each modality and lead to improved BCI performance, as each modality has been individually applied to the classification of covert speech.

Covert speech may be suitable for selected BCI users. Some embodiments may enhance accuracies and reduce trial durations. BCI embodiments described herein may afford individuals with severe disabilities an intuitive means of control and choice-making. Embodiments enable an online BCI based strictly on covert speech.

In one embodiment, a BCI may be used to collect EEG signal data representing a pattern of activity in the brain of a user. The collected pattern of activity may be compared to pre-defined patterns of activity for that user. If a match is found, then the collected pattern of activity may be deciphered to represent a response associated with the matched stored pattern. Patterns of activities are characterized by signal features as described above.

FNIRS

Brain-computer interfaces (BCIs) can be used to provide a communication channel for individuals with motor impairments who are unable to communicate independently. BCIs can be associated with various activation protocols. A subset of these protocols can be referred to as reactive BCIs, which require the user to attend to external stimuli. Examples include P300 spellers and BCIs based on steady-state visually evoked potentials. BCI protocols without the involvement an external stimulus, also known as active BCIs, require users to perform a mental task. Some examples of these mental tasks are motor imagery, mental arithmetic and word generation. Given an adequate classification accuracy, a BCI user can use each of these mental tasks to convey a different message, e.g., to answer yes or no questions. However, these mental tasks are usually difficult to perform by the target population since the tasks are non-intuitive and are unrelated to the message that he/she would want to convey.

An intuitive mental task for BCIs which has gained attraction during the last decade is covert speech—also known as inner speech or imagined speech. Based on the outcomes of some studies, most of the successful attempts (accuracy higher than 70%, the acceptable threshold for BCI application) to classify electrophysiological brain signals during covert speech used invasive measurement techniques such as electrocorticography (ECoG). On the other hand, most BCIs based on non-invasive measurements of these signals, including electroencephalography (EEG) and magnetoencephalography (MEG), yielded average accuracies of less than 70% when discriminating between two different covert speech tasks. Moreover, only one study used a real-time paradigm which reported an average classification accuracy of approximately 69% (~69%) using EEG signals recorded during covert repetition of "yes" and "no".

Another brainwave response which has been investigated during speech related tasks is the hemodynamic response.

Initial speech-related studies on hemodynamic response used positron emission tomography (PET) and functional magnetic resonance imaging (fMRI) to study areas activated during the generation and comprehension of speech.

Initial studies to investigate the reliability of the hemodynamic response to decode speech focused on the averaged hemodynamic response over many repetitions of a speech task. However, a successful covert speech BCI should be able to decode speech in a single trial. Several studies used fMRI to discriminate between brain patterns activated when different nouns and Dutch vowels were presented either aurally or visually to participants. In one study, covert repetition of a nursery rhyme was used as an activation task (along with mental calculation and two motor imagery tasks) in a 4-class BCI based on fMRI, and yielded an average classification accuracy of greater than 90%. However, due to the limitations of fMRI, the duration of each trial was relatively long (approximately 2 minutes). More importantly, fMRI cannot be used in development of a portable BCI.

Another modality to measure the hemodynamic response is functional near-infrared spectroscopy (fNIRS). An fNIRS device can be portable, and the duration of each trial can be as short as 10-15 seconds. Early applications of fNIRS in speech recognition have focused on classifying between different speech modes: overt, silent and imagined speech from each other, and from trials without any speech activity. In one fNIRS study, each speech task included a whole sentence, and different speech modes were successfully discriminated using fNIRS data. In another fNIRS study, different patterns of hemodynamic responses were reported during trials of inner recitation of hexameter or prose, with mental arithmetic as a control task.

Due to the slow nature of the hemodynamic response, decoding small units of language, such as nouns, is more difficult compared to full sentences or different speech modes. One study reported an fNIRS-BCI for answering "yes" or "no" questions. This BCI was tested on a patient with amyotrophic lateral sclerosis (ALS) who answered different questions by simply thinking "yes" or "no". The duration of each trial was 25 seconds and an online classification accuracy of 71.7% was reached for this patient.

Another study tested the same "yes" or "no" paradigm on eight able-bodied participants using fNIRS. The duration of each trial was reduced to 10 seconds. Different types of hemodynamic features, feature numbers and time window sizes were tested and their accuracies were compared. An offline average accuracy of approximately 75% was reported when the best feature set was employed for each participant. They also reported that kurtosis features yielded the highest average classification accuracy among different types of features. One of the shortcomings of this study was that the location of the fNIRS channels did not cover any of the temporal regions which are some of the most important speech-related brain areas.

Yet another study expanded the work presented in the previous study. Four ALS patients used the same fNIRS-BCI to answer yes or no questions by thinking "yes" or "no". Three participants completed more than 46 sessions, each containing 20 questions, and one participant completed 20 sessions. Average online classification accuracy of more than 70% (above the chance-level) was reported across participants.

As summarized, none of the previous online non-invasive, portable neuroimaging studies (EEG and fNIRS) have investigated classification of more than 2 classes. The classification was either limited to covert speech versus a control condition, e.g. rest, or two covert speech tasks. Embodiments described herein classification of more than two classes or covert speech using brain-computer interfaces (BCIs), such as no, yes, and rest classes, for example.

Figure 13:
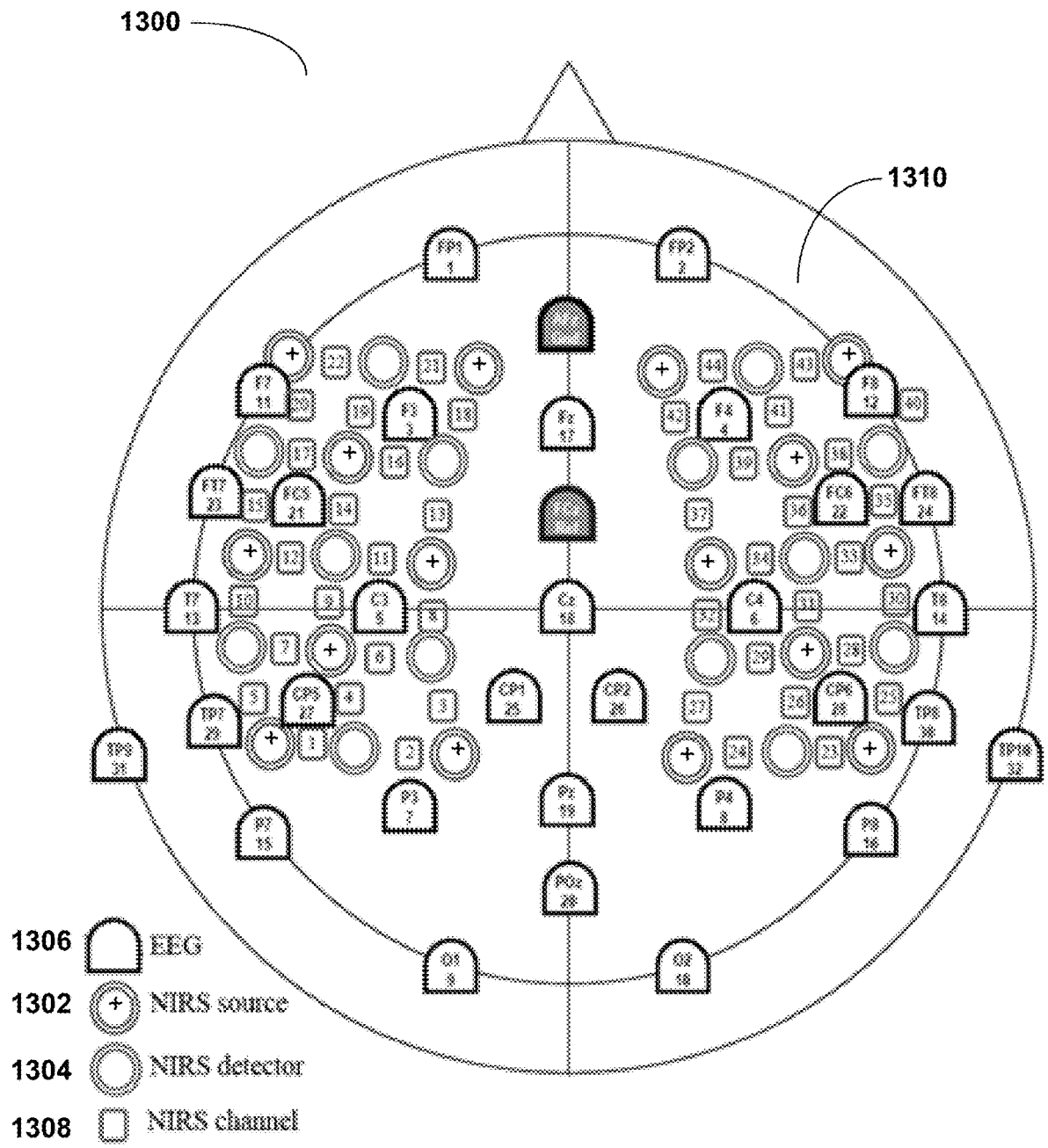
FIG. 13 illustrates, in a diagram, an example of the placement of BCI components on a scalp, in accordance with some embodiments.

NIRS measurements may be collected from the frontal, parietal and temporal cortices using a continuous-wave near-infrared spectrometer (e.g., an ETG-4000 Optical Topography System). FIG. 13 illustrates, in a diagram, an example of the placement 1300 of BCI components on a scalp 1310, in accordance with some embodiments. The BCI components comprise NIRS sources 1302 and detectors 1304 as well as EEG electrodes 1306. As shown in the example of FIG. 13, 16 NIR emitters 1302 and 14 photodetectors 1304 are integrated in two 3×5 rectangular grids of optical fibers in a standard EEG cap. Each NIR emitter may include two laser diodes that simultaneously emitted NIR light at wavelengths of 695 nm and 830 nm. The optical signals may be sampled at 10 Hz.

In one embodiment, adjacent positions in each of the two 3×5 grids, are 3 centimeters (cm) apart. Optical signals arising from source-detector pairs 1308 (or 'channels') separated by 3 cm may be acquired for analysis. This separation distance may yield a depth penetration of light between 2 and 3 cm, which surpasses the average scalp-to-cortex depth within the brain areas monitored. Using this configuration, optical signals may be acquired from a total of 44 measurement sites on the cerebral cortex, 22 on each hemisphere. In addition to NIRS measurements, EEG signals may be recorded from 32 locations shown in FIG. 13 using a BrainAmp DC amplifier.

Figure 14:
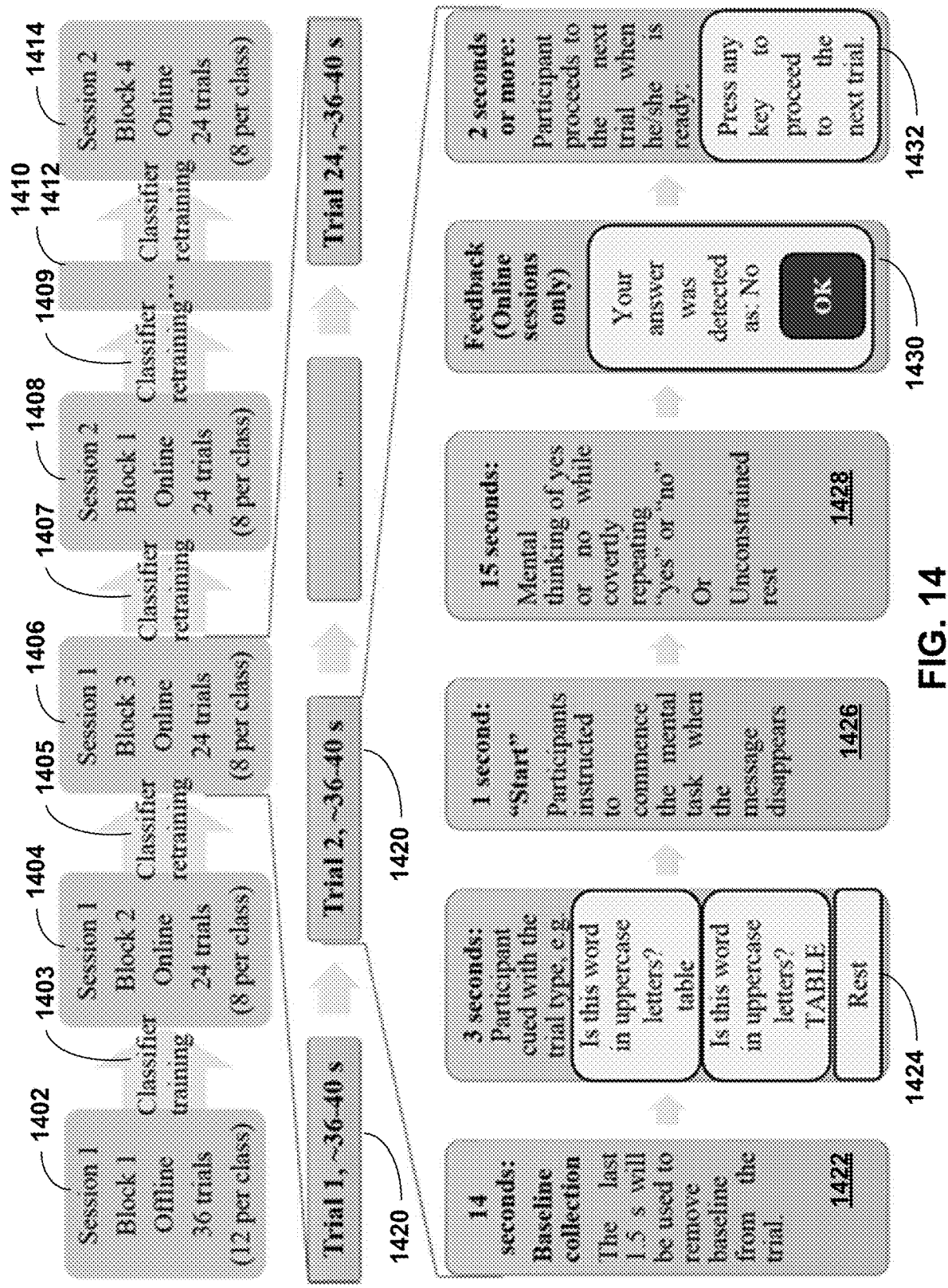
FIG. 14 illustrates, in a block diagram, an example of a timing diagram for an fNRIS experimental protocol, in accordance with some embodiments.

FIG. 14 illustrates in a block diagram, an example of a timing diagram 1400 for an experimental protocol, in accordance with some embodiments. By way of an example experiment, participants attended two sessions on two separate days. The first session comprised three blocks, starting with an offline block 1402 and followed by two online blocks 1404, 1406. In the offline block 1402, participants performed 36 trials, including 12 "yes" covert speech trials, 12 "no" covert speech trials and 12 unconstrained rest trials. The trials were presented in a pseudorandom order. At the end of the offline block 1402, a 3-class classifier was trained 1403 using the data from the offline block. Each online block 1404, 1406 consisted of 24 trials, 8 trials per class, presented in a pseudorandom order. Participants were presented with the classifier decision subsequent to each trial. The 3-class classifier was re-trained 1405, 1407 after each block using the data from all previous blocks.

The second session comprised four online blocks 1408, 1410, 1412, 1414, each with 24 trials equally distributed between three classes presented in pseudorandom order. Similar to the first session, the 3-class classifier was retrained 1409 after each block.

The timing diagram shown in FIG. 14 also illustrates a representation of 24 trials 1420, in accordance with some embodiments. Each trial 1420 starts with a fixation cross at the center of a blank screen. The fixation cross persisted throughout the trial. At the beginning of each covert speech trial, a question appeared on the screen for 3 seconds 1424 and was replaced by the instruction "start", which disappeared after 1 second 1426. The question was always the same: "Is this word in uppercase letters? WORD". For the yes trials, the word was written in uppercase letters and for the no trials, it was written in lowercase letters. The words were different in each question and were selected at random from a list of emotionally neutral words. At the beginning of each unconstrained trial, the phrase "rest" appeared on the screen for 3 seconds 1424, which was then replaced by the instruction, "start", for 1 second 1426. Each trial lasted for 15 seconds 1428.

In the example experiment, participants were instructed to commence the mental task as soon as the "start" instruction disappeared. For the covert speech trials, participants were instructed to think "yes" or "no" while iteratively repeating the word "yes" or "no" mentally. They were explicitly instructed to perform the task without any vocalization or motor movement, especially of the lips, tongue or jaw. In the unconstrained "rest" trials, participants allowed normal thought processes to occur without restriction. For online trials, feedback 1430 was sought whereby the participant confirmed if the answer detected matched the answer participants actually mentally thought. After 2 seconds or more 1432, the participant may then select to proceed to the next trial when the participant is ready. Embodiments described herein classification of more than two classes or covert speech using brain-computer interfaces (BCIs), such as no, yes, and rest classes, for example.

The duration of mental tasks was determined based on previous fNIRS studies and the suggested minimum measurement time for a hemodynamic response in the FNIRS literature. A 14 second baseline period 1422 prefaced each trial which allowed the hemodynamic signal to return to a basal level. Participants were asked to refrain from performing any of the covert speech tasks during this period. They had no knowledge of the type of the next trial at the time of baseline collection.

Figure 15:
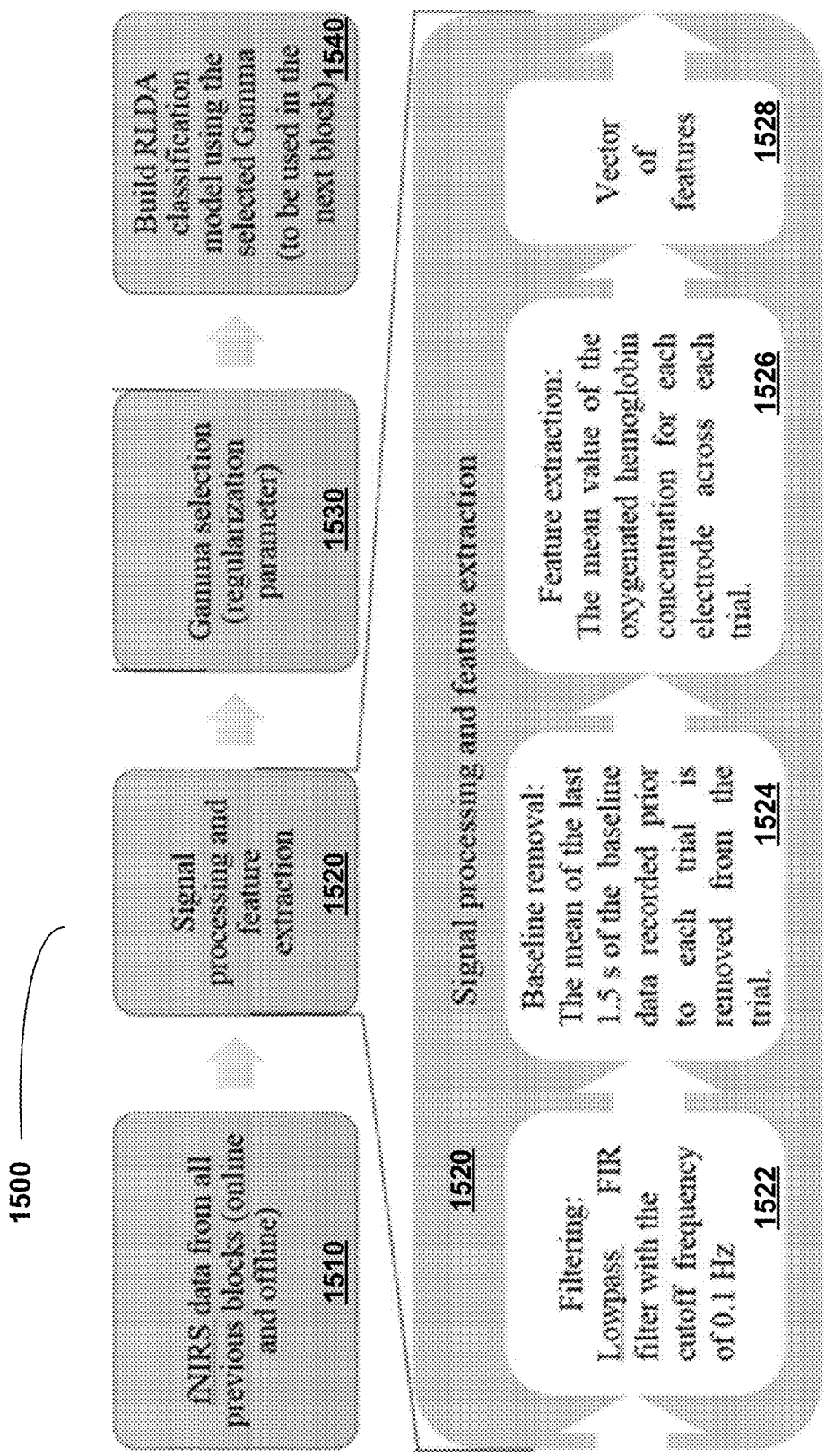
FIG. 15 illustrates, in a flowchart, an example of a method of building a classifier prior to each online block, in accordance with some embodiments.

FIG. 15 illustrates, in a flowchart, an example of a method of building a classifier prior to each online block 1500, in accordance with some embodiments. The method 1500 comprises collecting 1510 fNIRS data from all previous blocks (online and offline), performing 1520 signal processing and feature extraction, performing 1530 gamma selection (regularization parameter), and building 1540 a RLDA classification model using the selected Gamma (to be used in the next block). FIG. 15 also illustrates, in the flowchart, an example of a method of signal processing and feature extraction for covert speech classification using fNRIS signals 1520, in accordance with some embodiments. The method 1520 comprises signal processing 1522, baseline removal 1524, feature extraction 1526 and classification 1528.

For signal processing 1522, optical intensities may be converted to oxygenated hemoglobin concentration changes, denoted as [HbO], using the modified Beer-Lambert law. The signals may then be filtered using a using an FIR low-pass filter with a passband cut off frequency of 0.1 Hz, passband ripple of 1 dB, stopband cut off frequency of 0.5 Hz and minimum stopband attenuation of 45 dB. This filter may remove high frequency physiological noise, including Mayer wave at 0.1 Hz, respiration at ~0.3 Hz and cardiac activity at 0.8-1.2 Hz.

For baseline removal 1524, fluctuations in the value of HbO may not be limited to the periods of various cognitive tasks. The baseline value of HbO can change from one day to another or even from the beginning of a session to the end of it. Hence, some BCI studies added baseline collection periods to the beginning of each session or block to adjust for this natural fluctuation.

In the example experiment, baseline data was collected prior to each trial to calculate a more precise and trial-specific mean baseline value. From the 14 second baseline period, the mean of [HbO] may be calculated during the last 1500 milliseconds for each fNIRS channel. This value may then be subtracted from the subsequent trial on a per-channel basis. The last 1.5 seconds may be chosen instead of the entire 14 seconds since the hemodynamic signal requires approximately 12 seconds to return to its baseline value after any cognitive load. The mean of the last 1.5 seconds of the baseline data recorded prior to each trial may be removed from the trial.

For feature extraction 1526, the mean value of the oxygenated hemoglobin concentration change for each channel during the entire length of each trial may be used as features for classification. Hence, each trial may be represented as a 1×44 vector of features (44 channels×1 feature).

Other common types of NIRS features include variance, slope, skewness and kurtosis of changes in oxygenated, deoxygenated, and total hemoglobin concentrations. These features may be examined during pilot sessions. In the example experiment, the mean of [HbO] led to the highest classification accuracy and was therefore selected to provide real-time feedback during the online trials. This feature has been previously used in a similar "yes" vs "no" fNIRS study on ALS patients. Furthermore, it has been shown in another "yes" vs "no" study on healthy participants that features extracted from oxygenated hemoglobin concentrations provide more discriminative information compared to deoxy-hemoglobin concentrations.

For classification 1528, a regularized linear discriminant analysis (RLDA) algorithm may be used. In the example experiment, this method was chosen as it led to the highest average accuracy during the pilot sessions compared to support vector machines (linear, polynomial, radial basis function and sigmoid kernels), neural networks (multilayer perceptron with one hidden layer) and naïve Bayes classifiers. In some embodiments, the classification 1528 may result in a vector of features.

In one embodiment, a BCI may be used to collect fNIRS signal data representing a pattern of activity in the brain of a user. The collected pattern of activity may be compared to pre-defined patterns of activity for that user. If a match is found, then the collected pattern of activity may be deciphered to represent a response associated with the matched stored pattern. Patterns of activities are characterized by signal features as described above.

Ternary Hybrid FNIRS-EEG BCI

Although "imagined speech" overcomes the aforementioned shortcomings of other BCI mental tasks, it can be difficult to detect and classify using only non-invasive brain recording modalities, such as electroencephalography (EEG) or functional near-infrared spectroscopy (fNIRS). Most previous "imagined speech" BCI studies based on non-invasive measurements reported average accuracies below 70% (the suggested minimum threshold for practical BCI use) even in binary classification problems. To realize a reliable "imagined speech" BCI, classification accuracy should be improved further.

One solution for improving the performance of a BCI without changing the activation task is to combine two or more brain recording modalities. Specifically, previous work has utilized EEG in conjunction with fNIRS for BCI use. These modalities are mutually complementary: EEG has high temporal resolution but low spatial resolution, while fNIRS has low temporal resolution but superior spatial resolution.

In some embodiments, a hybrid fNIRS-EEG BCI may deploy these modalities sequentially (e.g., fNIRS as a BCI on/off switch and EEG to detect the type of the BCI task).

In some embodiments, BCIs may combine EEG and fNIRS to increase the number of control commands by using each modality to classify a different type of mental task.

In some embodiments, BCIs may use EEG and fNIRS for the classification of the same task but data from each modality were collected in separate sessions.

In some embodiments, a hybrid fNIRS-EEG BCI for ternary classification of imagined speech (mentally rehearsing the phrases "yes" and "no" to answer yes versus no questions and an idle state) is provided. This is a combination of fNIRS and EEG to classify imagined speech. Furthermore, a technique is proposed for the fusion of the two classifiers trained using the data from each modality alone.

Example embodiments were tested using an example experiment. Eleven typically developed, right-handed participants (six male) between the ages of 23 and 33 (mean age: 28.3±3.0 years) participated in this study. Participants were fluent in English, had normal or corrected-to-normal vision, and had no health issues that could adversely affect the measurements or the ability to follow the experimental protocol. These issues included cardiovascular, psychiatric, respiratory, neurological, degenerative, metabolic or alcohol-related conditions. Written consent was obtained from all participants prior to participating in the study.

In some embodiments, a multi-class hybrid fNIRS-EEG BCI is described herein based on imagined speech. Eleven participants, over two sessions, performed multiple iterations of three different mental tasks: thinking "yes" or "no" while mentally repeating the word for 15 seconds (s), or an equivalent duration of unconstrained rest. A technique for combining the data from two modalities is also described. In some embodiments, an average ternary classification accuracy of 68.9±19.3% across participants is provided. Such an accuracy is better than chance and approximately 5.6% higher than that attained with either EEG or fNIRS alone. In some embodiments, concurrent measurements of EEG and fNIRS can improve both classification accuracy and the information transfer rate of BCIs based on imagined speech.

Figure 16:
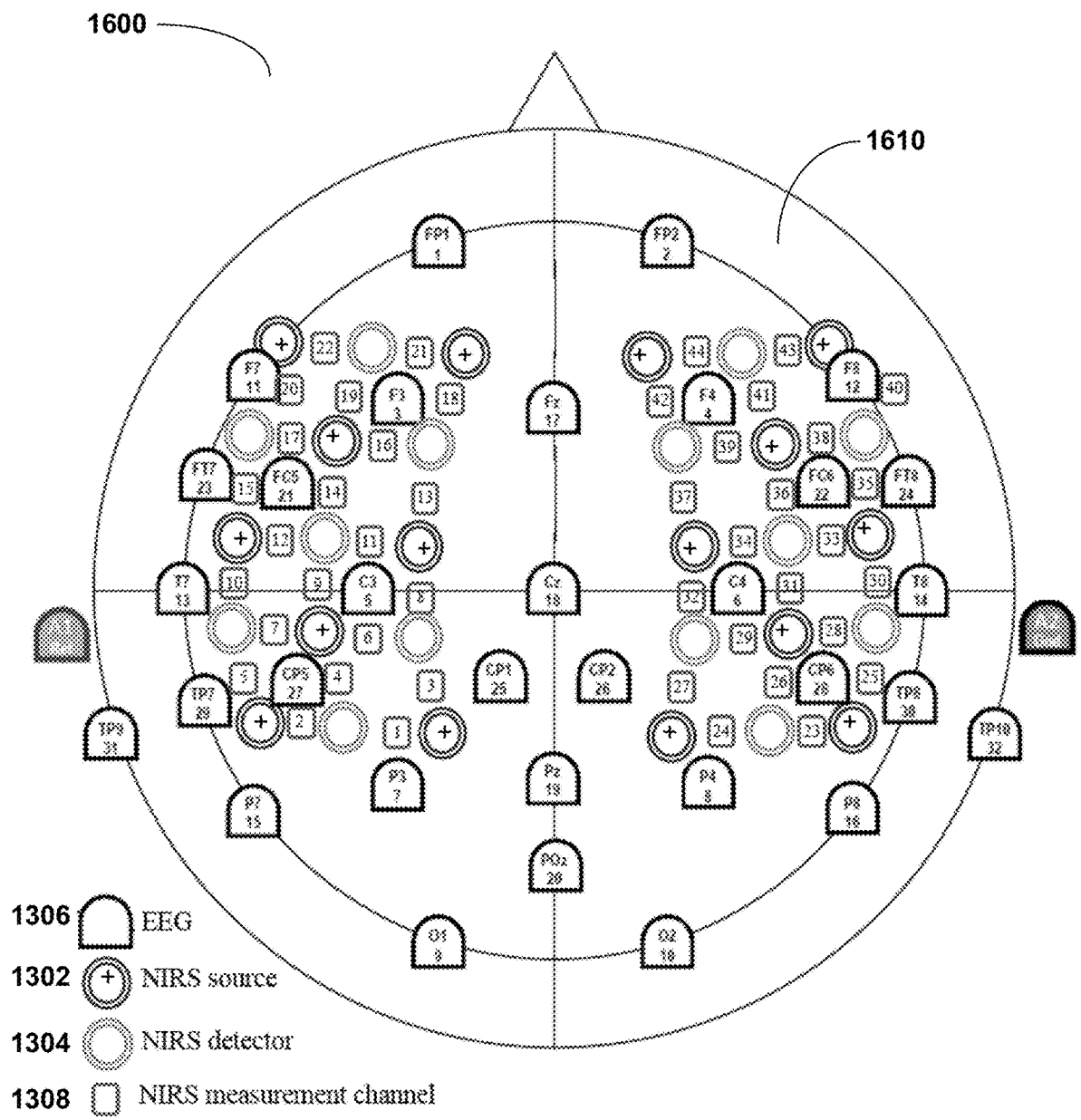
FIG. 16 illustrates an example of the location of electrodes on a scalp, in accordance with some embodiments.

EEG measurements were taken from 32 locations spanning all cortical regions, with a higher density of electrodes in the temporal speech-related regions. EEG recording was performed using dry EEG electrodes (e.g., an Acticap Xpress Twist) connected to a BrainAmp DC amplifier. Reference and ground (GND) electrodes were placed on the left and right earlobes, respectively (A1 and A2). Fp1 and Fp2 electrodes were only used to detect and remove EOG artifacts. FIG. 16 illustrates location of the electrodes, in an exemplary embodiment.

fNIRS data were collected using a near-infrared spectrometer (e.g., ETG-4000 Optical Topography System) from the temporal, frontal, and parietal cortices. Each emitter comprised two laser diodes that concurrently emitted light at wavelengths of 695 nm and 830 nm. The reflected light was captured using the detectors with a sampling frequency of 10 Hz. Two 3×5 rectangular grids were used to fit 16 emitters 1302 and 14 photodetectors 1304, spaced 3 cm apart. Optical signals were acquired only from source-detector pairs separated by 3 cm (henceforth referred to as "channels" 1308). As a result, fNIRS signals were collected from a total of 44 locations distributed equally and symmetrically between the two hemispheres (see FIG. 16).

The EEG electrode holders 1306, near-infrared (NIR) emitters 1302 and NIR photodetectors 1304 were integrated into a custom-made cap 1610. FIG. 16 illustrates the placement of EEG electrodes 1306 and fNIRS sources 1302 and detectors 1304. EEG positions are marked using the nomenclature of the international 10-20 system along with the corresponding channel number 1308.

Each participant attended two sessions on two separate days. During each trial, participants were asked to perform one of three mental tasks: unconstrained rest, "yes" trials, and "no" trials. In the "yes" and "no" trials, participants answered "yes" and "no" questions by thinking "yes" or "no" while mentally repeating the phrase "yes" or "no" in response to stimuli. The first session consisted of an offline block of 36 trials, followed by two online blocks of 24 trials each. The second session consisted of 4 online blocks of 24 trials each. Each block contained an equal number of each task presented in pseudorandom order, with each trial lasting for 15 s.

In the online trials, real-time feedback was provided after the completion of the mental task. The feedback was calculated by a classifier trained on fNIRS data. The online fNIRS classification results were previously reported above. Note that EEG data were collected from only 11 of the 12 participants of the fNIRS study presented above.

Figure 17:
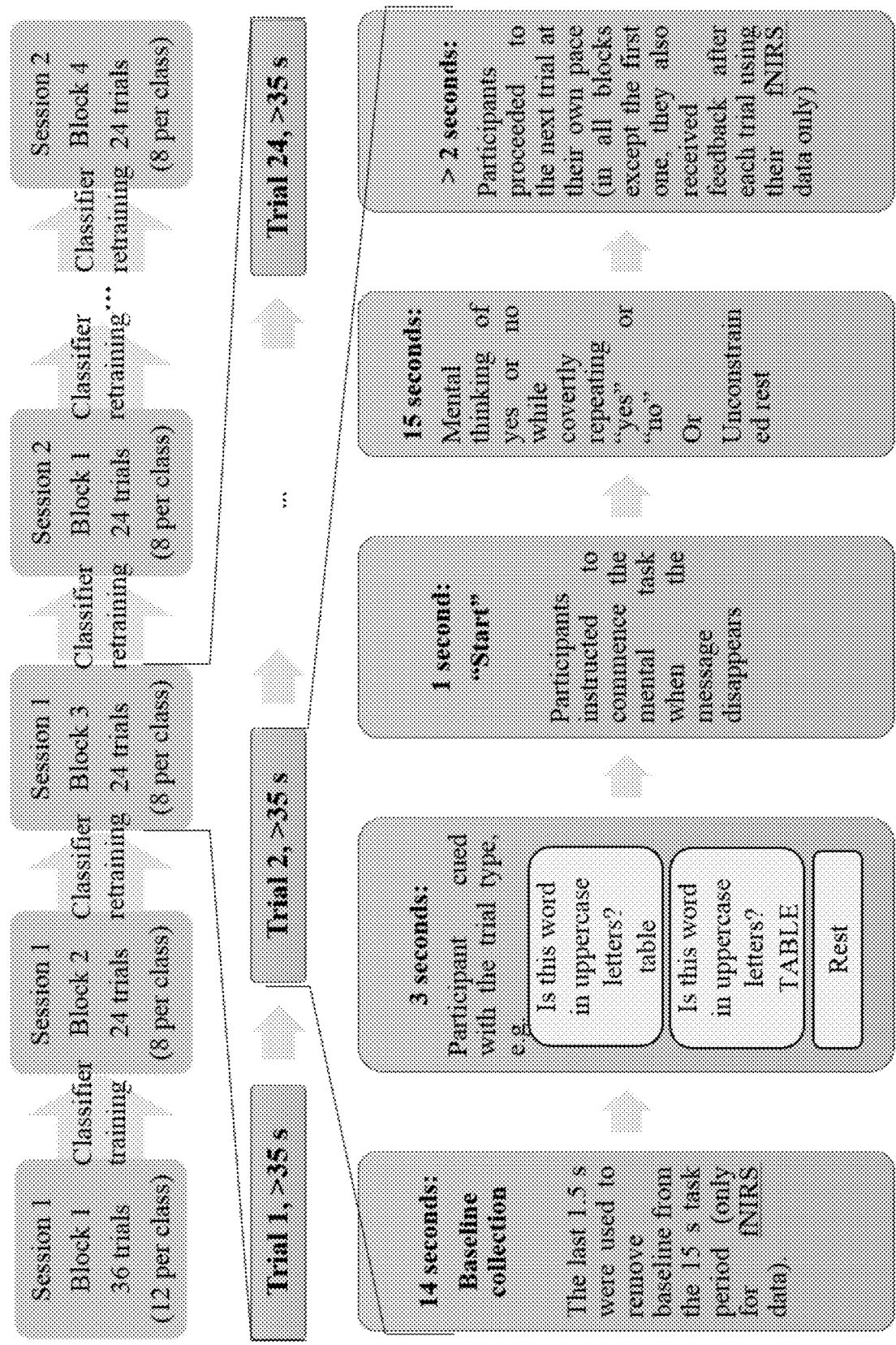
FIG. 17 illustrates, in a block diagram, an example of a timing diagram for a hybrid experimental protocol, in accordance with some embodiments.

Herein, the performance of the hybrid system is evaluated and compared to the performance of each modality alone. The timing diagram of the experiment is presented in FIG. 17.

Training and Test Set

The entirety of the first session plus the first block of the second session was used as the training dataset for offline classification, resulting in 108 trials (36 per class). This training set was used for the selection of the feature extraction and classification methods, as well as their required hyper-parameters. The method and/or parameter(s) which yielded the highest cross-validation (CV) accuracy (100 runs of 10-fold CV) on the training set was selected. In some embodiments, the cross validation may be K-fold, where K is determined by the amount of data available (i.e., sample size dependent). For example, K may depend on the number of features (e.g., a K-fold CV folds into K subsets, where within each subset, the number of data points is preferably approximately ten times the number of features).

The remaining 72 trials (24 per class) i.e., last 3 blocks from session 2 were used as the test set. Prior to each test block, the classifier was retrained with the accumulated data from all previous blocks, following a pseudo-online paradigm. For example, the second test block would utilize a classifier trained on 132 trials, comprising the training set (108 trials) plus data from the first test block (24 trials).

EEG Data Analysis

Signal Preprocessing 1820b

EEG data 1810b were first filtered 1822b using a 0.5-40 Hz bandpass Butterworth filter. The low-pass cut-off frequency of 40 Hz was used and considered as a maximum reliable frequency of the dry electrodes.

In order to remove 1824b electrooculography (EOG) artifacts, an ADJUST algorithm was deployed; independent components due to eye blinks, and horizontal and vertical eye movements were removed. The remaining components were used to reconstruct the EEG data. The reconstructed artifact-free signals for each of the 30 electrodes were subjected to further analysis (Fp1 and Fp2 data were solely used for EOG artifact detection and were not considered thereafter).

Feature Extraction 1820b

Discrete wavelet transform (DWT) coefficients were extracted 1826b from each trial. Other common types of features for EEG classification, such as autoregressive components, common spatial patterns, and spectral power estimates were also tested on the training set, but DWT features using the Symlet-10 (sym10) wavelet yielded the highest training set accuracy and hence was selected for the test set. DWT features have previously proven discriminatory for EEG signals accompanying imagined speech.

DWT has been frequently deployed EEG analysis given its ability to localize information in both frequency and time domains. Six levels of decomposition yielded the lowest CV classification error in the training set. The root-mean-square (RMS) of the outputs from each DTW decomposition level were used as features for classification. These six levels represent the following frequency ranges: 62.5-31.3 Hz, 31.3-15.6 Hz, 15.6-7.8 Hz, 7.8-3.9 Hz, 3.9-2.0 Hz, and 2.0-1.0 Hz. A total of 180 DWT features 1828b were generated from each trial.

fNIRS Data Analysis

The signal processing, baseline removal and feature extraction steps 1820a for the fNIRS data are the same as the steps described above for the fNIRS embodiment. In short, the fNIRS data 1810a were filtered 1822a using a Chebyshev type II low-pass filter with a passband cutoff frequency of 0.1 Hz and stopband cutoff frequency of 0.5 Hz. A trial-specific mean baseline was removed 1824a using a 1.5 s period just prior to stimulus presentation. The mean value 1826a of [HbO] for each of the 44 channels, over the entire length of a trial, constituted the input features 1828a. Other common types of fNIRS features, such as variance, slope, kurtosis and skewness of changes in deoxygenated and oxygenated hemoglobin concentrations, were examined, but the mean of [HbO] yielded the lowest CV classification error in the training set.

Classification

Regularized Linear Discriminant Analysis (RLDA)

Linear discriminant analysis has been extensively used in BCI studies. While the curse of dimensionality and overfitting are very common problems in BCI classification, a large number of these studies did not regularize their LDA models. In one study, three linear discriminant models (LDA, support vector machines and logistic regression) were compared and concluded that comprehensive optimization of the regularization parameter(s) may be much more important than the choice of the model.

Herein, the regularized linear discriminant analysis (RLDA) algorithm is used for classification. The regularization parameter was optimized separately for each participant, each modality and each test block. RLDA was chosen for classification as it led to the highest CV classification accuracy compared to support vector machines (linear, polynomial, radial basis function and sigmoid kernels), logistic regression and a neural network with one hidden layer.

Choosing the Regularization Parameter 1830a, 1830b

The test set consisted of three blocks. For each block, the classifier was re-trained with all available trials (including those from previous test blocks). The regularization parameter was also optimized prior to testing each block using 1832a, 1832b 100 runs of 10-fold CV on all previous trials. In other words, the average CV accuracy was calculated for $\gamma=0.05, 0.1, 0.15, \ldots, 1$ and the $\gamma$ which provided the highest CV accuracy was used to train the next test block. A separate classifier for EEG 1834b and fNIRS 1834a was trained and the value of $\gamma$ was optimized for each of these two classifiers separately (see 1830a, 1830b in FIGS. 18A and 18B). Specifically, $$\gamma^*_{EEG} = \underset{\gamma}{\operatorname{argmax}}(A_{EEG_{\gamma=0.05}}, A_{EEG_{\gamma=0.1}}, \ldots, A_{EEG_{\gamma=1}}) \quad (1)$$

and, $$\gamma^*_{fNIRS} = \underset{\gamma}{\operatorname{argmax}}(A_{fNIRS_{\gamma=0.05}}, A_{fNIRS_{\gamma=0.1}}, \ldots, A_{fNIRS_{\gamma=1}}) \quad (2)$$

In equations (1) and (2), $A_{EEG}$ and $A_{fNIRS}$ are the average classification accuracies over 100 runs of 10-fold CV on all previous trials (the entire training set as well as previous test blocks, if any) using EEG and fNIRS measurements, respectively (i.e., all previous blocks). In this study, 10-fold CV was used over leave one out cross validation (LOOCV) since it provides better generalizability and less variance. In some embodiments, the cross validation may be K-fold, where K is determined by the amount of data available (i.e., sample size dependent). For example, K may depend on the number of features (e.g., a K-fold CV folds into K subsets, where within each subset, the number of data points is preferably approximately ten times the number of features).

Figure 18A:
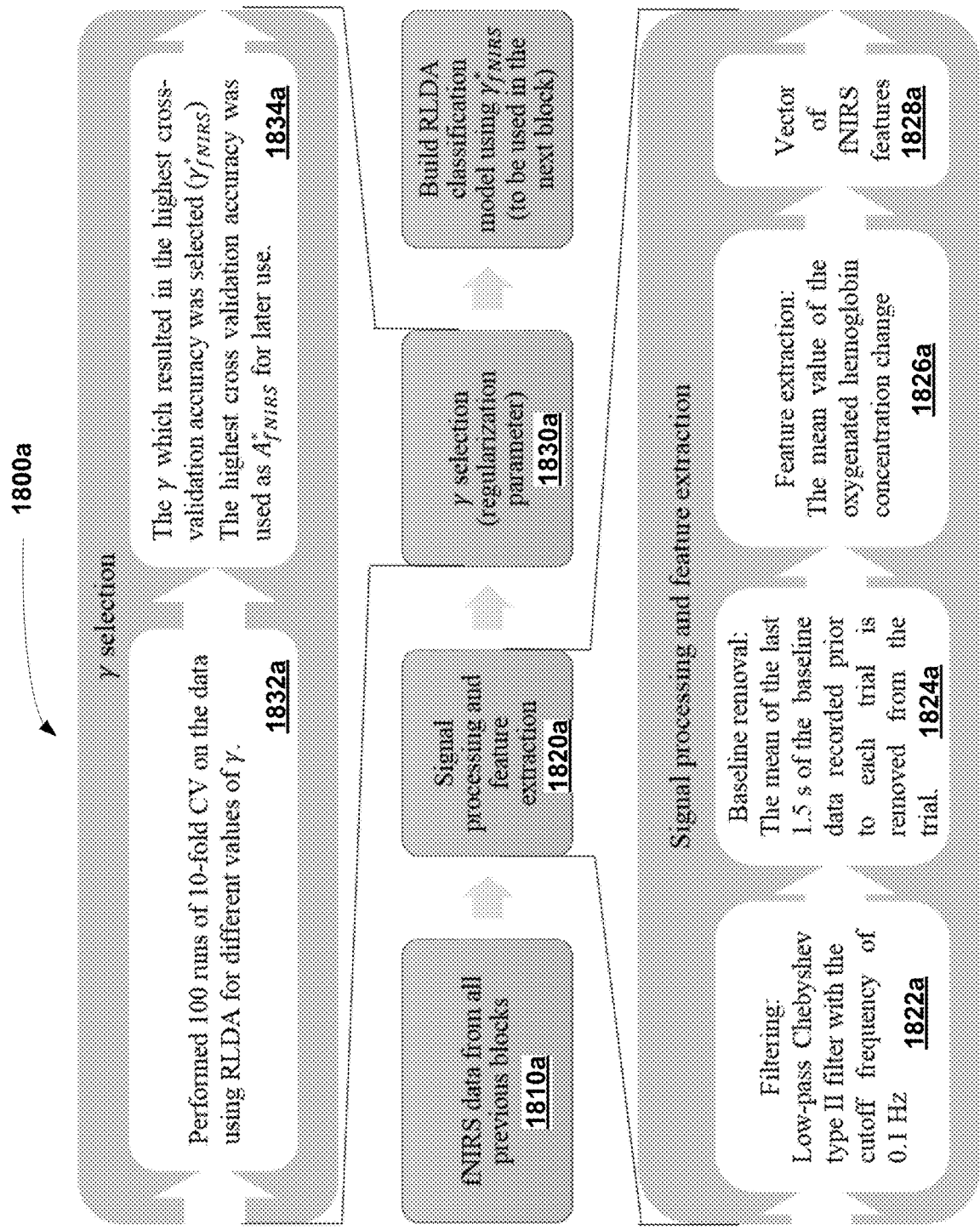
FIGS. 18A and 18B illustrate in flowcharts, examples of a method for building the fNIRS classifier and the EEG classifier, in accordance with some embodiments.
Figure 18B:
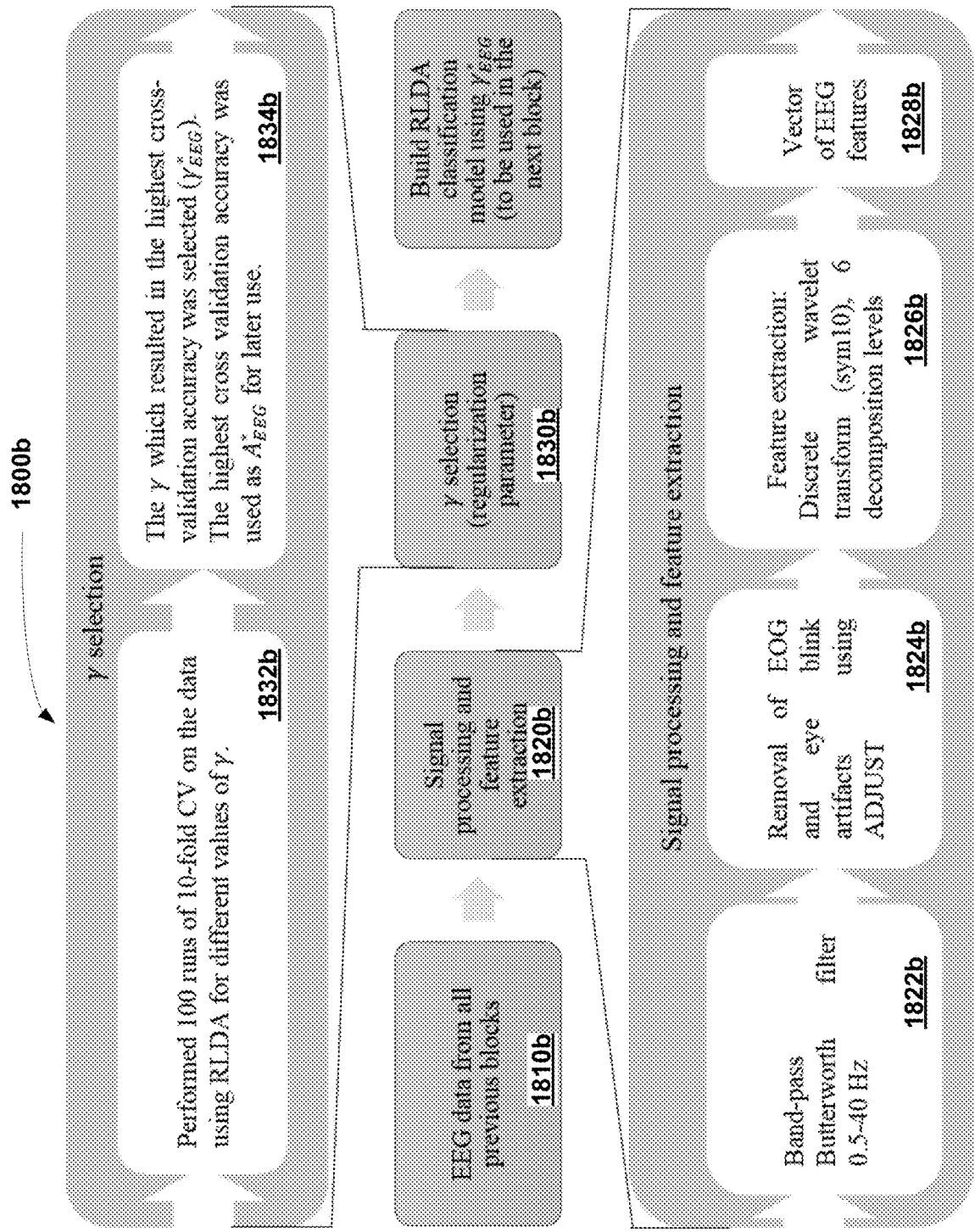

FIGS. 18A and 18B illustrate in flowcharts, examples of a method for building the fNIRS classifier (1800A) and the EEG classifier (1800B) (CV=cross validation, RLDA=regularized linear discriminant analysis), in accordance with some embodiments.

Figure 19:
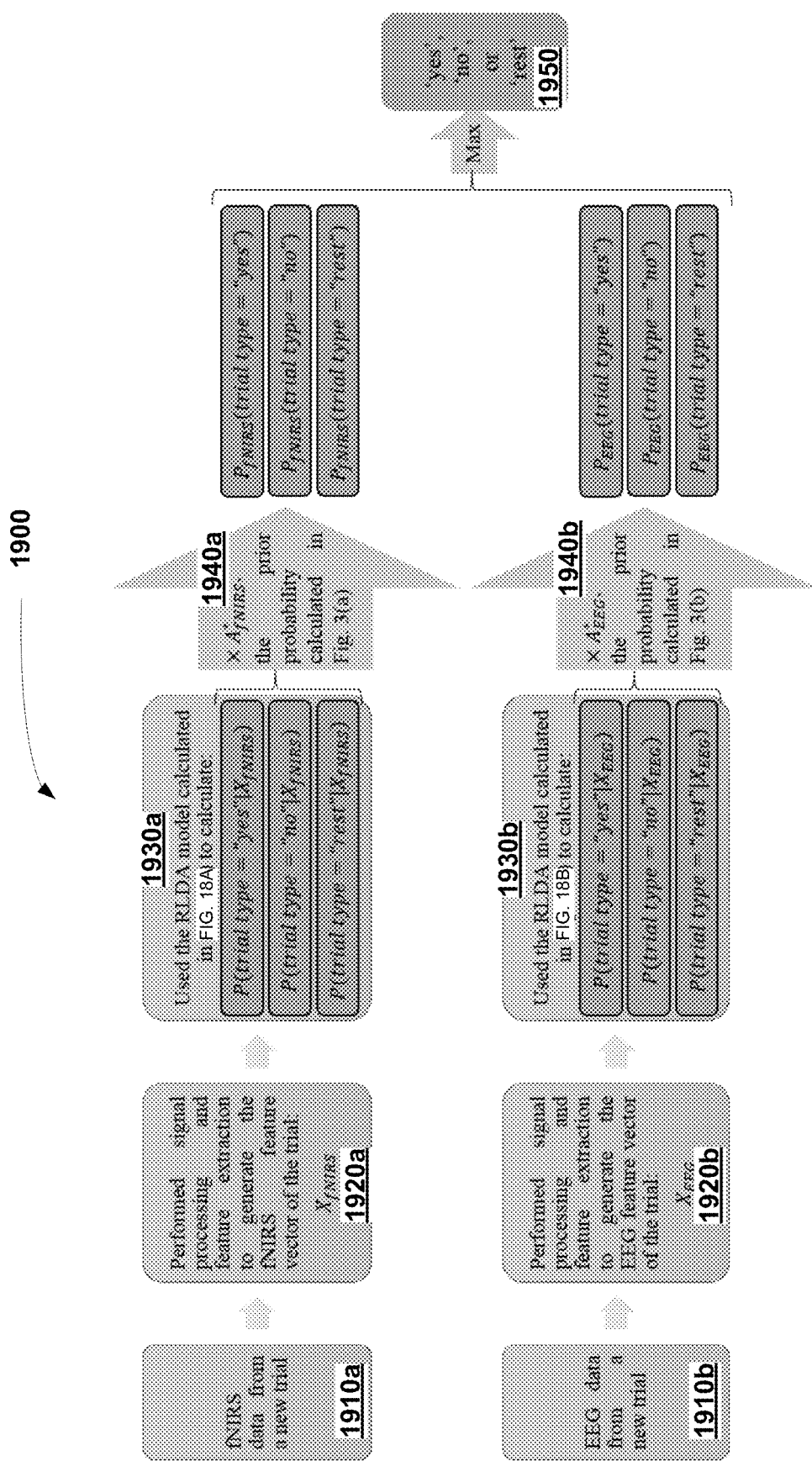
FIG. 19 illustrates, in a flowchart, an example of a method for combining the EEG and fNIRS classifiers, in accordance with some embodiments.

FIG. 19 illustrates, in a flowchart, an example of a method 1900 for combining the EEG and fNIRS classifiers, in accordance with some embodiments.

Fusion of EEG and fNIRS Classifiers

After optimizing the regularization parameters and training two classifiers, one using EEG data 1800b and one using fNIRS data 1800b, these two classifiers were combined using a probabilistic model to make predictions on the test set. The classifier predicted the class, C, of a single trial according to:

$$C(X_{EEG}, X_{fNIRS}) = \underset{c=\text{"yes"},\text{"no"},\text{"rest"}}{\operatorname{argmax}} P(C = c \mid X_{EEG}, X_{fNIRS}) \quad (3)$$

where $X_{EEG}$ and $X_{fNIRS}$ are feature vectors of that particular trial in the test set. The probabilities that the trial belonged to each of three classes were obtained using the following three equations:

$$P(C=\text{"no"} \mid X_{EEG}, X_{fNIRS}) = \max(A^*_{EEG} \times P(C=\text{"no"} \mid X_{EEG}), A^*_{fNIRS} \times P(C=\text{"no"} \mid X_{fNIRS})) \quad (4)$$

$$P(C=\text{"yes"} \mid X_{EEG}, X_{fNIRS}) = \max(A^*_{EEG} \times P(C=\text{"yes"} \mid X_{EEG}), A^*_{fNIRS} \times P(C=\text{"yes"} \mid X_{fNIRS})) \quad (5)$$

$$P(C=\text{"rest"} \mid X_{EEG}, X_{fNIRS}) = \max(A^*_{EEG} \times P(C=\text{"rest"} \mid X_{EEG}), A^*_{fNIRS} \times P(C=\text{"rest"} \mid X_{fNIRS})) \quad (6)$$

where $A^*_{EEG}$ and $A^*_{fNIRS}$ are the average CV classification accuracies obtained with the optimized regularization parameters, $Y_{EEG}$ and $Y_{fNIRS}$ for each modality.

In other words, the class labels for a given test trial was taken as that predicted either by the EEG classifier or the fNIRS classifier, depending on the confidence of each classifier's prediction and the classifier's prior probability. The analytical steps for combining the two classifiers are summarized in FIG. 19. The raw data is obtained from a new trial 1910a, 1910b. Next, signal processing and feature extraction are performed 1920a, 1920b to generate the fNIRS and EEEG feature vector of the trial. These steps 1920a and 1920b are similar to 1820a and 1820b of FIGS. 18A and 18B. Next the RDLA model calculated in FIGS. 18A and 18B are used 1930a, 1930b to determine the probability that a data point is one of "yes", "no" or "rest".

For fNIRS 1930a, the RDLA model determines:

$P(\text{trial type}=\text{"yes"} \mid X_{fNIRS})$ $P(\text{trial type}=\text{"no"} \mid X_{fNIRS})$ $P(\text{trial type}=\text{"rest"} \mid X_{fNIRS})$ These three probabilities are multiplied 1940a by $A^*_{fNIRS}$, the prior probability determined in FIG. 18A, to determine:

$P_{fNIRS}$(trial type="yes")

$P_{fNIRS}$(trial type="no")

$P_{fNIRS}$(trial type="rest")

For EEG 1930b, the RDLA model determines:

$P$(trial type="yes"|$X_{EEG}$)

$P$(trial type="no"|$X_{EGG}$)

$P$(trial type="rest"|$X_{EGG}$)

These three probabilities are multiplied 1940b by $A^*_{EGG}$, the prior probability determined in FIG. 18B, to determine:

$P_{EGG}$(trial type="yes")

$P_{EGG}$(trial type="no")

$P_{EGG}$(trial type="rest")

The larger (max) of the fNIRS or EGG probabilities is used to determine 1950 if the trial belongs to (i.e., class label) "yes", "no" or "rest".

Results

Ternary Classification Accuracies

Table 1 provides the ternary classification accuracy across the three test blocks for all participants using EEG only, fNIRS only, and the proposed hybrid system. For the entire test set (last three columns of the table), the upper limits of the 95.0, 99.0 and 99.9% confidence intervals of the corresponding chance estimates were 43.1%, 45.8% and 51.4%, respectively (based on the binomial cumulative distribution function). Average accuracies exceeding these thresholds are marked with one, two and three asterisks, respectively.

only, an average classification accuracy of 63.6±21.1% was obtained across participants with seven participants exceeding the same limit.

Figure 20:
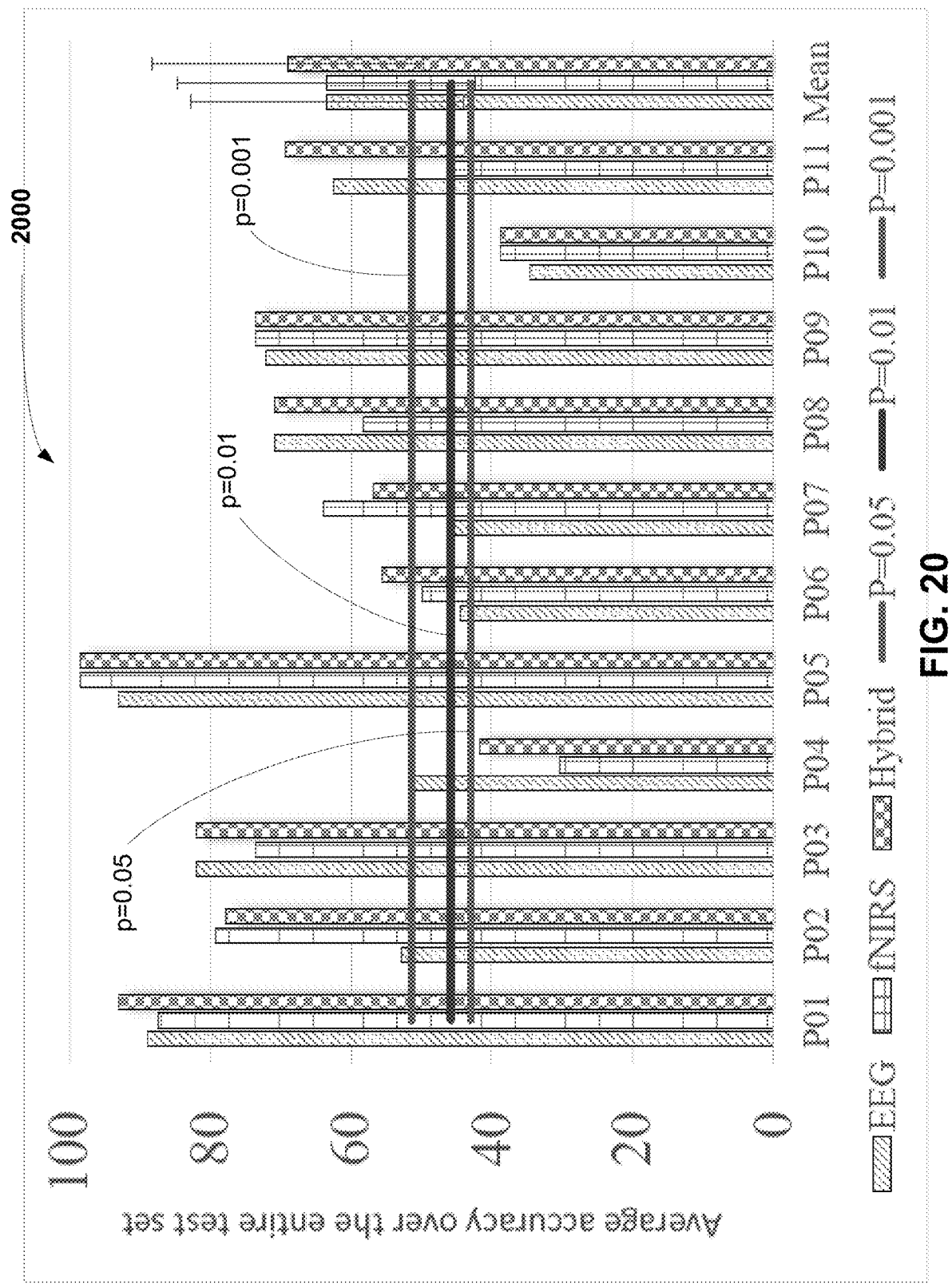
FIG. 20 illustrates, in a graph an example of an average classification accuracy, in accordance with some embodiments.

FIG. 20 illustrates, in a graph 2000, the average classification accuracy (yes versus no versus rest) over the entire test set across participants using each modality separately and together in the hybrid system.

After the fusion of fNIRS and EEG classifiers using the proposed method, the average classification accuracy across participants improved to 68.9±19.2% (>5% improvement compared to EEG and fNIRS alone) with nine participants surpassing the upper limits of the 99.9% confidence interval around chance (one more participant compared to EEG and two more compared to fNIRS). FIG. 20 illustrates the average classification accuracy over the entire test set across participants using each modality on its own and in combination.

Figure 21:
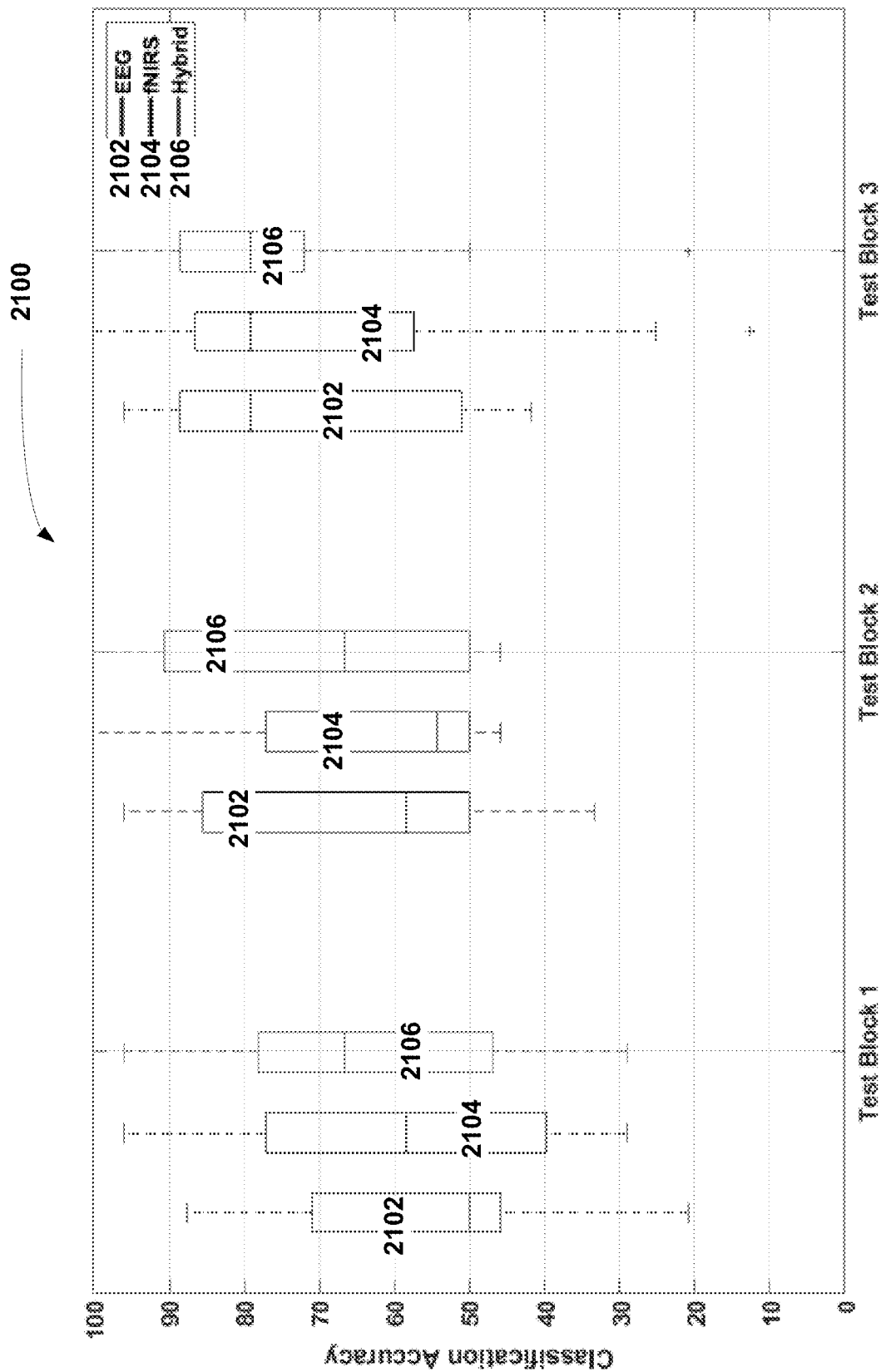
FIG. 21 illustrates, in a graph, an example of a classification accuracy, in accordance with some embodiments.

FIG. 21 illustrates, in a graph 2100, the classification accuracy (yes versus no versus rest) across the three test blocks using each modality separately and together in the hybrid system.

If we consider the average accuracies across the three test blocks separately, the hybrid BCI yielded a ternary classification accuracy of 63.3%, 68.6% and 75.0% in the first, second and third test blocks respectively. Recall that the classifier used for each test block was trained on data from all previous blocks. FIG. 21 depicts the changes in the classification accuracy across the three test blocks using each single modality 2102, 2104 and the hybrid 2106 system.

The Contribution of Each Modality in the Hybrid System

Figure 22:
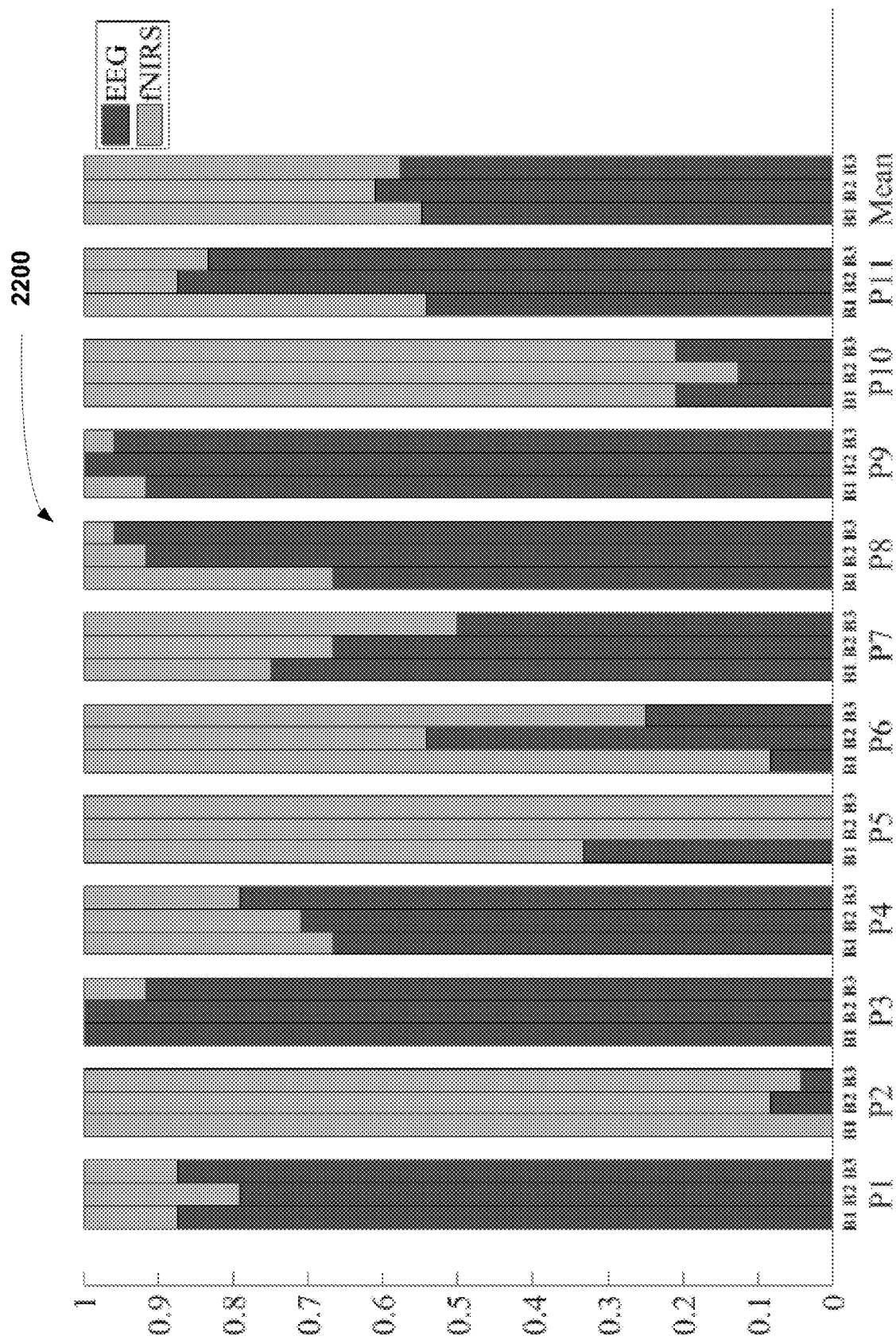
FIG. 22 illustrates, in a graph, the contribution of each modality for different participants and in different blocks, in accordance with some embodiments.

FIG. 22 illustrates, in a graph 2200, the contribution of each modality (i.e., the percentage of trials for which the decision was made by that modality) for different participants and in different blocks (B1, B2, B3 denote blocks 1,

TABLE 1

Ternary classification accuracies (%) of participants across three test blocks.

| | Test Block 1 | | | Test Block 2 | | | Test Block 3 | | | All Test Blocks | | |
|---|---|---|---|---|---|---|---|---|---|---|---|---|
| | EEG | fNIRS | Hybrid | EEG | fNIRS | Hybrid | EEG | fNIRS | Hybrid | EEG | fNIRS | Hybrid |
| P1 | 79.1*** | 83.3*** | 83.3*** | 91.7*** | 83.3*** | 95.8*** | 95.8*** | 95.8*** | 100*** | 88.9*** | 87.5*** | 93.1*** |
| P2 | 50.0* | 79.2*** | 79.2*** | 58.3** | 79.2*** | 75.0** | 50.0* | 79.2*** | 79.2*** | 52.8*** | 79.2*** | 77.8*** |
| P3 | 70.8*** | 66.7*** | 70.8*** | 95.8*** | 70.8*** | 95.8*** | 79.2*** | 83.3*** | 79.2*** | 81.9*** | 73.6*** | 81.9*** |
| P4 | 45.8 | 29.2 | 29.2 | 50.0* | 50.0* | 45.8 | 58.3** | 12.5 | 50.0* | 51.4*** | 30.6 | 41.7 |
| P5 | 87.5*** | 95.8*** | 95.8*** | 95.8*** | 100*** | 100*** | 95.8*** | 100*** | 100*** | 93.1*** | 98.6*** | 98.6*** |
| P6 | 45.8 | 37.5 | 41.7 | 33.3 | 45.8 | 50.0* | 54.2* | 66.7*** | 75.0** | 44.4* | 50.0* | 55.6*** |
| P7 | 45.8 | 58.3** | 50.0* | 50.0* | 50.0* | 50.0* | 41.7 | 83.3*** | 70.8*** | 45.8** | 63.9*** | 56.9*** |
| P8 | 66.7*** | 54.2* | 66.7*** | 54.2* | 50.0* | 54.2* | 91.7*** | 70.8*** | 91.7*** | 70.8*** | 58.3*** | 70.8*** |
| P9 | 70.8*** | 70.8*** | 75.0** | 66.7*** | 62.5*** | 66.7*** | 79.2*** | 87.5*** | 79.2*** | 72.2*** | 73.6*** | 73.6*** |
| P10 | 20.8 | 45.8 | 45.8 | 41.7 | 45.8 | 50.0 | 41.7 | 25.0 | 20.8 | 34.7 | 38.9 | 38.9 |
| P11 | 45.8 | 29.2 | 58.3** | 62.5*** | 54.2* | 70.8*** | 79.2*** | 54.2* | 79.2*** | 62.5*** | 45.8** | 69.4*** |
| AVG | 57.20 | 59.09 | 63.26 | 63.64 | 62.88 | 68.56 | 69.70 | 68.94 | 75.00 | 63.50 | 63.64 | 68.94 |
| SD | 19.37 | 22.35 | 20.14 | 21.82 | 18.11 | 20.70 | 21.09 | 28.10 | 22.75 | 19.39 | 21.14 | 19.24 |

In Table 1, accuracies exceeding the upper limits of the 95%, 99% and 99.9% confidence intervals of chance are marked with *,  and *, respectively. These limits were calculated using the binomial cumulative distribution and based on the number of trials. For individual test blocks (24 trials), these limits were 50.0%, 58.3% and 62.5%, respectively. For the combination of all blocks (72 trials), these limits were 43.1%, 45.8% and 51.4%, respectively.

By using EEG data only, an average classification accuracy of 63.5±19.4% (over the entire test set) was reached across participants with eight participants surpassing the upper limits of 99.9% confidence interval. With fNIRS data 2 and 3). Four participants (P2, P3, P5 and P9) had almost all trials classified using a single modality. For all other participants, a mix of EEG and fNIRS data was used, with the overall mean being 57% of trials labeled by the EEG-BCI.

Figure 23:
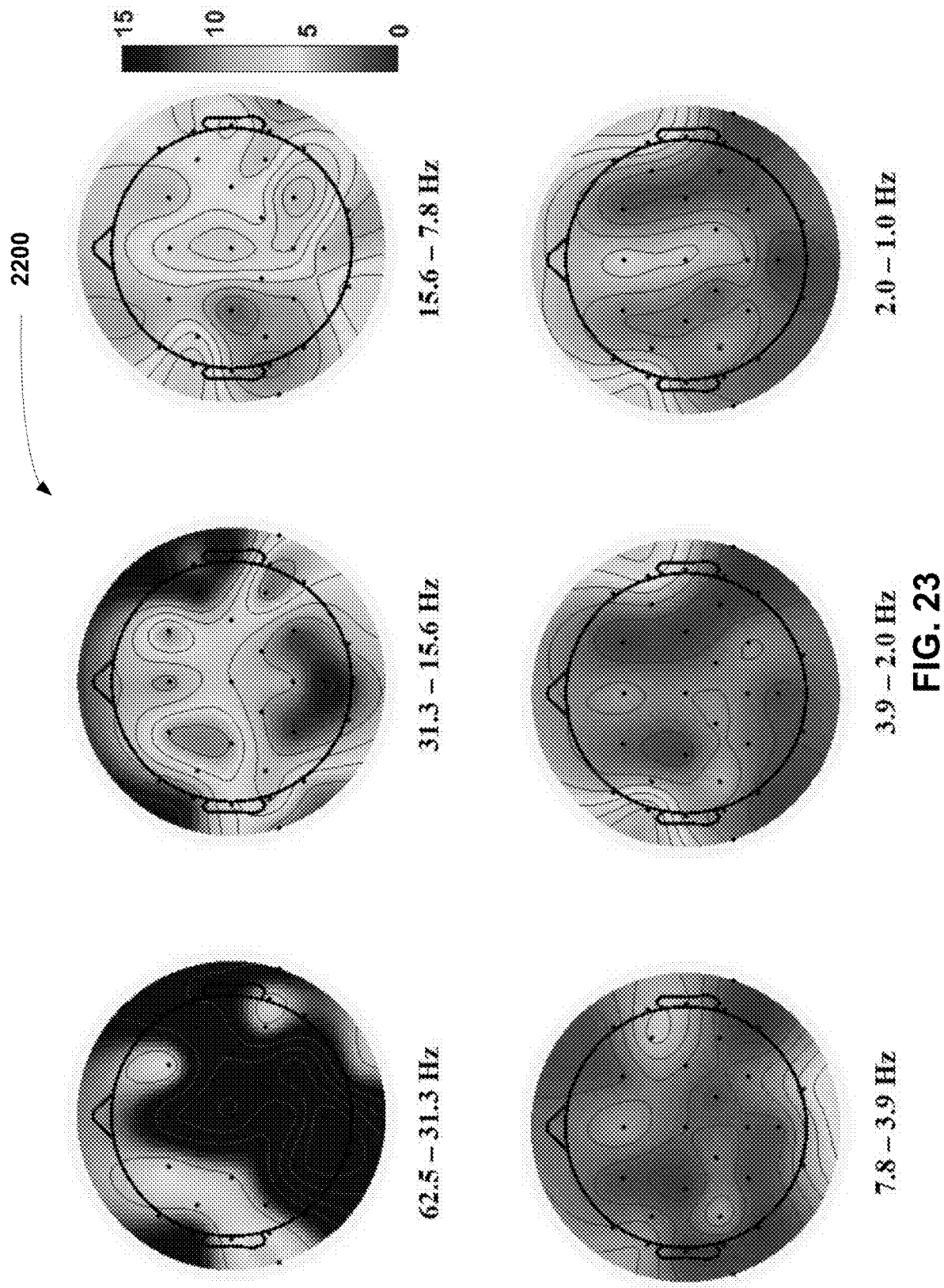
FIG. 23 illustrates, in topographic maps, examples of a Fisher criterion value for frequency ranges, in accordance with some embodiments.

The Role of Different EEG and fNIRS Channels in Providing Discriminative Information FIG. 23 illustrates, in topographic maps 2300, examples of Fisher criterion value (averaged across all test blocks and participants) for each frequency range (yes versus no versus rest).

Figure 24:
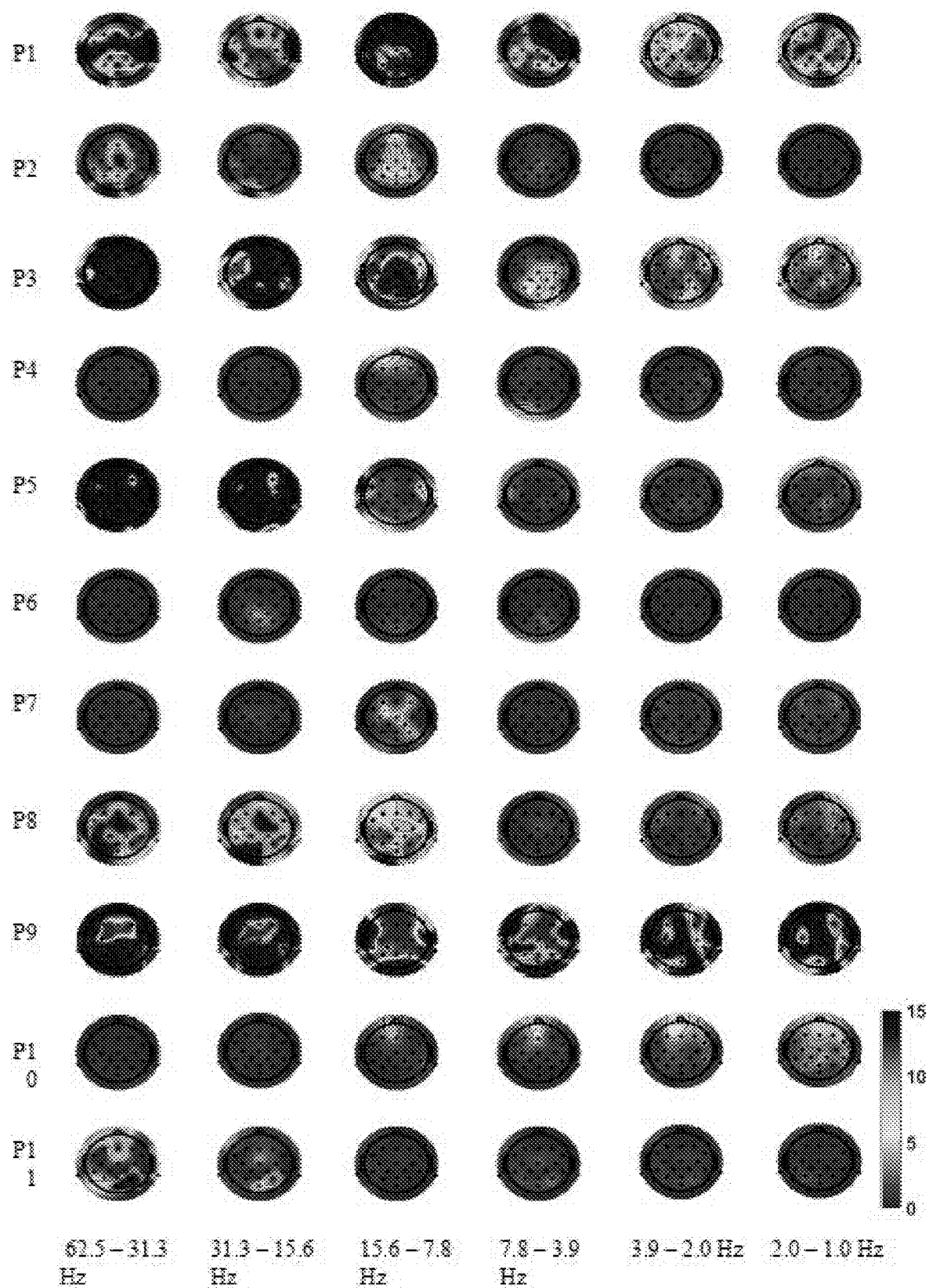
FIG. 24 illustrates, in topographic maps, examples of average Fisher criterion values for a plurality of participants and for frequency ranges, in accordance with some embodiments.

To highlight brain regions which exhibit task-specific EEG patterns of activity, we used the average value of the Fisher criterion across participants for each frequency range and each electrode. As a reminder, RLDA ranks each feature's discriminative capability based on the Fisher criterion, with the highest score being most discriminant. Six wavelet features were extracted from each channel, representing six pseudo-frequency levels. For each of these frequency levels, only one feature per channel was generated. FIG. 23 depicts the topographic maps 2300 of Fisher criterion (averaged across all test blocks and participants) for each frequency range. To highlight the variations across participants, the same topographic maps for all participants are shown in FIG. 24.

Evidently, more EEG channels provided discriminative information in higher frequency ranges (gamma and beta) than in lower frequency ranges. This finding is consistent with previous classification of imagined speech using EEG. However, the location of the channels which provided the highest Fisher criterion value varied across participants. This inconsistency could be attributed to subject-specific performance of imagined speech tasks, as well as inter-individual variations in the size and shape of different brain regions. Determining precisely which Brodmann regions provided the highest activation would require fMRI and structural data for each individual.

Similar analysis for the fNIRS measurements in this study are provided above for the fNIRS embodiment, which showed that the fNIRS channels in the left temporal and temporoparietal regions provided the highest Fisher criterion value.

Development of a Subject-Independent BCI

The classification results provided in Table 1 were calculated using a subject-dependent analysis—the classifier used for each participant was trained using their data only. One of the main objectives of current BCI research is to develop a ready-to-use BCI which requires minimum effort to set up. In general, developing a subject-independent BCI is feasible for reactive brain responses such as steady state visual evoke potential (SSVEP) and P300. However, for most BCIs based on active tasks (i.e., tasks without the need of an external stimulus), user-dependent classification is required to account for subject-specific performance of these tasks.

FIG. 24 illustrates, in topographic maps, examples of Fisher criterion values (averaged across all blocks) for each participant and for each frequency range (yes versus no versus rest).

Figure 25:
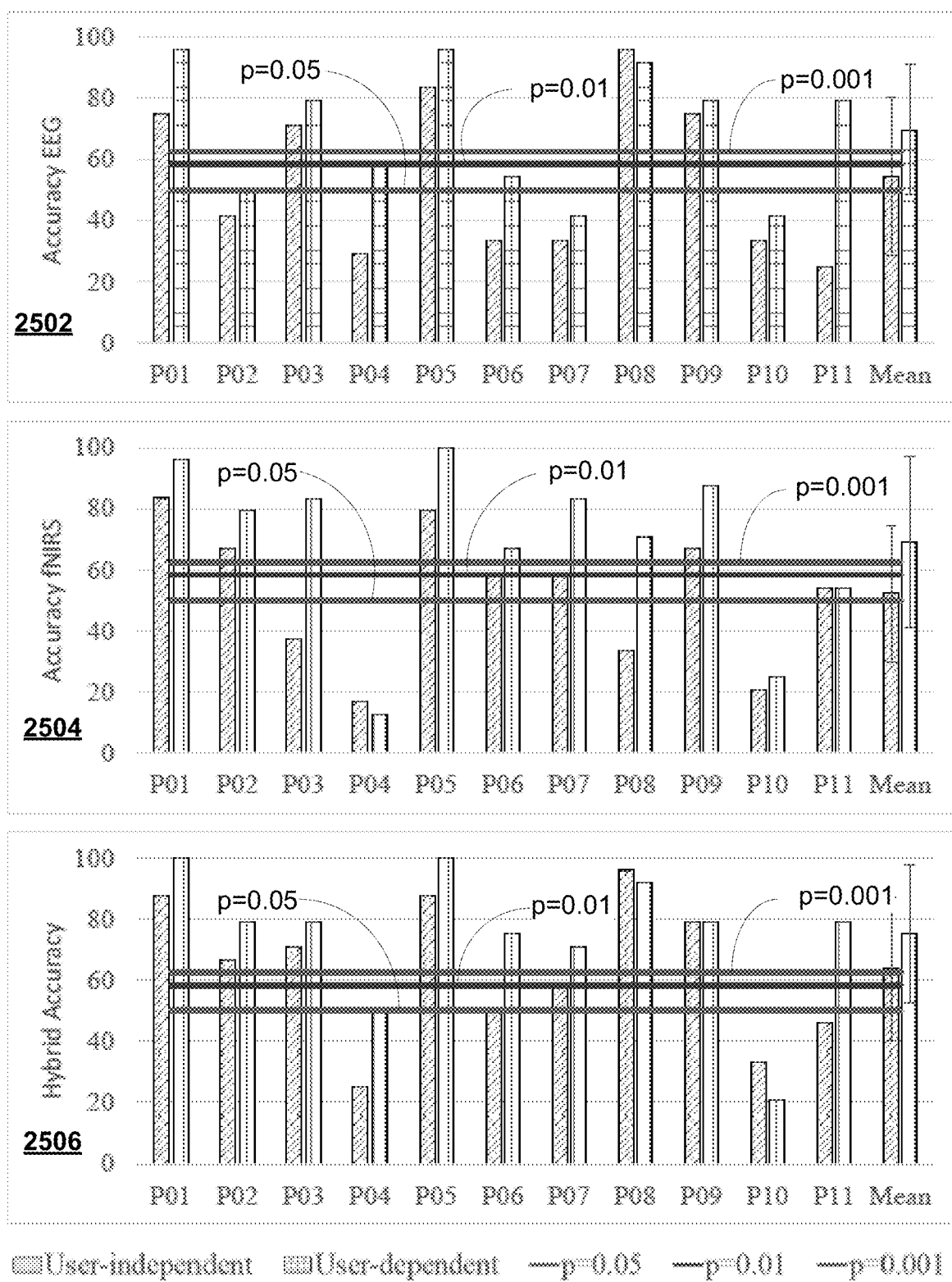
FIG. 25 illustrates an example of a comparison of subject-independent accuracies with their subject-dependent counterparts, in accordance with some embodiments.

In this section, the performance of the proposed BCI using a subject-independent classifier is examined. Table 2 provides the classification accuracy of each participant in the last test block when the exact same classifier was used for all participants. This classifier was trained using all trials of all participants except their last blocks. In FIG. 25, these subject-independent accuracies are compared with their subject dependent counterparts.

TABLE 2

The classification accuracy (%) of each participant in the last test block when the subject-independent classifier was used.

| | EEG | fNIRS | Hybrid |
|---|---|---|---|
| P1 | 75.0*** | 83.3*** | 87.5*** |
| P2 | 41.7 | 66.7*** | 66.7*** |
| P3 | 70.8*** | 37.5 | 70.8*** |
| P4 | 29.2 | 16.7 | 25.0 |
| P5 | 83.3*** | 79.2*** | 87.5*** |
| P6 | 33.3 | 58.3** | 50.0* |
| P7 | 33.3 | 58.3** | 58.3** |
| P8 | 95.8*** | 33.3 | 95.8*** |
| P9 | 75.0*** | 66.7*** | 79.2*** |
| P10 | 33.3 | 20.8 | 33.3 |
| P11 | 25.0 | 54.2 | 45.8 |
| AVG | 54.2* | 52.3* | 63.6*** |
| SD | 25.8 | 22.4 | 23.3 |

In Table 2, accuracies exceeding the upper limits of the 95%, 99% and 99.9% confidence intervals of chance (50.0%, 58.3% and 62.5%, respectively) are marked with *,  and *.

For EEG 2502 and fNIRS 2504 alone, the subject-independent classifier provided a significantly lower accuracy compared to the subject-dependent classifiers (p=0.002 and p=0.004 for EEG and fNIRS, respectively, using the Wilcoxon signed-rank test). All participants except one (P8 for EEG and P4 for fNIRS) obtained a lower accuracy using the subject-independent classifier. In both cases, the mean accuracy dropped below the 99% confidence interval for chance.

FIG. 25 illustrates a comparison of subject-independent accuracies (yes versus no versus rest) with their subject-dependent counterparts. Participant accuracy displayed as a percentage. Mean accuracy displayed as mean±SD as a percent.

For the hybrid 2506 BCI, the difference between subject-dependent and subject-independent classifiers was not significant (p=0.11 using the Wilcoxon signed-rank test and a Holm-Bonferroni correction for three multiple comparisons).

Reducing the Duration of Trials

Figure 26:
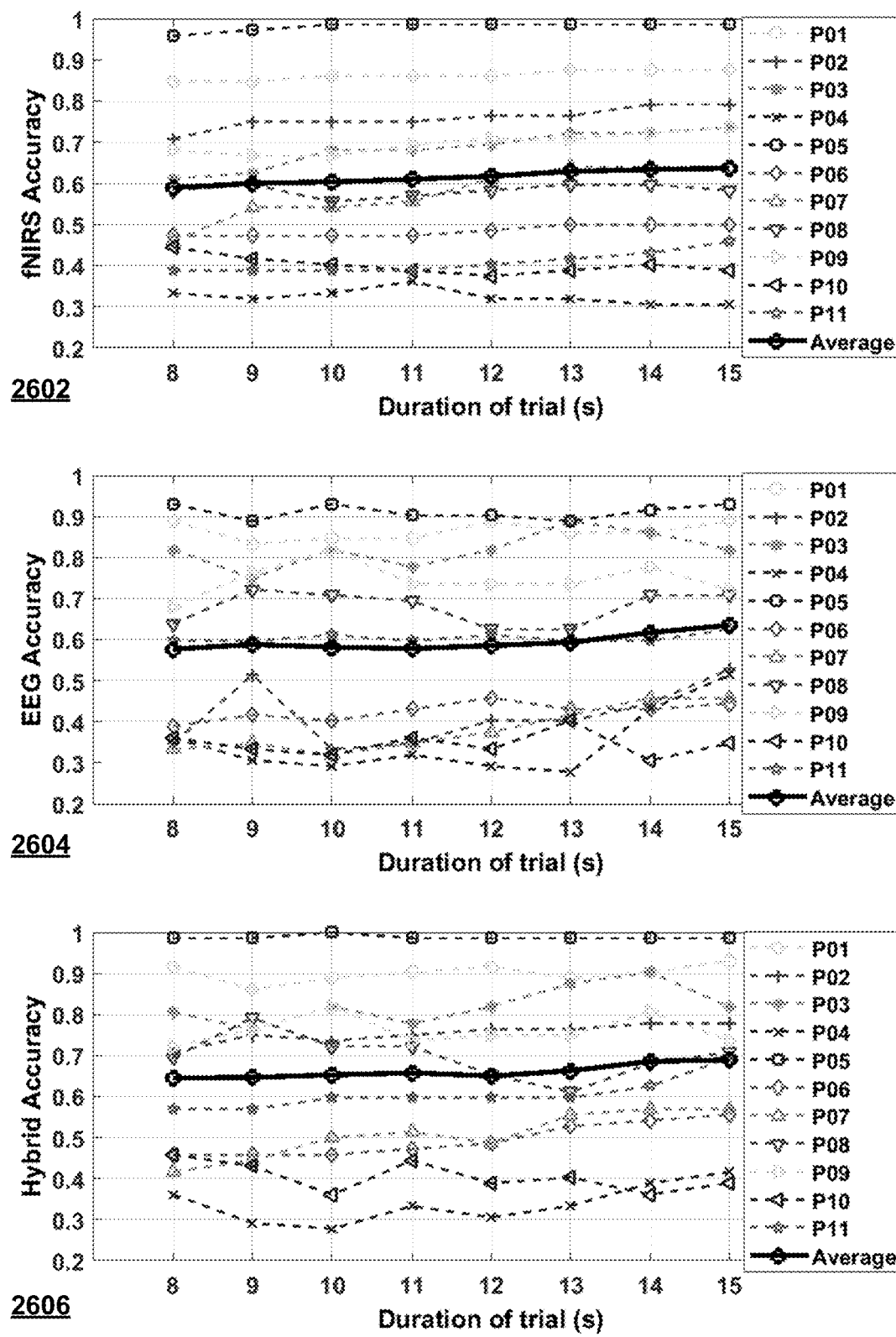
FIG. 26 illustrates an example of ternary classification accuracies for different trial durations, in accordance with some embodiments.

During the experiment, participants were asked to perform 15 seconds of each task. To increase the information transfer rate, one would want to determine the performance of the BCI for shorter durations of mental tasks. FIG. 26 illustrates the yes versus no versus rest classification accuracies (averaged across the three test blocks), had the duration of each trial been reduced. These hypothetical accuracies were estimated for eight different trial durations, from 8 s to 15 s (with 8 s suggested as the minimum fNIRS recording duration for observing a change in the hemodynamic response in a speech-related trial). The average fNIRS 2604 accuracies increased from 59.0% to 63.6% as the duration of trials was incremented from 8 to 15 s. For EEG 2602, the average accuracy changed from 57.7% at 8 s to 63.5 at 15 s, with some small fluctuations in between.

For the hybrid 2606 BCI, the mean accuracy across participants changed from 64.5%, at 8 s duration, to 68.9%, at 15 s duration. In general, there was a trade-off between the duration of each trial and the hybrid BCI accuracy. For most participants, the information transfer rate can be almost doubled without much loss in the accuracy. On the other hand, two participants (P6 and P7) surpassed the upper limit of the 99.9% confidence interval of chance (51.4%) only when the duration was longer than 13 s.

Discussion

Comparison with Previous Hybrid fNIRS-EEG BCIs

In some embodiments, a 3-class hybrid fNIRS-EEG BCI may be used based on imagined speech. An average ternary classification accuracy of 68.9.5±19.3% was reached across all participants, with 9 out of 11 participants surpassing the upper limits of 99.9% confidence limits of chance. When averaged across participants, the hybrid BCI outperformed both EEG and fNIRS BCIs with more than 5% enhancement in classification accuracy.

Most previous hybrid fNIRS-EEG BCIs based on active tasks focused on binary classification, either between two mental tasks or a mental task versus the idle state and mostly reported accuracy improvements of approximately 5% compared to each modality alone.

Comparison of the Information Transfer Rate (ITR) with Previous BCIs with Analogous Activation Tasks The ITR of the proposed BCI is compared to that of four studies using analogous activation tasks (Study 1, Study 2, Study 3 and Study 4 Chaudhary et al., 2017; Hwang et al., 2016; Sereshkeh et al., 2017a; Sereshkeh et al., 2017b). In all these studies, participants were asked to answer "yes versus no" questions. However, the exact instruction they were given was different. Study 3 and Study 4 instructed participants to mentally rehearse the phrases "yes" and "no" without any muscle and tongue movements. Study 2 asked participants to internally answer "yes" or "no". Study 1 instructed participants to think "ja" or "nein" (German for "yes" and "no"). Also, participants were explicitly instructed not to imagine the answer aurally or visually. In the study described herein, participants were instructed to think "yes" or "no" while repeating the answer mentally without any muscle or tongue movements.

For calculating the ITR, the following equation was used:

$$ITR = \frac{60}{\tau} \cdot \left[ \log_2 N + P.\log_2 P + (1-P).\log_2 \frac{1-P}{N-1} \right] \quad (7)$$

where $\tau$ is the trial duration, N is the number of classes and P is the classification accuracy.

The calculated ITRs of the binary "yes" versus "no" BCIs presented by Chaudhary et al. (2017), Hwang et al. (2016), and Sereshkeh et al. (2017a) were 1.08±1.36, 1.06±0.25, 0.94±0.12 bits/min, respectively. For the ternary yes versus no versus idle state BCI presented by Sereshkeh et al. (2018), the ITR was 0.94±0.83 bits/min. In the study herein, the ITR of 2.03±1.84 bits/min was achieved. Furthermore, for selected participants, the duration of the mental task can be reduced to as low as 8 s without much reduction in the classification accuracy (see FIG. 26).

FIG. 26 illustrates the ternary classification accuracies (averaged across the three last blocks) for different trial durations.

fNIRS-EEG Fusion Model

A technique to combine the data from two recording modalities is proposed. The results of the technique was compared to two previously suggested fNIRS-EEG fusion techniques on the dataset herein: (I) normalizing and merging the feature vectors from the two modalities and (II) training a classification model for each classifier and use a metaclassifier for combining these two classifiers. However, it was found that the technique described herein provided better performance.

The first technique (I) is a straightforward solution, i.e., combining data from two different modalities and leverages the discriminative information from both modalities in decision making. However, merging two feature vectors increases the input dimensionality and risk of overfitting. Hence, the number of trials needs to be sufficiently large for this technique to be optimal. Furthermore, the normalization parameters for each modality needs to be optimized for each participant, which increases the number of hyperparameters.

The second solution (II), which uses a metaclassifier, may appear to one not skilled in the art to resemble the technique described herein. However, feeding the output scores of two classifiers into a metaclassifier does not necessarily take the reliability of each classifier into account. For instance, if a classifier is overfitted on the training data, the output scores (which serve as the input to the metaclassifier) will be high, while in reality the classifier will fail to perform well on the test set. Using the cross-validation accuracy as a prior probability to adjust the output scores of each classifier can address this problem. As seen in FIG. 22, for most participants, one recording modality tended to dominate the decision-making, although the dominant modality varied across participants. In other words, the technique described herein appears to be ideal when the preferred BCI modality is participant-specific or may change from trial to trial.

In one embodiment, a BCI may be used to collect EGG signal data and fNIRS signal data representing a pattern of activity in the brain of a user. The collected pattern of activity may be compared to pre-defined patterns of activity for that user. If a match is found, then the collected pattern of activity may be deciphered to represent a response associated with the matched stored pattern. Patterns of activities are characterized by signal features as described above.

The forgoing described a hybrid 3-class fNIRS-EEG BCI based on imagined speech. In some embodiments, a hybrid modality can improve the classification performance compared to each modality alone. In some embodiments, an average classification accuracy of 68.9±19.3% was reached across eleven participants with nine participants surpassing chance.

In some embodiments, this BCI can be further developed with the option of making the decision sooner than the entire trial period, if the classifier's confidence surpasses a certain threshold. Some participants reached their highest performance in less than 10 s, while others required a longer duration to surpass chance. The option of selecting the class type earlier than the end of a trial may improve the ITR for some participants.

In some embodiments, a subject-independent hybrid BCI may be further provided using a general model based on data from all participants, and using transfer learning to fine tune the model using a small dataset from each new participant. This may be more feasible due to the innate subject-dependent nature of active BCIs.

In some embodiments, the BCI described above can be used starting at FIG. 19 where the model has previously been generated for the user/patient and is stored in a system. The stored model may be used to determine the class labels of data from new trials. In some embodiments, same-day test data trials may be used to prime/calibrate the model before actual new trials are run.

For example, an entertainment system may employ the methods described above to determine a user's state of "yes", "no" or "rest". The entertainment system may initially generate a model for each user and store the model in a memory. When the user connects to the entertainment system on a different day, the entertainment system may employ a short test data trial to prime/calibrate the model. Once calibrated, the model may be used by the entertainment system on new trials for the user.

In an aspect there is provided a device comprising a brain computer interface to process bio-signals using online classification of covert speech.

In some embodiments, the bio-signals comprise electroencephalography (EEG) signals.

In some embodiments, the bio-signals comprise functional near-infrared spectroscopy (fNIRS) signals.

In some embodiments, the classification comprises at least three classes.

In some embodiments, the at least three classes comprise yes, no and rest.

In some embodiments, the device has a display device for displaying visual elements and, in response, capturing the bio-signals.

In some embodiments, the device has a headset component configured to implement virtual reality or augmented reality by displaying visual elements at a display device and, in response, capturing the bio-signals.

In some embodiments, the device is further configured to activate one or more switches based on covert word repetition by the processing of the bio-signals.

In an aspect there is provided a device for real-time classification of covert speech having: a plurality of sensors for capturing real-time bio-signal data for brain monitoring in response to mental tasks delivered to a patient; a brain computer interface with memory storing instructions to configure a processor to provide: a data collection unit to pre-process the raw bio-signal data; feature extraction unit to extract a vector of features from the raw bio-signal data; oversampling unit to sample the raw bio-signal data; feature selection unit to select features from the vector of features; classification unit to build classification model to generate classified covert speech data using the selected features; an interface unit to control a display device with visual elements based on the classified covert speech data.

In some embodiments, the bio-signals comprise at least one of electroencephalography (EEG) signals and functional near-infrared spectroscopy (fNIRS) signals.

In an aspect there is provided a system comprising a brain computer interface to process electroencephalography (EEG) signals using online classification of covert speech.

In another aspect there is provided a process for a brain computer interface to process electroencephalography (EEG) signals using online classification of covert speech.

In a further aspect there is provided a brain computer interface device configured as described herein to process electroencephalography (EEG) signals using online classification of covert speech.

In an aspect there is provided a brain computer interface device configured to activate one or more switches based on covert word repetition (e.g. help vs resting) by processing electroencephalography (EEG) signals using online classification of covert speech.

In an aspect there is provided a brain computer interface device configured to execute one or more tasks based on covert word repetition by processing electroencephalography (EEG) signals using online classification of covert speech. For example, a user can express a choice (yes/no, left/right, stop/go).

In an aspect there is provided a device for real-time classification of covert speech. The device can have a plurality of sensors for capturing real-time raw EEG data for brain monitoring in response to mental tasks delivered to a patient. The device can have a brain computer interface with memory storing instructions to configure a processor to provide: a data collection unit to pre-process the raw EEG data; feature extraction unit to extract a vector of features from the raw EEG data; oversampling unit to sample the raw EEG data; feature selection unit to select features from the vector of features; classification unit to build classification model to generate classified covert speech data using the selected features; an interface unit to control a display device with visual elements based on the classified covert speech data. For example, a user uses a headset device offsite. The data processing can occur on the headset device itself.

In an aspect there is provided a system comprising a brain computer interface to process image, sensor and/or bio signal data using online classification of covert speech using features described herein.

In an aspect there is provided a process for a brain computer interface to process image, sensor and/or bio signal data using online classification of covert speech using features described herein.

In an aspect there is provided a brain computer interface device configured as described herein to process image, sensor and/or bio signal data using online classification of covert speech using features described herein.

In an aspect there is provided a healthcare system comprising brain computer interface device configured to execute one or more instructions based on covert word repetition by processing electroencephalography (EEG) signals using online classification of covert speech.

In an aspect there is provided a home control system comprising brain computer interface device configured to execute one or more instructions for controlling one or more home devices based on covert word repetition by processing electroencephalography (EEG) signals using online classification of covert speech.

In an aspect there is provided an entertainment system comprising brain computer interface device configured to execute one or more instructions based on covert word repetition by processing electroencephalography (EEG) signals using online classification of covert speech.

In another aspect there is provided a system comprising a brain computer interface to process functional near-infrared spectroscopy (fNIRS) signals using online classification of covert speech.

In another aspect there is provided a process for a brain computer interface to process functional near-infrared spectroscopy (fNIRS) signals using online classification of covert speech.

In another aspect there is provided a brain computer interface device configured as described herein to process functional near-infrared spectroscopy (fNIRS) signals using online classification of covert speech.

In another aspect there is provided a brain computer interface device configured to activate one or more switches based on covert word repetition by processing functional near-infrared spectroscopy (fNIRS) signals using online classification of covert speech.

In another aspect there is provided a brain computer interface device configured to execute one or more tasks based on covert word repetition by processing functional near-infrared spectroscopy (fNIRS) signals using online classification of covert speech.

In another aspect there is provided a device for real-time classification of covert speech comprising a plurality of sensors for capturing real-time infrared data for brain monitoring in response to mental tasks delivered to a patient. The device can have a brain computer interface with memory storing instructions to configure a processor to provide: a data collection unit to pre-process the raw functional near-infrared spectroscopy (fNIRS) optical signal data; a baseline removal unit to remove baseline collection data from the raw fNIRS data; feature extraction unit to extract a vector of features from the raw fNIRS data; feature selection unit to select features from the vector of features; classification unit to build classification model to generate classified covert speech data using the selected features; and an interface unit to control a display device with visual elements based on the classified covert speech data.

In another aspect there is provided a method for signal processing and feature extraction of fNIRS signal data collected from a BCI, the method comprising signal processing the fNIRS signal data by filtering the fNIRS signals using a FIR low-pass filter, baseline removal of the fNIRS signal data by removing, from each channel trial, a mean of an oxygenated hemoglobin concentration change ([HbO]) for the last 1.5 seconds of signal from the end of each 14 seconds of signal from each channel during a baseline signal period, feature extraction from the fNIRS signal data by calculating a mean of [HbO] for each channel during the length of each trial, and classification of the fNIRS signal data by using a regularized linear discriminant analysis algorithm.

In another aspect there is provided a healthcare system comprising brain computer interface device configured to execute one or more instructions based on covert word repetition by processing functional near-infrared spectroscopy (fNIRS) signals using online classification of covert speech.

In another aspect there is provided a home control system comprising brain computer interface device configured to execute one or more instructions for controlling one or more home devices based on covert word repetition by processing functional near-infrared spectroscopy (fNIRS) signals using online classification of covert speech.

In another aspect there is provided an entertainment system comprising brain computer interface device configured to execute one or more instructions based on covert word repetition by processing functional near-infrared spectroscopy (fNIRS) signals using online classification of covert speech.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, references were made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The foregoing discussion provides many example embodiments. Although each embodiment represents a single combination of inventive elements, other examples may include all possible combinations of the disclosed elements. Thus, if one embodiment comprises elements A, B, and C, and a second embodiment comprises elements B and D, other remaining combinations of A, B, C, or D, may also be used.

The term "connected" or "coupled to" may include both direct coupling (in which two elements that are coupled to each other contact each other) and indirect coupling (in which at least one additional element is located between the two elements).

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements. The embodiments described herein are directed to electronic machines and methods implemented by electronic machines adapted for processing and transforming electromagnetic signals which represent various types of information. The embodiments described herein pervasively and integrally relate to machines, and their uses; and the embodiments described herein have no meaning or practical applicability outside their use with computer hardware, machines, and various hardware components. Substituting the physical hardware particularly configured to implement various acts for non-physical hardware, using mental steps for example, may substantially affect the way the embodiments work. Such computer hardware limitations are clearly essential elements of the embodiments described herein, and they cannot be omitted or substituted for mental means without having a material effect on the operation and structure of the embodiments described herein. The computer hardware is essential to implement the various embodiments described herein and is not merely used to perform steps expeditiously and in an efficient manner.

For simplicity only one computing device 110 and 130 is shown in FIGS. 2 and 3, respectively, but the respective systems may include more computing devices 110 and 130 operable by users to access remote network resources 140 and exchange data. The computing devices 110 and 130 may be the same or different types of devices. The computing device 110 and 130 includes at least one processor, a data storage device (including volatile memory or non-volatile memory or other data storage elements or a combination thereof), and at least one communication interface. The computing device components may be connected in various ways including directly coupled, indirectly coupled via a network, and distributed over a wide geographic area and connected via a network (which may be referred to as "cloud computing").

Although the embodiments have been described in detail, it should be understood that various changes, substitutions and alterations can be made herein without departing from the scope as defined by the appended claims.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized. Accordingly, the appended claims are intended to include within their scope such processes, machines, manufacture, compositions of matter, means, methods, or steps.

As can be understood, the examples described above and illustrated are intended to be exemplary only. The scope is indicated by the appended claims.

What is claimed is:

1. A device for real-time classification of covert speech comprising:
    a plurality of sensors for capturing real-time raw bio-signal data for brain monitoring in response to covert speech mental tasks delivered to a user, the real-time raw bio-signal data comprising raw electroencephalography (EEG) signal data and raw functional near-infrared spectroscopy (fNIRS) signal data;
    a brain computer interface with memory storing instructions to configure a processor to:
        pre-process the raw bio-signal data;
        extract a vector of features from the EEG signal data and a vector of features from the fNIRS signal data using a spectral estimation method and a time frequency method;
        select features from the vector of features from the EEG signal data and from the vector of features from the fNIRS signal data using a feature selection method;
        build a classification model for the EEG signal data and a classification model for the fNIRS signal data to generate classified covert speech data using the selected features using at least one of:
            a machine learning classifier method; and
            a regularization parameter; and
        control a display device with visual elements based on the classified covert speech data; wherein:
    to pre-process the raw EEG signal data the processor is further configured to:
        filter the EEG signals using a band-pass filter; and
        remove electrooculography (EOG) and eye blink artifacts;
    to pre-process the raw fNIRS signal data the processor is further configured to:
        filter the fNIRS signals using a low-pass filter; and
        remove, from each channel trial, a mean of baseline data prior to that trial;
    to extract the vector of features for the EEG signal data, the processor is further configured to:
        determine a discrete wavelet transform to one or more decomposition levels;
    to extract the vector of features for the fNIRS signal data, the processor is further configured to:
        determine a mean value of oxygenated hemoglobin concentration change;
    to select features from the vector of features for the EEG signal data, the processor is further configured to:
        perform runs of K-fold cross validation (CV) on data using regularized linear discriminant analysis (RLDA) for different values of qamma (Y);
        select the gamma (Y) resulting in a highest cross-validation accuracy obtained with regularization parameter $Y_{EEG}$; and
        determine a highest cross validation accuracy regularization parameter $A^*_{EEG}$;
    to select features from the vector of features for the fNIRS signal data, the processor is further configured to:
        perform runs of K-fold CV on data using RLDA for different values of gamma (Y);
        select the gamma (Y) resulting in a highest cross-validation accuracy obtained with regularization parameter $Y_{fNIRS}$; and
        determine a highest cross validation accuracy regularization parameter $A^*_{fNIRS}$;
    to build the classification model for the EEG signal data, the processor is further configured to:
        employ a RLDA algorithm using regularization parameter EEG; and
    to build the classification model for the fNRIS signal data, the processor is further configured to:
        employ the RLDA algorithm using regularization parameter $Y_{fNIRS}$.

2. The device as claimed in claim 1, wherein the processor is further configured to:
    oversample the raw bio-signal data by a factor.

3. The device as claimed in claim 1, wherein the processor is further configured to:
    receive bio-signal data from a new trial, the bio-signal data comprising fNIRS signal data and EEG signal data;
    perform signal processing and feature extraction on the fNIRS signal data to generate a new trial fNIRS feature vector;
    perform signal processing and feature extraction on the EGG signal data to generate a new trial EGG feature vector;
    employ the RLDA model using regularization parameter Y $f_{NIRS}$ to determine first fNIRS probabilities for each label class, the label classes comprising one of "yes", "no", and "rest";
    employ the RLDA model using regularization parameter $Y_{EEG}$ to determine first EEG probabilities for each label class;
    multiply the first fNIRS probabilities by a factor of the highest cross validation accuracy regularization parameter ($A^*_{EEG}$) for fNIRS to determine second fNIRS probabilities for each label class;
    multiply the first EEG probabilities by a factor of highest cross validation accuracy regularization parameter ($A^*_{EEG}$) for EEG to determine second EEG probabilities for each label class; and
    determine a class label for the new trial, the class label selected from the label classes associated with a largest confidence value among the second fNIRS probabilities and the second EEG probabilities.

4. The device as claimed in claim 1, wherein the classification comprises at least three classes comprising: "yes", "no" and "rest".

5. The device as claimed in claim 1, further comprising:
    a display device for displaying visual elements and, in response, capturing the bio-signals.

6. The device as claimed in claim 1, further comprising:
a headset component configured to implement virtual reality or augmented reality by displaying visual elements at a display device and, in response, capturing the bio-signals.

7. The device as claimed in claim 1, wherein the processor is further configured to:
activate one or more switches based on covert word repetition by the processing of the bio-signals.

8. A device for real-time classification of covert speech comprising:
a plurality of sensors for capturing real-time raw bio-signal data for brain monitoring in response to covert speech mental tasks delivered to a user, the real-time raw bio-signal data comprising raw electroencephalography (EEG) signal data,
a brain computer interface with memory storing instructions to configure a processor to:
pre-process the raw bio-signal data;
extract a vector of features from the raw bio-signal data using a spectral estimation method and a time frequency method;
select features from the vector of features using a feature selection method;
build a classification model to generate classified covert speech data using the selected features using at least one of:
a machine learning classifier method; and
a regularization parameter; and
control a display device with visual elements based on the classified covert speech data; and wherein:
to pre-process the raw EEG signal data the processor is further configured to:
filter the EEG signals using a band-pass filter; and
remove electrooculography (EOG) and eye blink artifacts;
to extract the vector of features, the processor is further configured to:
determine an AutoRegressive model of order two or more; and
determine a wavelet transformation to one or more decomposition levels; and
to select features from the vector of features, the processor is further configured to:
apply a fast correlation-base filter to the vector of features;
to build the classification model, the processor is further configured to:
employ a linear support vector machine (SVM) algorithm using the selected features.

9. A device for real-time classification of covert speech comprising:
a plurality of sensors for capturing real-time raw bio-signal data for brain monitoring in response to covert speech mental tasks delivered to a user, the real-time raw bio-signal data comprising raw functional near-infrared spectroscopy (fNIRS) signal data,
a brain computer interface with memory storing instructions to configure a processor to:
pre-process the raw bio-signal data;
extract a vector of features from the raw bio-signal data using a spectral estimation method and a time frequency method;
select features from the vector of features using a feature selection method;
build a classification model to generate classified covert speech data using the selected features using at least one of:
a machine learning classifier method; and
a regularization parameter; and
control a display device with visual elements based on the classified covert speech data; and wherein:
to pre-process the raw fNIRS signal data the processor is further configured to:
filter the fNIRS signals using a low-pass filter; and
remove, from each channel trial, a mean of an oxygenated hemoglobin concentration change ([HbO]) from each channel during a baseline signal period;
to extract the vector of features, the processor is further configured to:
determine a mean of [HbO] for each channel during the length of each trial; and
to build the classification model, the processor is further configured to:
employ a regularized linear discriminant analysis (RLDA) algorithm using the selected features.

10. A computer-implemented method of real-time classification of covert speech, the method comprising:
capturing, by a processor coupled to a plurality of sensors, real-time raw bio-signal data for brain monitoring in response to covert speech mental tasks delivered to a user, the real-time raw bio-signal data comprising raw electroencephalography (EEG) signal data and raw functional near-infrared spectroscopy (fNIRS) signal data;
pre-processing, by the processor, the raw bio-signal data;
extracting, by the processor, a vector of features from the EEG signal data and a vector of features from the fNIRS signal data using a spectral estimation method and a time frequency method;
selecting, by the processor, features from the vector of features from the EEG signal data and from the vector of features from the fNIRS signal data using a feature selection method;
building, by the processor, a classification model for the EEG signal data and a classification model for the fNIRS signal data to generate classified covert speech data using the selected features using at least one of:
a machine learning classifier method; and
a regularization parameter; and
controlling, by the processor, a display device with visual elements based on the classified covert speech data; wherein:
pre-processing the raw EEG signal data comprises:
filtering, by the processor, the EEG signals using a band-pass filter; and
removing, by the processor, electrooculography (EOG) and eye blink artifacts;
pre-processing the raw fNIRS signal data comprises:
filtering, by the processor, the fNIRS signals using a low-pass filter; and
removing, by the processor, from each channel trial, a mean of the baseline data prior to that trial;
extracting the vector of features for the EEG signal data comprises:
determining, by the processor, a discrete wavelet transform to one or more decomposition levels;
extracting the vector of features for the fNIRS signal data comprises:
determining, by the processor, a mean value of oxygenated hemoglobin concentration change;

selecting features from the vector of features for the EEG signal data comprises:
  performing, by the processor, runs of K-fold cross validation (CV) on data using regularized linear discriminant analysis (RLDA) for different values of qamma (Y); and
  selecting, by the processor, the gamma (Y) resulting in a highest cross-validation accuracy ($Y_{EEG}$); and
  determining, by the processor, a highest cross validation accuracy ($A^*_{fNIRS}$);
selecting features from the vector of features for the fNIRS signal data comprises:
  performing, by the processor, runs of K-fold CV on data using RLDA for different values of gamma (Y);
  selecting, by the processor, the gamma (Y) resulting in a highest cross-validation accuracy ($Y_{fNIRS}$); and
  determining, by the processor, a highest cross validation accuracy ($A^*_{EEG}$);
building the classification model for the EEG signal data comprises:
  employing, by the processor, a RLDA algorithm using $Y_{EEG}$; and
building the classification model for the fNRIS signal data comprises:
  employing, by the processor, the RLDA algorithm using $Y_{fNIRS}$.

11. The method as claimed in claim 10, further comprising:
  oversampling, by the processor, the raw bio-signal data by a factor.

12. The method as claimed in claim 10, further comprising:
  receiving bio-signal data from a new trial, the bio-signal data comprising fNIRS signal data and EEG signal data;
  performing signal processing and feature extraction on the fNIRS signal data to generate a new trial fNIRS feature vector;
  performing signal processing and feature extraction on the EGG signal data to generate a new trial EGG feature vector;
  employing the RLDA model using regularization parameter $Y_{fNIRS}$ to determine first fNIRS probabilities for each label class, the label classes comprising one of "yes", "no", and "rest";
  employing the RLDA model using regularization parameter $Y_{EEG}$ to determine first EEG probabilities for each label class;
  multiplying the first fNIRS probabilities by a factor of the highest cross validation accuracy regularization parameter ($A^*_{EEG}$) for fNIRS to determine second fNIRS probabilities for each label class;
  multiplying the first EEG probabilities by a factor of highest cross validation accuracy regularization parameter ($A^*_{EEG}$) for EEG to determine second EEG probabilities for each label class; and
  determining a class label for the new trial, the class label selected from the label classes associated with a largest confidence value among the second fNIRS probabilities and the second EEG probabilities.

13. The method as claimed in claim 10, wherein the classification comprises at least three classes comprising "yes", "no" and "rest".

14. The method as claimed in claim 10, further comprising:
  displaying, by the processor on a display, visual elements and, in response, capturing the bio-signals.

15. The method as claimed in claim 10, further comprising:
  implementing, by the processor on a headset component, virtual reality or augmented reality by displaying visual elements at a display device and, in response, capturing the bio-signals.

16. The method as claimed in claim 10, further comprising:
  activating, by the processor, one or more switches based on covert word repetition by the processing of the bio-signals.

17. A computer-implemented method of real-time classification of covert speech, the method comprising:
  capturing, by a processor coupled to a plurality of sensors, real-time raw bio-signal data for brain monitoring in response to covert speech mental tasks delivered to a user, the real-time raw bio-signal data comprising raw electroencephalography (EEG) signal data,
  pre-processing, by the processor, the raw bio-signal data;
  extracting, by the processor, a vector of features from the raw bio-signal data using a spectral estimation method and a time frequency method;
  selecting, by the processor, features from the vector of features using a feature selection method;
  building, by the processor, a classification model to generate classified covert speech data using the selected features using at least one of:
    a machine learning classifier method; and
    a regularization parameter; and
  controlling, by the processor, a display device with visual elements based on the classified covert speech data;
  and wherein:
  pre-processing the raw EEG signal data comprises:
    filtering, by the processor, the EEG signals using a band-pass filter; and
    removing, by the processor, electrooculography (EOG) and eye blink artifacts;
  extracting the vector of features comprises:
    determining, by the processor, an AutoRegressive model of order two or more; and
    determining, by the processor, a wavelet transformation to one or more decomposition levels;
  selecting features from the vector of features comprises:
    applying, by the processor, a fast correlation-base filter to the vector of features; and
  building the classification model comprises:
    employing, by the processor, a linear support vector machine (SVM) algorithm using the selected features.

18. A computer-implemented method of real-time classification of covert speech, the method comprising:
  capturing, by a processor coupled to a plurality of sensors, real-time raw bio-signal data for brain monitoring in response to covert speech mental tasks delivered to a user, the real-time raw bio-signal data comprising raw functional near-infrared spectroscopy (fNIRS) signal data,
  pre-processing, by the processor, the raw bio-signal data;
  extracting, by the processor, a vector of features from the raw bio-signal data using a spectral estimation method and a time frequency method;
  selecting, by the processor, features from the vector of features using a feature selection method;
  building, by the processor, a classification model to generate classified covert speech data using the selected features using at least one of:

a machine learning classifier method; and
a regularization parameter; and
controlling, by the processor, a display device with visual elements based on the classified covert speech data;
and wherein:
pre-processing the raw fNIRS signal data comprises:
filtering, by the processor, the fNIRS signals using a FIR low-pass filter; and
removing, by the processor, from each channel trial, a mean of an oxygenated hemoglobin concentration change ([HbO]) from each channel during a baseline signal period;
extracting the vector of features comprises:
determining, by the processor, a mean of [HbO] for each channel during the length of each trial;
selecting features from the vector of features comprises:
performing, by the processor, a gamma selection; and
building the classification model comprises:
employing, by the processor, a regularized linear discriminant analysis (RADA) algorithm using the selected features.

19. A non-transitory computer-readable storage medium having instructions thereon which when executed by a processor perform a method of real-time classification of covert speech, the method comprising:
capturing, by the processor coupled to a plurality of sensors, real-time raw bio-signal data for brain monitoring in response to covert speech mental tasks delivered to a user, the real-time raw bio-signal data comprising raw electroencephalography (EEG) signal data and raw functional near-infrared spectroscopy (fNIRS) signal data;
pre-processing the raw bio-signal data;
extracting a vector of features from the EEG signal data and a vector of features from the fNIRS signal data using a spectral estimation method and a time frequency method;
selecting features from the vector of features from the EEG signal data and from the vector of features from the fNIRS signal data using a feature selection method;
building a classification model for the EEG signal data and a classification model for the fNIRS signal data to generate classified covert speech data using the selected features using at least one of:
a machine learning classifier method; and
a regularization parameter; and
controlling a display device with visual elements based on the classified covert speech data; wherein:
pre-processing the raw EEG signal data comprises:
filtering, by the processor, the EEG signals using a band-pass filter; and
removing, by the processor, electrooculography (EOG) and eye blink artifacts;
pre-processing the raw fNIRS signal data comprises:
filtering, by the processor, the fNIRS signals using a low-pass filter; and
removing, by the processor, from each channel trial, a mean of the baseline data prior to that trial;
extracting the vector of features for the EEG signal data comprises:
determining, by the processor, a discrete wavelet transform to one or more decomposition levels;
extracting the vector of features for the fNIRS signal data comprises:
determining, by the processor, a mean value of oxygenated hemoglobin concentration change;
selecting features from the vector of features for the EEG signal data comprises:
performing, by the processor, runs of K-fold cross validation (CV) on data using regularized linear discriminant analysis (RLDA) for different values of gamma (Y); and
selecting, by the processor, the gamma (Y) resulting in a highest cross-validation accuracy ($Y_{EEG}$); and
determining, by the processor, a highest cross validation accuracy ($A^*_{fNIRS}$):
selecting features from the vector of features for the fNIRS signal data comprises:
performing, by the processor, runs of K-fold CV on data using RLDA for different values of gamma (Y);
selecting, by the processor, the gamma (Y) resulting in a highest cross-validation accuracy ($Y_{fNIRS}$); and
determining, by the processor, a highest cross validation accuracy ($A^*_{EEG}$);
building the classification model for the EEG signal data comprises:
employing, by the processor, a RLDA algorithm using $Y_{EEG}$; and
building the classification model for the fNRIS signal data comprises:
employing, by the processor, the RLDA algorithm using $Y_{fNIRS}$.

* * * * *